(12) United States Patent
Boecker et al.

(10) Patent No.: US 10,738,316 B2
(45) Date of Patent: Aug. 11, 2020

(54) PROCESS FOR PRODUCING CHIMERIC CYCLOOLIGODEPSIPEPTIDES IN FILAMENTOUS FUNGI

(71) Applicant: TECHNISCHE UNIVERSITAET BERLIN, Berlin (DE)

(72) Inventors: Simon Boecker, Berlin (DE); Dirk Storm, Markdorf (DE); Vera Meyer, Berlin (DE); Lennart Richter, Berlin (DE); Sophia Zobel, Berlin (DE); Franziska Wanka, Berlin (DE); Roderich Suessmuth, Berlin (DE); Agnes Muehlenweg, Berlin (DE)

(73) Assignee: TECHNISCHE UNIVERSITÄT BERLIN, Berlin (DE)

( * ) Notice: Subject to any disclaimer, the term of this patent is extended or adjusted under 35 U.S.C. 154(b) by 85 days.

(21) Appl. No.: 15/127,645

(22) PCT Filed: Mar. 20, 2015

(86) PCT No.: PCT/EP2015/055978
§ 371 (c)(1),
(2) Date: Sep. 20, 2016

(87) PCT Pub. No.: WO2015/140315
PCT Pub. Date: Sep. 24, 2015

(65) Prior Publication Data
US 2017/0137832 A1    May 18, 2017

(30) Foreign Application Priority Data

Mar. 20, 2014 (EP) .................................. 14160821

(51) Int. Cl.
| | | |
|---|---|---|
| C12N 15/80 | (2006.01) | |
| C12P 17/14 | (2006.01) | |
| C12P 21/02 | (2006.01) | |
| C12N 15/52 | (2006.01) | |
| C07K 11/02 | (2006.01) | |
| C12N 9/00 | (2006.01) | |
| C12N 1/14 | (2006.01) | |
| C12P 21/00 | (2006.01) | |

(52) U.S. Cl.
CPC .............. *C12N 15/80* (2013.01); *C07K 11/02* (2013.01); *C12N 1/14* (2013.01); *C12N 9/00* (2013.01); *C12N 15/52* (2013.01); *C12P 17/14* (2013.01); *C12P 21/00* (2013.01); *C12P 21/02* (2013.01)

(58) Field of Classification Search
None
See application file for complete search history.

(56) References Cited

U.S. PATENT DOCUMENTS

| 5,747,448 A | 5/1998 | Ohyama et al. | |
|---|---|---|---|
| 6,893,839 B1 * | 5/2005 | Berka .................. | C12N 9/88 435/183 |
| 7,285,404 B1 * | 10/2007 | Midoh .................. | C12N 9/00 435/183 |
| 2012/0146047 A1 | 6/2012 | Kneissl et al. | |

FOREIGN PATENT DOCUMENTS

EP    1215281    6/2002

OTHER PUBLICATIONS

Meyer et al., AEM, 2011, vol. 77 No. 9, pp. 2975-2983.*
Sussmuth et al., Nat. Prod. Rep., 2011, vol. 28, pp. 99-124.*
Driouch et al., Biotechnology and Bioengineering, 2009, vol. 105 No. 6, pp. 1058-1068.*
International Search Report for PCT/EP2015/055978, Completed by the European Patent Office on Jun. 15, 2015, 8 Pages.
Carvalho et al. Appl. Microbiol Biotechnol. 2010, vol. 87 pp. 1463-1473, "Expanding the ku70 toolbox for filamentous fungi: establishment of complementation vectors and recipient strains for advanced gene analyses".
Datsenko et al. Proc. Natl. Acad Sci USA Jun. 6, 2000, vol. 97, No. 12, pp. 6640-6645, "One-step inactivation of chromosomal genes in *Escherichia coli* K-12 using PCR products".
Driouch et al. Biotechnology and Bioengineering Apr. 15, 2010, vol. 105, No. 6, pp. 1058-1068, XP 002740897 "Morphology Engineering of Aspergillus niger for Improved Enzyme Production".
Fiefel et al. ChemBioChem 2007, vol. 8, pp. 1767-1770, "In Vitro Synthesis of New Enniatins: Probing the a-D-Hydroxy Carboxylic Acid Binding Pocket of the Multienzyme Enniatin Synthetase".
Gust et al. The John Innes Centre, Norwich, United Kingdom 2002, 39 Pages, "PCR targeting system in Streptomyces coelicolor A3(2)".
Gust et al. Proc. Natl. Acad Sci USA Feb. 18, 2003, vol. 100, No. 4, pp. 1541-1546, "PCR-targeted Streptomyces gene replacement identifies a protein domain needed for biosynthesis of the sesquiterpene soil odor geosmin".
Haese et al. Molecular Microbiology 1993, vol. 7, No. 6, pp. 905-914, "Molecular characterization of the enniatin synthetase gene encoding a multifunctional enzyme catalysing N-methyldepsipeptide formation in Fusarium scirpi".
Halo, Dissertation submitted to the University of Bristol Dec. 2008, pp. 1-217, XP 05195439, "Generating New Compounds by Genetically Engineering Fungal Polyketide Biosynthesis".
Madry et al. Eur. J. Applied Microbiology and Biotechnology Mar. 1983, vol. 17, No. 2, pp. 75-79, XP 035171867, "Enniatin Production by Fusarium oxysporum in Chemically Defined Media".

(Continued)

*Primary Examiner* — Nancy J Leith
(74) *Attorney, Agent, or Firm* — Brooks Kushman P.C.

(57) ABSTRACT

A method for obtaining at least one microbial secondary metabolite or a derivative thereof, the method includes the step of heterologous expression of at least one synthetase of the secondary metabolite in at least one filamentous fungus. Also disclosed is an expression cassette, a plasmid vector including the expression cassette, an expression host, cyclodepsipeptides and a chimeric cyclodepsipeptide synthetase.

9 Claims, 31 Drawing Sheets

Specification includes a Sequence Listing.

(56) References Cited

OTHER PUBLICATIONS

Mattern et al. Molecular & General Genetics 1992, vol. 234, No. 2, pp. 332-336, "Isolation and characterization of mutants of Aspergillus niger deficient in extracellular proteases".
Matthes et al. Chem. Commun. 2012, vol. 48, pp. 5674-5676, "In vitro chemoenzymatic and in vivo biocatalytic syntheses of new beauvericin analogues".
Meyer et al. Applied and Environmental Microbiology May 2011, vol. 77, No. 9, pp. 2975-2983, XP 002740895, "Fungal Gene Expression on Dmenad: An Inducible, Tunable, and Metabolism-Independent Expression System for Aspergillus niger".
Punt et al. Gene 1990, vol. 93, No. 1, pp. 101-109, "Functional elements in the promoter region of the Aspergillus nidulans gpdA gene encoding glyceraldehyde-3-phosphate dehydrogenase".
Punt et al. Methods in Enzymology, Academic Press 1992, vol. 216, pp. 447-457, "Transformation of Filamentous Fungi Based on Hygromycin B and Phleomycin Resistance Markers".
Richter et al. Fungal Biology and Biotechnology Oct. 14, 2014, vol. 1, 14 Pages, XP 021200577, "Engineering of Aspergillus niger for the production of secondary metabolites".
Sussmuth et al. Natural Product Reports 2011, vol. 28, No. 1, pp. 99-124, XP 002740896, "Fungal cyclooligomer depsipeptides: From classical biochemistry to combinatorial biosynthesis".
Xu et al. Chemistry and Biology Sep. 22, 2008, vol. 15, pp. 898-907, "Biosynthesis of the Cyclooligomer Depsipeptide Beauvericin, a Virulence Factor of the Entomopathogenic Fungus Beauveria bassiana".
Xu et al. Fungal Genetics Biology 2009, vol. 46, No. 5, pp. 353-364, "Biosynthesis of the cyclooligomer depsipeptide assianolide, an insecticidal virulence factor of Beauveria bassiana".

Xu et al. Biotechnology and Bioprocess Engineering 2010, vol. 15, pp. 460-466, "Optimization of a Liquid Medium for Beauvericin Production in Fusarium redolens Dzf2 Mycelial Culture".
Yu et al. Chemical Communications Jul. 14, 2013, vol. 49, pp. 6176-6178, "Functional dissection and module swapping of fungal cyclooligomer depsipeptide synthetases".
Yu et al. Metabolic Engineering 2013, vol. 18, pp. 60-68, "Engineered production of fungal anticancer cyclooligome depsipeptides in *Saccharomyces cerevisiae*".
Zhang et al. Nature Genetics Oct. 1998, vol. 20, pp. 123-128, "A new logic for DNA engineering using recombination in *Escherichia coil*".
Muller et al. ChemBioChem. 2009, vol. 10, pp. 323-328, "In vitro Synthesis of New Cyclodepsipeptides of the PF1022-type: Probing the a-D-Hydroxy Acid Tolerance of PF1022 Synthetase".
Japanese Office Action for Japanese Application No. JP 2017-500432, English Summary attached to original, dated Feb. 13, 2018, All together 8 Pages.
Wucherpfenning et al. J. Vis. Exp. 61, e4023 (2012), "Customization of Aspergillus niger Morphology Through Addition of Talc Micro Particles".
Zheng, Zongming, "Advances in main domains of nonribosomal peptide synthetases"; Chin. J. Antibiot. vol. 30, No. 2, 120-124, Feb. 2005 (English Abstract).
Xu, Tengyang et al., "Regulation of microparticles on Aspergillus niger enzyme production by fermentation." Proceedings of the 9th Annual Meeting of China Food Science and Technology Institutes in China, Dec. 31, 2012.
Chinese Office Action for Chinese Application No. 201580022033.9 dated Mar. 4, 2019.

* cited by examiner

Seq ID No 1

PF/Enniatin Chimeric Synthetase:

>PF/ESyn

ATGTCAAACATGGCACCACTCCCTACGATGGGCGTTGAGCAGCAAGCCCT
ATCACTTTCATGCCCCTTACTCCCTCATGACGATGAGAAACACTCAGACA
ACCTTTACGAGCAAGCAACTCGGCACTTCGGCTTGAGCCGAGACAAGATC
GAAAATGTCTTACCATGTACTTCCTTTCAATGTGATGTCATAGATTGCGC
CGTCGACGATCGGCGGCATGCTATCGGTCACGTCGTCTATGATATCCCCA
ATACAGTGGACATCCAGCGTTTAGCCGCAGCCTGGAAGAGGTTGTGCGG
CAGACACCAATCTTGAGGACCGGCATCTTTACATCAGAAACCGGCGACTC
TTTTCAGATCGTCTTGAAAGAAGGCTGCCTACCGTGGATGTACGCGACAT
GTCTCGGCATGAAGGGGGCAGTGATACAAGATGAAGCAGTCGCCGCTATG
ACTGGACCGCTTGCAATCGATATGTCGTCCTGGAGGACCCGAGTACGAA
GCAAAGGCTGCTCATCTGGACATTCAGCCATGCTTTAGTGGATTATACAG
TCCAGGAACGCATCCTTCAGCCGGGTTCTCACAGTATACGACGGCCGGGAC
GTCGAGTGCCCTCGCATCAAGTATACAGAACATGTCTCTCGGTTTTGGCA
ACAACACTTTGAAGGCTTAGATGCCTCCGTATTTCCCCTTCTACCATCTC
ACCTAACTGTCTGCAATCCCAATGCGCGCGCAGAACATCATATCTCATAC
ACGGGACCAGTCCAGAGGAAGTGGTCCCATACAAGTATCTGTCGGGCTGC
ACTCGCAGTTCTTCTATCTCGCTTTACACACTCTTCGGAGGCCCTCTTCG
GTGTTGTGACAGAACAATCTCACAACTCCGAGGACCAAAGACGTCAATT
GATGGCCCCGCAAGGACAGTAGTGCCTATCCGGTCCTTTGTGCCCAGA
TCAATATGTGTCGGATGTCATTGGGGCAATCACCGCACACGAACACGCCA
TGCGCGGGTTTGAGCAGGCTGGACTTCGCAATATCCGCCGTACCGGAGAC
GACGGGTCTGCTGCTTGTGGATTCCAGACCCGTGCTACTGGTGACTGACGG
TGATGCTCCCAAGACCCCTGGGAGTGTACTTCATCGAAGTGTAGAAGAAT
CGGATAGATTCATGCCCTGCGCTAATCGTGCCCTTCTGCTCGACTGCCAG
ATGGCTGGCAACTCGGCATCCCTAGTCGCACGATATGATCATAATGTGAT
CGACCCACGCCAGATGTCTCGCTTCCTGCGACAGCTAGGATACCTGATCC
AACAATTTCATCATCACGTCGATCTGCCTCTGGTCAAAGAACTGGACGTC
GTGACGGCGGAGGATTGTGCGGAAATCGAGAAATGGAATTCAGAACGCCT
AACAATGCAAGACGCCTTAATCCACGACACCATATCCAAGTGGGCTGCTG
GCGATCCCAACAAGCTGCAGTTTTCGCTTGGGATGGGGAATGGACATAC
GCCGAGCTAGACAACATATCCTCCCGTCTCGCCGTGTATATCCAATCCCT
GGACTTGAGACCAGGACAAGCAATACTCCCACTCTGCTTCGAGAAGTCAA

Figure 26 (Cont.)

```
AATGGGTCGTCGCCACAATTCTCGCCGTCCTCAAAGCCGGTCGGGCATTC
ACACTCATCGACCCGTGCGACCCCTCGGCAAGGATGGCCCAGGTCTGTCA
GCAGACCTCCGCCACAGTCGCTCTCACCTCCAAACTCCACAACACCACCT
TACGTTCCGTCGTTTCCCGCTGCATTGTGGTCGACGACGACCTCCTTCGG
TCCTTACCCCGCGCCGATGGCCGGCTTAAAGCCCACCGTGAAGCCACAGGA
CTTGGCCTATGTTATTTTCACATCTGCAGCACAGGAGAGCCGAAAGGCA
TCATCATCGAACATCGGGGGTTCGTGTCGTGCTATGAAATTTGGCCCC
GCGCTCGGAATGGATGAGCACAGGCGCGCTCTTCAATTCGCCTCATATGC
GTTGGCGCTTGTCTGGTAGAAGTTGTGACAGCTCTGATGCACGGCGGCT
GCGTCTGCATCCCTTCCGATGACGATCGCTTGAACAATGTACCGGAGTTC
ATCAAAAGGGCCCAGGTGAACTGGGTGATACTCACTCCGTCGTATATCGG
GACATTCCAGCCGGAAGATGTCCCTGGACTGCAAACACTGGTATTGGTTG
GAGAACCTATCTGGCGTCTATTCGGATACCTGGGCTTCCTGGGTTCGA
CTCCTGAATGCCTACGGTCAGAGTGAAAGCTCAACTATGTGCAGCGTCAC
GGAAGTCAGCCCGCTCTCCCTCGAACCGACAATATCGGTCGGGCTGTAG
GCGCTACGATCCTGGATCATTGATCCCGACGAGCTGATCGTCTTGCTCCA
ATGGCTGCATTGGAGAGCTAGTGATCGAAAGTCCGGGCATTGCGCGCGA
CTATATCATCGCGCGCGCCGGACAAGTCCCGCCTTTCTCCTAGCACCGC
CGGCCTGGTACCAGCCGGGAAATTATCCAACGCCTTTAAATTTACAAG
ACTGGAGATCTCGTGCGTTATGGACCTGACGGCACCATCGTCTGCCTGGG
ACGCAAAGATTCGCAAGTGAAGATCCGAGGGCAGCGCCTAGAGATCAGCG
CACTGGAAGCCGTCTACGACGACAACTGCCTGGTGACATCATGCCCGTG
GCCGAAGCTATCAAACGCTCGGATTCGTCAGGCAGTACAGTCTTGACTGC
CTTCTTGATAGGGTCATCTAAGAGTTATCTGCGGCAGACGCCGTTATCT
TGGATCACGGTGCTACCACGAGATAACGCGAAGTTGCAGCAAATCCTT
CCCCAGCATTCCGTTCCATCCTGTTATCCACATGGAAATCTTCGTCG
AACTGCCACCGGCAAAGCGGACAGGAAATGCTTCGATCTATTGCTAGCA
AGCTATTGGTGAATTGTCTCAGAACGTGACATCTCAACCGATTGAGAAG
CACGATGCCCCGGCACCTGGTATAGAGGTCAAGCTGAAGGAGCTTTGGTT
TCTGAGCTTGAATCTTATCCCAACTCTCAAGATGTCGGAGCGAGTTTCT
TTGACTTAGGCGGAAATTCCATTATCGCCATCAAAATGGTAAACATGGCG
AGGTCAGCTGGATACCACTGAAGCTATCGGACATATTCCAGAATCCCAC
GCTCGCTGGTCTCAAGGCTATTGTCATTGTACTTCGCTGCTATACAGCC
TTATTCCAAGGTTACCCGCCAAGGCCCTGTTAGCGAGCAGTCTTATGCG
CAAAACAGAATGTGCTTCCTGGATCAGTTGTCTGAGGGTGCTTCATGGTA
TCTGATTCCTTTCGCTGTGCGCATGCGAGGTCCGGTGGATGTTGATGCGT
TGACGCCTGCTTTGCTCGCTCTTGAACAGCGTCATGAGACACTACGAACT
ACATTTGAGAACCAAGATGGTGTTGGAGTCCAGATCATCCATGATAGACT
```

Figure 26 (Cont.)

CTCCAAAGAGCTACAAGTCATCGATGCCTTGGATGGTGACGAGGGTGGTC
TCAAGACACTCTGCAAAGTAGAGACCACCACATTCGACATGACATCCGAA
GCAGGCTGGAGCTCAACCCTCATCCGCCTCGGCAAAGACGATCACATTCT
GTCTATCGTCATGCACCACATCATCTCCGACGGCTGGTCCATCGACGTTC
TCCGCCGCGAACTCATCGAACTCTAGGCCGCCGGTCTGCAGGGCAAGGAT
CCTTCCTCCGCACTAACTCCCCTACCCATCCAGTACAGCGACTTCGGCGT
GTGGCAGAAGCACGAGCCCAAGCAGCTGAGCACGACGAGGCAGCTCCAGT
ACTGGAAGAAGCAACTCGGCAGATAGGTCACCTGCCAAGATCCCTACCGAC
TGCTCCCGTCCAGATCTCCTGTCCGGTGACGCAGGCGTTGTGCTCGTTGC
CATCGACGGCCAGCTGTATCAGAAACTAAGGGGCTTCTGCAACAAGCACA
ACAGCACTGCCTTCTCCATCCTGCTCCCTGCTTTCCGCGCGGCGCATTAC
CGTCTCACAGCCCTTGACGACGCCGTGATCGGCATCCCCATTGCAAACCG
TAACCGCTGGAGCTGGAAACAGATCGATCCGTTCTTGTCAACACGCAGT
GTATGCGCATCGCCGTTGACGACGCGATACATTTGAGAGTCTGGTGCGC
CAGGTCAGATCTACCACTACAGCTGCGTTTGCGCACGAGGATGTCCCCTT
CGAGCGTGTCCTTCAGCGCTTCAGCCTGGCCATAGAGATCTCTGCGAA
CACCGCTGGCACAGATAATGTTTGCTGTTCACTCGCAGAAGACCTTGGA
CGTTTCGAGCTGGAGGGTATCCAGTCTGAGCCTATCGCCAGCAAGGCCTA
CACCAGATTCGATGTCGAGTTCCATCTGTTCCAACAGGCAGACGGACTGA
AGGGCAGTTGCAACTTTGCCACAGATCTCTTCAAGCCCGAAACTATCCAG
AATGTTGTCAGCGTGTTTTTCCAGATTCTACGCCATGGCCTTGACCAGCC
TGAGACGTGTATCTCGGTTCTTCCACTGACTGATGGAGTCGAGGAGCTTC
GCAGGTTGGATCTGCTGGAAATCAAGAGGACTAACTACCCTCGCGATTCG
AGCGTGGTAGATGTCTTCCGCGAACAAGCCTGCCGCCAACCTGCAGGTTAT
CGCTGTTACCGACTCATCTTCTCGTCTGACTTATGCAGAGCTGGACAATA
AGTCTGAGCTGCTCTCACGATGGCTTCGACGACTAACTTGACGCCAGAG
ACGCTGGTCAGTGTTCTGCTCGCCGGTCTTGCGAGACTATCGTTGCCTA
TGTTGGTATCCTCAAGGCGAACCTGGCGTATCTTCCTCTTGACGTGAGGT
CCCCGGTGACTCGTATGAAGGACATCTTGTCGAGCGTGTCTGGAAACACC
AAGTTCTTATGGGCTCTGGGTAGAGGATCCTGGCTTTGACTTACCGCA
ACTAGAGCTCCTACGCATCACCGACAACTTCGATGAGACCATCGAGGACG
TGCAAGACTCTCCCCAACCGTCTGCCACAAGCCTCGCCTACCTCGTCTTC
ACATCCGGTTCAACTGGTAAACCAAGGCGTCATGATCGAGCACCGGGC
CATTGTGCGTCTCGTCAAGAGTGACAACTTTCCTGGCTTCCCCTCCCCCG
CTCGGCATGTCAAATGTCTTCAACCCTGCCTTCGACGGAGCCATCTGGAG
ACAACTGGATGCTCCTGAACGGCGGAACAGTCGTCTGCATCGACTACGT
GACCACCCTGGACGGCAAAGAGCTCGCTGCTGTGTTCGCCAAAGAGCGCG
TCAACGCCGCCTTCTTCGCACCTGCGATGCTCAAGCTTTACCTCGTTGAT

Figure 26 (Cont.)

```
GCGCGCGAGGCTTTGAAGAATCTTGACTTCCTTATTGTTGGAGGTGAGAG
GTTCGATACCAAGGAAGCCGTGGAGGCCATGCCGCTTGTGAGGCAAGA
TTGCCAATATCTATGGTCCGACTGAGGCTGGAATAATCAGCACGTGCTAT
AACATCCCCAAGGATGAGGCTTACACCAATGGTGTTCCCATTGGTGGAAG
TATCTACAACTCTGGTGCCTACGTCATGGATCCTACCAGCAACTTGTCG
GCCTTGGCGTCATGGGAGAGCTTGTTGTTACCGGAGACGGTGTTGGTCGA
GGCTACACTAACCCCGAGCTCAACAAGAACCGCTTCATCGACATCACCAT
CGAGGGCAAGACTTTCAAGGCTTACCGTACTGGTGACCGGATGCGTGCAC
GACTGGCGACGGTCTCCTTGAGTTCTTCGGCCGCATGGACAACCAGTTC
AAGATCCGCGCCAACCGTATCGAAGCAGGGAAGTTGAGTCTGCCATGCT
CAGCCTCAAGAATGTCCTTAACGCCGCCATTGTCGTCCGCGGGGGCGGAG
AAGATGAAGGGCCACTCGAGATGGTCGGATTCATCGTGGCGGACGACAAG
AATGATGCCACGGCGAGAAGGATAGCTAACTAAGTTGAGGCTGGCA
GGACCATTTCCAGAGTGTATGTACTCGGATATCAGCACCGCCGTGGACC
AATCTGCCATTGGAAACGACTTTAAGGCTGGACTTCTATGTACGATGGT
AACGATATCGACAAGGCCAGATGCAGGAGTGGTTGGACGACGCTATTCA
CACCCTGCATAACGGCCAGATCCCCTGCGGATGTCCTCGAGATCGGTACCG
GTAGTGGTATGATCCTGTTCAACCTCAACCCGGGCCTCAACAGCTACGTT
GGTCTTGATCCATCCAAGTCAGCAGTCGAGTTCGTCAACAGAGCCGTCGA
GTCCTCTCCCAAGTTCGCAGGAAAGCCAAGGTCCACGTCGGCATGGCCA
CAGACGTCAACAAACTCGGCGAAGTACACCCCGATCTCGTGGTCTTCAAC
TCCGTTGTTCAATACTTCCCCACACCCCGAGTATCTCGCCGAGGTCATCGA
TGGCCTCATTGCCATCCCCAGCGTCAAGCGCATCTTCCTTGCGATATCA
GATCATATGCTACCAACGGACACTTCCTCGCCGCACGCGCTATCCACACG
CTCGGCACCAATAACAACGCCACCAAGGATAGGGTGCGCCAGAAGATCCA
GGAGCTGGAGGATCGAGGGAAGAGTTTCTCGTTGAGCCTGCCTTCTTCA
CCACTCTGAAGGAGCGACGTCCAGATGTTGTCAACCATGTTGAGATCATC
CCCAAGAACATGAAGGCCACCAACGAACTCAGCGCCTATCGCTACACGGC
TGTTGTGCATCTGCGGATGAAACGGACGAACCTGTGTATCATATTGAGA
AGGATAGCTGGGTTGACTTTGAGGCGAAGCAGATGGACAAGACGGCTCTT
CTTGACCACCTGCGCCTCTCCAAGGATGCTATGAGTGTGGCGGTTAGCAA
CATCACCTACGCCCACACTGCCTTTGAACGTCGTATCGTTGAGTCTCTCC
ATGAGGATAGCAAGGATGACACCAAGGGTACACTCGATGGTGCAGCCTGG
CTCTCAGCAGTTCGCTCCGAAGCCGAAACCGCGCCTCACTCACCGTCCC
CGACATCCTGCAGATCGCCAAGAGGCTGGTTTCCGAGTTGAAGTCAGCG
CTGGTCGCCAGTGGTCCCAAGTGGTGCTTTAGACGCAGTGTTCCACCGC
TTTCCACCCTCCAGCACTGACCGCACTCTAATCCAGTTCCCCACGGACAA
CGAGCTTCGATCATCACTCACCCTCGCCAACCGCCCTCTCCAGAAGCTGC
```

Figure 26 (Cont.)

```
AGCGCCGTCGTGCCGCTCTGCAAGTCCGCGAGAAGCTCCAGACGCTGGTC
CCGTCTTACATGGTTCCTCCGAATATCGTGGTGCTGGACACGATGCCTGT
CAATACTAACGGCAAGATCGACAGAAGGAGCTTACGCGTAGAGCACGAA
CACTGCCGAAGCAGCAGACTGCGGCGCCTGTGCCGGACTTCCCTATCTCT
GATATCGAGATCACGCTGTGCGAGGAGGCAACTGAGGTCTTTGGAATGAA
GGTTGAAATCAGCGATCACTTCTTCTAGCTCGGTGGTCACTTCTCCTCG
CTACGAAACTCATTTCTCGCATCCAGCACCGTCTCCATGTGCGGTTACT
GTGAAGGACGTATTCGACAGCCCTGTCTTTGCCGATCTGGCAGTCATCAT
CCCTCAAGGACTTGCTATGCAGAACCCTGTTGCTGAAGGACAGGACAAGC
AAGGCTGGTCCTCGAGAGTTGCCCCTCGTACAGAAGTCGAGAAGATGCTG
TGCGAGGAGTTCGCAGCTGGTCTTGGTGTCCCGGTTGGTATCACTGACAA
CTTCTTCGATCTCGGTGGTCACTCGGTCATGGCTACTAAGCTAGCTGTGC
GAATTGGCCGTCGTCTTGGTACGGCGTCACAGTCAAGGACATCTTCGAT
TACCCTGTGCTTTTCCAATGGTGAAGAAGTTGGAGTCTTCGCATTCCAA
GAGCTACGAGGAGTCTGGCGACGATATCCAGATGGTCGATTACACTGCAT
TCCAGCTCCTCGGTCTGGAGGACCCCAAGACTTTGTTCAGTCCCAGATT
CGGCCTCAACTGGACTCCTGCTACGGCACCATCCAGGATGTCTACCCGTC
TACGCAGATGCAAAAGGCCTTCCTCTTCGATCCCACGACCGGCGAGCCCC
GAGGTCTTGTGCCTTTCTATATCGACTTCTCCAGCAATGCAGATGCCGAG
ACCCTCACCAAGGCTATCGAGCTCTAGTTGACAAGCTCGATATGTTCAG
AACTGTCTTCCTGGAGGCCGCAGGCGATCTGTACCAAGTTGTCGTTGAGC
ACCTCAACTTGCCTATTGAGACCATCGAGACTGAGAAGAACGTCAACACT
GCAACCGGTGACTACCTGGATGTTCATGGAAAGGACCCTGTCCGTCTAGG
CCACCCGTGCATCCAATTCGCCATCCTGAAGACTGCCTCCTCTGTACGTG
TTCTCCTGCGAATGTCCCACGCTCTGTATGATGGTTTGAGTTTGAGTAC
ATCGTCCGTGGTCTCCACGTTCTCTACAGCGGTAGAAACCTCCCCCGACC
AACACAGTTTGCGCGATACATGCAGTATGCTGCACACAGTCGTGAAGAAG
GTTATCCCTTCTGGCGCGAGGTTCTGCAGAACGCGCCCATGACAGTTCTA
CACGACACCAATAACGGTATGTCTGAGCAAGAGATGCCAGCCTCCAAGGC
GGTACACCTGTCAGAGGTCGTCAACGTTCCAGCGCAAGCTATTCGAAACA
GTACCAACACCCAAGCGACCGTCTTCAACACCGCCTGTGCCCTTGTCCTA
GCCAAGGAATCCCGCTCACAGGATGTCGTCTTCGCCCTATTGTCTCTGC
TCGACAAGGTCTACCAGTCGTCGGTAGGACATTATCGGCCTCTGCACAA
ACGCCGTGCCCGTCCACGCACGCCGTCGACGATGGAAACCCCCAACGCATC
ATCCGCGACCTACGCGACCAATACCTCCGCACTCTGCCCTTCGAATCGCT
TGGCTTCTAGGAAATCAAGCGTAACTGCACGGACTGGCCTGAAGAATTGA
CCAACTTCTCTGTCTGCGTGACGTACCACAACTTCGAGTACCACCCCGAG
AGCGAAGTTGACAACCAAAAGGTTGAGATGGAGTTTTGGCAAAGTATGT
```

Figure 26 (Cont.)

TGAGTTGAGTGAAAACGAGCCGCTGTACGATCTTGCTATTGCGGAGAGG
TTGAGGCGGATGGAGTTAACCTGAAGGTCACTGTTGTTGCAAAGGCAAGG
CTTTACAATGAGGCGAGGATTAGACATGTGCTTGAGGAAGTTTGCAAAAC
TTTCAATGGTTTGAACGAGGCTTTGTAG

Figure 27

Seq ID No. 2

PF/Beauvericin Chimeric Synthetase:

>PF/Beauv

ATGTCAAACATGGCACCACTCCCTGCGATGGGCGTTGAGTAGCAAGCCCT
ATCACTTTCATGCCCCTTACTCCCTCATGACGATGAGAAACGCTCAGACA
ACCTTTACGAGCAAGCAACTCGGCACTTCGGCTTGAGCCGAGACAAGATC
GAAATGTCTTACCATGTACTTCCTTCAATGTGATGTCATACATTGCGC
CGTCGACGATCGCCGGCATGCTATCCGTCACGTCCTCTATGATATCCCA
ATACAGTGGACATCCAGCGTTTAGCCCCACCCTGCAAGAGGTTGTGCGG
CAGACACCAATCTTGAGGACCGGCATCTTTACATCAGAAACCGGCGACTC
TTTTCAGATCGTCTTGAAAGAAGGCTGCTACCGTGGATGTACGCGACAT
GTCTCGGCATGAAGGGGCAGTGATACAAGATGAAGCAGTCGCCGCTATG
ACTGGACCGCGTTGCAATCGATATGTCGTCCTGGAGGACCCGAGTACGAA
GTAAAGGCTGCTCATCTGGACATTCAGCCATGCTTTAGTGGATTATACAG
TCCAGGAACGCATCCTTCAGCGGGTTCTCACAGTATACGACGGCCGGAC
GTCGAGTGCCCTCGCATCAAGGATACAGAACATGTCTCTCGGTTTTGGCA
ACAACACTTTGAGGCTTAGATGCCCTCGTATTTCCCCTTCTACCATCTC
ACCTAACTGTGTGCAATCCCAATGCGCCGCAGAACATCATATCTCATAC
ACGGGACCAGTCCAGAGGAACTGGTCCCATACAAGTATCTGTCGGGCTGC
ACTCGCAGTTCTTCTATCTCGCTTTCACACTCTTCGGAGGGCCCTCTTCG
GTGTTGTGACAGAACAATCTCACAATTCCGAGGACCAAAGACGGTCAATT
GATGCCCCGCAAGGACAGTAGTGCCTATCCGCGTCCTTTGTGCCCCAGA
TCAATATGTGTCGGATGTCATTGGGCATCACCGCACAGAACACGCCA
TGCTCGGGTTTGAGCAGGCTGGACTTCGCAATATCTGCCCTACCGGAGAC
GACGGGTCTGCTGCTTGTGGATTCCAGACCGTGCTACTGGTGACTGACGG
TGATGCTCCCAAGACCCCTGGGAGTGTACTTCATCGAAGTGTAGAAGAAT
CGGATAGATTCATGCCCTGCGGTAATCGTGCCCTTCTGCTCGACTGCCAG
ATGGCTGGCAACTCGGCATCCCTAGTCGCACGATATGATCATAATGTGAT
CGACCCACGCCAGATGTCTCGCTTCCTGCGACAGCTAGGATACCTGATCC
AACAATTCATCATCACGTCGATCTGCCTCTGGTCAAAGAACTGGACGTC
GTCACGGCGGAGGATTGTCCGGAAATCAGAAATGGAATTCAGAACGCCT
AACAATGCAAGACGCCTTAATCCACGACACCATATCCAAGTGGGCTGCTG
GCGATCCCAACAAAGCTGCAGTTTTCGCTTGGGATGGGAATGGACATAC
GCCGAGCTAGACAACATATCCTCCCGGTCTCGCCGTGTATACCAATCCCT
GGACTTGAGACCAGGACAAGCAATACTCCCACTCTGCTTCGAGAAGTCAA
AATGGGTCGTCGCCACAATTCTCGCCGTCCTCAAAGCCGGTCGGGCATTC
ACACTCATGGACCCGTGCGACCCCTCGGCAAGGATGCCTAGGTCTGTA

Figure 27 (Cont.)

```
GCAGACCTCCGCCACAGTCGCTCTCACCTCCAAACTCCACAACACCACCT
TACGTTCCGTCGTTTCCCGGTGCATTGTGGTCGACGACGACCTCCTTCGG
TCCTTACCCCGCGCCGATGGCCCGCTTAAAGGCCACCGTGAAGCCACAGGA
CTTGGCCTATGTTATTTTCACATCTGGCAGCACAGGAGAGCCGAAAGGCA
TCATCATCGACATCGGCGTTCGTGTCGTGTGCTATGAAATTTGGCCCC
GCGCTCGGAATGGATGAGCACACGCGCGCTCTTGATTCGCCTCATATGC
GTTTCGCGCTTGTCTGGTAGAAGTTGTGACAGCTCTGATGCACGGCCGCT
GCGTCTGCATCCCTTCCGATGACGATCGCTTGAACAATGTACCGGAGTTC
ATCAAAAGGGCCCAGGTGAACTGGGTGATACTCACTCCGTCGTATATCGG
GACATTCCAGCCGGAAGATGTCCCTGCACTACAAACACTGGTATTGGTTG
GAGAACCTATCTCAGCGTCTATTCGGGATACCTGGGCCTCCCAGGTTCGA
CTCCTGAATGCCTACGGTCAGAGTGAAAGCTCAACTATGTGTAGCGTCAC
GGAAGTCAGCCCGCTCTCCTCGAACGAACAATATCGGTCGCGCTGTAG
GCGCACGATCCTGGATCATTGATCCCGACGAGCCTGATCGTCTTGCTCCA
ATTGGCTGCATTGGAGAGCTAGTGATCGAAAGTCCGGGCATTGCGCGCGA
CTATATCATCGCGCCGCCGCCGGACAAGTCCCCTTTCTCCTAGCACCTC
CGGCCTGGTATCCAGCCGGGAATTATCCAACGCCTTTAAAATTTACAAG
ACTGGAGATCTCGTGCGTTATGGACCTGACGGCACCATCGTCTGCCTGGG
ACGCAAAGATTCGCAAGTGAAGATCGAGGGCAGCGCGTAGAGATCGCG
CAGTGGAAGCCAGTCTACGACGACAACTACCTAGTGACATCATGCCCGTG
GCCGAAGCTATCAAACGCTCGGATTCGTCAGGCAGCACAGTCTTGACTGC
CTTCTTGATAGGGTCATCTAAGAGTTTATCTGCGGCAGATGCCGTTATCT
TGGATCACGGTGCTACCAACGAGATAAACGCGAGTTGCACAAATCCTTT
CCCCAGCATTCCGTTCCATCCTATTATATCCACATGGAAAATCTTCCTCG
AACTGCCACCGGCAAAGCGGACAGGAAATGCTTCGATCTATTGCTAGCA
AGCTATTGGGGAATTGTCTCAGAACGTGACATTCAACCGATTGAGAAG
CACGATGCCCAGCAACTGGTATAGACGTCAAGCTGAAGGAGCTTTGGTT
TCTGAGCTTGAATCTTAATCCCAACTCTCAAGATGTCGGAGCGAGTTTCT
TTGACTTAGGCGGAAATTCCATTATCGCCATCAAATGGTAAACATGGCG
AGGTCAGCTGGATAGCACTGAAGGTATCCGACATATTCCAGAATCCCAC
GCTTGCTCGTCTTCAGGCCGTGATGAGCGGCGATTCTACGCCCTCGACCA
TCACCACGCCCTTTCCGCCCATTCCGCCCTCGACTTGGGACGGACCCGTT
GAGCAGTCTTGCTCTCAAGGTCGATTGTGGTTCTTCGACCAGCTGGATAT
TGGAGCTGTATGGTACCTGATACCTTATGCCGTTCGCATGCGGGAGCTC
TCAACATTGACGGCTCTACGTGCTGCTCTGCTGGCGTTGAGCAGCGACAC
GAGACCCTGCGGACGACCTTTGAGAACGAAAACGGTGTAGGAGTGCAGAT
TGTTCACCAAAGACTTGCCAAGGAGCTGAAAATTATCGATGCGTCGTCCC
ACGGCGATGACGGCTACCTCCAGCCACTTGAGCAGGAGCAGACCACTCCA
```

Figure 27 (Cont.)

TTCGATCTGACTTGTGAGGCGGGCTGCAGGGCATCACTCATCTGCCTCGG
CGAGGACAATCATGTCTTGTCTATTGCCATGCATCACATTGTCTCCGATG
GCTGGTCCATTGACGTGCTGGCGAAGAACTAGGCCAGCTTTACGGCAGCG
GTTTTGCATGGCGACGAGCATCCTCTGTCGGCCGTGAGCCCGCTCCCCAT
ACAGTATCGAGACTTTTCCATGTGGCAGAGACGTCAACAGGTCGCCGAGC
ATGACAGACAGCTTCAATACTGGCGGAACAGCTCGCAGACTGCTCGCCCG
GCCAAGCTGCCCACCGATTTCCCCGACCACCCTTGCTGTCCGGCGACGC
TGGCAGCGTACCGGTGGAGATTCGGGGAGCTGTTCCAAAAGCTGCACA
GGTTCTGCAACGTGACCAGCACGACCCCGTTTGCCGTGCTTCTGGCCGTG
TTTGTGCTGCGCATTACCGACTCACCGGGTCGACGACGCCGTCGTGGG
CACGCCCATTGCCAACCGGAACCGGCCCGAGCTGGAGCGCCTGATTGGTT
TCTTTGTCAACACGCAATGTATGCGCATCACCGTGGACGATGATGATACA
TTGAGGGCTTGGTGGCCAAGTCCGTAGGACAACGACTGAGGCTTTTGA
AAACGAAGATGTCCCCTTTGAAGCGTCGTGTCCGCCATGCTACCGGCAG
GAGGAGGATCCAGAGATTTGTCCCAGACGCCCCTGCACAGCTCATCTTT
GCCGTGCACTGCAAGAAATCTAGGCAAGTTGAGCTAGAGGTCTCGA
GTCGGAACCTGTTGCCGAACAAGGCATATACGCGCTTTGACGCTGAATTTC
ACCTGTTCCAAACTGCTGACGGATTAAACGGCTACTTGAACTTTGCCGCG
GAATTGTGCAGCTAGAGACGATGCAAATGTCGCAGCGGCTTTCTTACA
GATTCTACGCCATGGACTGGAGCAGCCTAAATCCTTGATATCCGTTTGC
CGCTTACTGACGGGTTAAAGGAGCTCGACAGCATGGGCCTCTTGAAGATT
CATCGGGGCTTGAATATCAGCGAGACTCTAGCCTAGTCGACATCTTCCG
CAGCCAGTTGCTACTTGTCCTGATACAATTGCCGTCATTGACTCATCAG
CACGTCTGACGTATGCTCAGCTGGACCATCAGTCCAACCTACTCGAGGCC
TGGATTCGCCGCAAAGGCTTGCCGGCCGAATCATTGGTTGGCGTGCTTTC
ACCGGCGGTCCTGCGAGACAATGATCGCCTTTCTTGGTATTCTCAAAGCAA
ACCTGGCATATCTGCCGCTTGATCCAAATCCCCTGTCTCTCGTATGAGG
GACGTCCTGTCCGATTTACCAGGTCACACAATCATCCTGCTTGGCTCCGA
CGTGGCCGCCCCGACCGTGAGCTACCTTGTTGCAGCTCGTACGCATTT
CTGACGCCTTGAAATCTGGTGCAAGCGCAGTCAATGGCAGTGAGACGACA
GACTTGTCGGCTCCGTCGGCGAACAGTCTTGCATACGTTTTGTACACGTC
AGCGTCGACTGGCCGACCAAAGGGAGTCATGGTTGACCACCGTGCTATTC
TACGGCTTGTGCAGCGCGGCGTGATACCAAACTTCCCCCGTTGCCAGGA
GCAATCATGGCACATCTCTTCAATACCGTCTTTGACGGCGCGACCTATGA
AATTTTTCTCATGCTTTCGAACGGCGGCACGTTGGTCTGCATTGACTATC
TGACCACATTGAGCCCCAAAGCACTCGAAACCGCTCTTCCTGAGAAGGA
ATCAACTGTGCAATCATGACACCAGCGCTGCTTAAGCTGTATCTAGCCAA
TGCCCGCGATGGCTTAAAGGGACTCGACATGCTCATGGTCGCTGGAGACC

Figure 27 (Cont.)

GGTTCGATCCGCAGGACGCAGTCGAGCCACAGACTCTGGTCCGCGGTGAC
TGCTACAAGGCCTACGGCCCGACCGAGAATGGAGTCATGAGTACTCTGTA
CAAAATGATACAAGTGACTCCTTCATCAACGGCGTCCCTCTAGGTCGCG
CTATAGACAACTCTGGAGCCTACATTACCGACCCAAATCAGCAGCTTGTC
GGCCCGGCGTTTTGGGAGAGCTCATCGTCACCGGAGACGGGCTCGCTCG
GGCGTACACGGACCCAGTACTCGACAGAGACCGATTCGTACAAGTCGTCA
TCAACGGCGAGTCTGTCAGAGCATATCGACCGGAGACCGCATGCGCTAC
CGCGCAGGCCAAGATTGTCTTTTCGAATTCTTTGGACGCATGGACTTTCA
ATTCAAGATTCGAAGCAACCGCATCGAGTCGGCCGAGGTGGAAGCTGCCA
TTCTCAGTCATCCTCTGGTTCGCGATGCAGCCATTGTTGTTGTTGGTGTC
CAAGAGGAACAAGAGCCAGAATGGTTGGGTTCGTTGTTGCTGCTGACGA
TGCCGTTGAGCAAGAGGCCACAGACAACCAGTGGAGGGTTGGCAAGAAC
TGTTTGAGAGTAGCATGTGCAACGGCATCGATGTAATAAGCTCGTCTGCT
CTCGGCAAGGACTTTACAGGGTGGACGTCCATGTACGATGGAAGTGAAAT
CGACAAGTCGGAGATGCAGGAGTGGCTCGACGATACGATACATACTCTAC
GCCACGGTCATGTACCGGCGCATGTCCTGGAGATTGGAACCGGTACAGGT
ATGATCTTGTTTAACCTCGGCTCTGTTGAGAGCTACGTAGGTCTGGAACC
CACCAAGTCCGCGGTCGAGTTTGTCAACAAGGCCATCAAGACCCTGCCAA
ATCTCGCAGGAGGCCCAGGCTTCACACTGGCACCGCTACAGATATCGAC
CAGCTGAGCGGACTGCGGCCAGACCTTGTTAGACTAAACTCTGTGGTTCA
GTACTTTCCCACAGTAGAATATCTGACACCGGGTTGTGGACGCTCTGGTCC
GGATACGCGGCGTCAAACGTCTCTTCTTTGGTGATGTGCGATCACAGGCG
CTACACAGACAGTTTCTTGCTGCCTGTGCGATGCACGCACTAGTCAAGGC
GGCGACCAGGACGACGTGCGGAGATACATGGCAGAGCGGGTGGAGCGGG
AGGAGGAGCTGCTCGTCGAGCCAGCCTTTTTCACAGCACTCATGAACCGG
CATCCGATCGATCCAGCACGTCGAGATTCTGTCCAAGAATATAAGGGC
CACAAATGAGCTGAGCGCATACCGTTATGCAGCCGTCGTCCATCTACGTG
ATCCGGAGTCTGCGGCGCGGCCGGTGTATCCGATTGCGGCAGACGACTGG
GTCGACTTTCAGGCCTCCCAGATGCGCAGCGACGTCCTTCGAGAATACGT
GGCGTCTCGGCCGGTGCCGATACCGTGGCTGCTGCAATATTCCGTACG
AAAAGACCATCTTTGAGAGACTGATTGTCGAGTCACTTGATGACAACACC
CGCACTGACGCGCCACAGAGTAGGCTGCATGGCAGGTGACTAGATGGCGC
GCCCTGGATATCCGCCGTCCGTTCCGACGTCGAGAGCCGGGTATCCGTCT
CCGTGCCCGGACCTTGTGCAGCTAGCCGCCGAGTCTGGCTTCCAGGTACAG
GTCAGTGCCGCACGACAGTGGTCGCAGAGCGGCGCGCTGGACGCCGTCTT
CCACCGGCGCCACGCGTCGTCCTCTCAGCCGACTATGCGTACACTCTTCG
AATTCCCCGACGACAATGCACTGCGAGCTTCGGCTACCCTGACGAACCGG
CCGCTGCAGCGGCTGCAGAGACGTCGCGTCGCGGCGCAGATTCGCGGAACG

Figure 27 (Cont.)

```
GCTGCAGACGCTGGTGCCGTCGTACATGATTCCTGCCAAGATTGTCGTGC
TGGACCAGATGCCTCTCAACGCCAATGGCAAGGTCGACCGGAAGGAGCTG
GCTCGTAGAGCCCGGACGACGACGATGACGAAGAAAAAGAAGCCGCAGCG
ATTGGCGTCGGAGCCAGCTTGTCCAATCAGCGACATTGAGGTTGCACTGT
GCGAGGAGGCCACGGCAACGTTTGGAATGCAAGTCCGGCATCAGCGATCAC
TTTTTCAAACTCGGCGGTCATTCTCTGCTTGCTACAAAACTCATATCCCG
CGTCGGCGACAGACTGAAAGCGCGCCTGACGGTCAGGATGTCTTTGATC
ACCCAATCTTTTCCGAGCTTGCGATTGTCATACGCGAGGGCTGCAAAAC
GTCGTGCCCGTGGCTTTGAATGCTGGTGGACAAGCGAAGTAAGGGTCGGC
GGCAGTAGTACCGCCGGCAATGAAATGAAACGATGCTGTGTGAGGAGT
TTGCCAATGTCCTTGGCATGGATGTCGGAGTCACGGACAACTTTTTTGAC
CTCCGTGGCCATTCGCTCATGGCGACAAAGCTGGCAGCGCGGATTGGGCG
TCGATTGAATGCTGCGATATCAGTGAAGGAGGTCTTTGAACAGCGATTG
TGTTTCAGCTCGCCAATTCCCTAGAGCTGGGTCAGTTGGAGAGCGACAGA
GTAAGCACACAATGTTGGCCGATTACACTGCGGTTTCAACTCTTGTCTGT
TGAAGATTGCAGGCGTTTCTTCAAACGAGATAAGCCCTCAACTTGAAT
GTGCACATGGCGGTATCAAGATGTATATCCAGCCACGCATATGCAAAAG
GCGTTTTATGCGACGCGTCAACCGGACATCCCAAGCCTCTTGTGCCGTT
CTACATTGACTTTCCCCCGACTCAGACTGTTCTACTCTGGTCGAGGCGT
GCTCATCTCTGGTGAAGCGTTTCGACATGTTCAGGACAGTGTTCGTGGAA
GCTGCAGGCGAACTGTATCAAGTCGTTTTAGAGCACTTTGATCTACAGAT
TGATGTCGTCGAGACGGAGGAAAACGTCCACGCGGCGACGACGATTTCG
TGGACAGAATCTTGGAGGTGCCCGTCCATCTGGGCTACCGCTGATACAA
TTCACCATTCTCAAGCAGGCGTCTTCAGTACGAGTCTTGCTTTGTCTTTC
TCACGCCCTCTATGATGGCTTGAGTTTGGAGCACGTCGTGCGCGATCTGC
ACATGCTTTACAAGGCCGGTCCCTGCTGCCAGTGAATCAGTTCTCACGG
TACATGCAATACATGGACCACACGCGCAAAGCCGCTGTGACTTTTGGCG
CGATGTCATACAAGATACGCCAATCACTGTCCTCGGCCATGTCGATGCTG
GTGGCCGTGAGCTAGAAGTGGAAGCAGCGCGGACATTGCACGCGACAAAG
ATTATTAGCATTCCTCTGCAGGCTGTCCGCAGCAGTATCATTACGCAGGC
GACAGTCTTCAACGCTGCCTGTGCTCTCGTGCTGTCTCGAGAAACCGGCG
CCAACGACGTCGTGTTTGCCCGATCGTCTCGGGGCGGCAACGCCTGCCC
GTGAGCTGGCAAAACATTGTCGGGCTGTGTACCAATGCCGTACCGGTGCG
CGCCCGGATCATCGACGACGACGACGACAACCACCGCCAGATGCTCCGCG
ACATGCAAGACCAGTACCTCCTGAGCCTGCCGTTTGAGACGCTCGATTTT
GACAGGGTCCGACGCAGCTGCACAAACTGGCCGCGACGGCCAACAACTA
CGCCGTGCTGCCTGACGTACCACGACTTTTCATACCACCCAGGAGCGAGA
TGGAGCAGCAGCGCGGTCGAGATGGGCGTGCTGGCCAGAAAGGATGCGCTG
```

Figure 27 (Cont.)

CTCAAGGAGGAGCCCGTGTACGACCTGGGCATCGCAGGAGAGGTTGAGCC

GGATGGCGTGCACTTGCAAGTTACCGTGGTCGCAAGACGAGGCTGTTTA

GTGAAGAGAGGGCCGCATACCTGATGGAAGAGGTGTGTAGACTGTTTGAG

AGTCTAAACTCGGCTTTGTGA

SEQUENCE LISTING

```
<160> NUMBER OF SEQ ID NOS: 40

<210> SEQ ID NO 1
<211> LENGTH: 9378
<212> TYPE: DNA
<213> ORGANISM: Fusarium oxysporum

<400> SEQUENCE: 1
atgtcaaaca tggcaccact ccctacgatg ggcgttgagc agcaagccct atcactttca      60 tgcccttac tccctcatga cgatgagaaa cactcagaca acctttacga gcaagcaact     120
cggcacttcg gcttgagccg agacaagatc gaaaatgtct taccatgtac ttcctttcaa     180
tgtgatgtca tagattgcgc cgtcgacgat cggcggcatg ctatcggtca cgtcgtctat     240
gatatcccca atacagtgga catccagcgt ttagccgcag cctggaaaga ggttgtgcgg     300
cagacaccaa tcttgaggac cggcatcttt acatcagaaa ccggcgactc ttttcagatc     360
gtcttgaaag aaggctgcct accgtggatg tacgcgacat gtctcggcat gaaggggggca    420 gtgatacaag atgaagcagt cgccgctatg actggaccgc gttgcaatcg atatgtcgtc     480
ctggaggacc cgagtacgaa gcaaaggctg ctcatctgga cattcagcca tgctttagtg     540
gattatacag tccaggaacg catccttcag cgggttctca cagtatacga cggccgggac     600
gtcgagtgcc ctcgcatcaa ggatacgaaa catgtctctc ggttttggca acaacacttt    660
gaaggcttag atgcctccgt atttcccctt ctaccatctc acctaactgt gtgcaatccc     720
aatgcgcgcg cagaacatca tatctcatac acgggaccag tccagaggaa gtggtcccat     780
```

```
acaagtatct gtcgggctgc actcgcagtt cttctatctc gctttacaca ctcttcggag      840
gccctcttcg gtgttgtgac agaacaatct cacaactccg aggaccaaag acggtcaatt      900
gatggccccg caaggacagt agtgcctatc cgcgtccttt gtgccccaga tcaatatgtg      960
tcggatgtca ttggggcaat caccgcacac gaacacgcca tgcgcgggtt tgagcacgct     1020
ggacttcgca atatccgccg taccggagac gacgggtctg ctgcttgtgg attccagacc     1080
gtgctactgg tgactgacgg tgatgctccc aagacccctg ggagtgtact tcatcgaagt     1140
gtagaagaat cggatagatt catgccctgc gctaatcgtg cccttctgct cgactgccag     1200
atggctggca actcggcatc cctagtcgca cgatatgatc ataatgtgat cgacccacgc     1260
cagatgtctc gcttcctgcg acagctagga tacctgatcc aacaatttca tcatcacgtc     1320
gatctgcctc tggtcaaaga actggacgtc gtgacggcgg aggattgtgc ggaaatcgag     1380
aaatggaatt cagaacgcct aacaatgcaa gacgccttaa tccacgacac catatccaag     1440
tgggctgctg gcgatcccaa caaagctgca gttttcgctt gggatgggga atggacatac     1500
gccgagctag acaacatatc ctcccgtctc gccgtgtata tccaatccct ggacttgaga     1560
ccaggacaag caatactccc actctgcttc gagaagtcaa aatgggtcgt cgccacaatt     1620
ctcgccgtcc tcaaagccgg tcgggcattc acactcatcg acccgtgcga cccctcggca     1680
aggatggccc aggtctgtca gcagacctcc gccacagtcg ctctcacctc caaactccac     1740
aacaccacct tacgttccgt cgtttcccgc tgcattgtgg tcgacgacga cctccttcgg     1800
tccttacccc gcgccgatgg ccgcttaaag gccaccgtga agccacagga cttggcctat     1860
gttattttca catctggcag cacaggagag ccgaaaggca tcatgatcga acatcggggg     1920
ttcgtgtcgt gtgctatgaa atttggcccc gcgctcggaa tggatgagca cacgcgcgct     1980
cttcaattcg cctcatatgc gtttggcgct tgtctggtag aagttgtgac agctctgatg     2040
cacggcggct gcgtctgcat cccttccgat gacgatcgct tgaacaatgt accggagttc     2100
atcaaaaggg cccaggtgaa ctgggtgata ctcactccgt cgtatatcgg gacattccag     2160
ccggaagatg tccctggact acaaacactg gtattggttg gagaacctat ctcagcgtct     2220
attcgggata cctgggcctc ccaggttcga ctcctgaatg cctacggtca gagtgaaagc     2280
tcaactatgt gcagcgtcac ggaagtcagc ccgctctccc tcgaaccgaa caatatcggt     2340
cgggctgtag gcgcacgatc ctggatcatt gatcccgacg agcctgatcg tcttgctcca     2400
attggctgca ttggagagct agtgatcgaa agtccgggca ttgcgcgcga ctatatcatc     2460
gcgccgccgc cggacaagtc ccccttctc ctagcacccc cggcctggta tccagccggg     2520
aaattatcca acgcctttaa attttacaag actggagatc tcgtgcgtta tggacctgac     2580
ggcaccatcg tctgcctggg acgcaaagat tcgcaagtga agatccgagg gcagcgcgta     2640
gagatcagcg cagtggaagc cagtctacga cgacaactac ctagtgacat catgcccgtg     2700
gccgaagcta tcaaacgctc ggattcgtca ggcagcacag tcttgactgc cttcttgata     2760
gggtcatcta agagtttatc tgcggcagac gccgttatct tggatcacgg tgctaccaac     2820
gagataaacg cgaagttgca gcaaatcctt ccccagcatt ccgttccatc ctattatatc     2880
cacatggaaa atcttcctcg aactgccacc ggcaaagcgg acaggaaaat gcttcgatct     2940
attgctagca agctattggg tgaattgtct cagaacgtga catctcaacc gattgagaag     3000
cacgatgccc cagcaactgg tatagaggtc aagctgaagg agctttggtt tctgagcttg     3060
aatcttaatc ccaactctca agatgtcgga gcgagtttct ttgacttagg cggaaattcc     3120
```

```
attatcgcca tcaaaatggt aaacatggcg aggtcagctg ggatagcact gaaggtatcc   3180
gacatattcc agaatcccac gctcgctggt ctcaaggcta ttgtcattgg tacttcgctg   3240
ccatacagcc ttattcccaa ggttacccgc caaggccctg ttagcgagca gtcttatgcg   3300
caaaacagaa tgtggttcct ggatcagttg tctgagggtg cttcatggta tctgattcct   3360
ttcgctgtgc gcatgcgagg tccggtggat gttgatgcgt tgacgcgtgc tttgctcgct   3420
cttgaacagc gtcatgagac actacgaact acatttgaga accaagatgg tgttggagtc   3480
cagatcatcc atgatagact ctccaaagag ctacaagtca tcgatgcctt ggatggtgac   3540
gagggtggtc tcaagacact ctacaaagta gagaccacca cattcgacat cacatccgaa   3600
gcaggctgga gctcaaccct catccgcctc ggcaaagacg atcacattct gtctatcgtc   3660
atgcaccaca tcatctccga cggctggtcc atcgacgttc tccgccgcga actcatccaa   3720
ctctacgccg ccgctctgca gggcaaggat ccttcctccg cactaacccc cctacccatc   3780
cagtacagcg acttcgccgt gtggcagaag caggaggccc aagcagctga gcacgagagg   3840
cagctccagt actggaagaa gcaactcgca gatagttcac ctgccaagat ccctaccgac   3900
ttccccgtc cagatctcct gtccggtgac gcaggcgttg tgcccgttgc catcgacggc   3960
gagctgtatc agaaactaag gggcttctgc aacaagcaca acagcactgc cttctccatc   4020
ctgctcgctg ctttccgcgc ggcgcattac cgtctcacag ccgttgacga cgccgtgatc   4080
ggcatcccca ttgcaaaccg taaccgctgg gagctggaga acatgattgg tttctttgtc   4140
aacacgcagt gtatgcgcat cgccgttgac gagacggata catttgagag tctggtgcgc   4200
caggtcagat ctaccactac agctgcgttt gcgcacgagg atgtcccctt cgagcgtgtc   4260
gtttcagcgc ttcagcctgg ccatagagat ctctcgcgaa caccgctggc acagataatg   4320
tttgctgttc actcgcagaa ggaccttgga cgtttcgagc tggagggtat ccagtctgag   4380
cctatcgcca gcaaggccta caccagattc gatgtcgagt tccatctgtt ccaacaggca   4440
gacggactga agggcagttg caactttgcc acagatctct tcaagcccga aactatccag   4500
aatgttgtca gcgtgttttt ccagattcta cgccatggcc ttgaccagcc tgagacgtgt   4560
atctcggttc ttccactgac tgatggagtc gaggagcttc gcaggttgga tctgctggaa   4620
atcaagagga ctaactaccc tcgcgattcg agcgtggtag atgtcttccg cgaacaagct   4680
gccgccaacc cagaggttat cgctgttacc gactcatctt ctcgtctgac ttatgcagag   4740
ctggacaata agtctgagct gctctcacga tggcttcgac gacgtaactt gacgccagag   4800
acgctggtca gtgttcttgc tccccggtct tgcgagacta tcgttgccta tgttggtatc   4860
ctcaaggcga acctggcgta tcttcctctt gacgtgaggt ccccggtgac tcgtatgaag   4920
gacatcttgt cgagcgtgtc tggaaacacc atagttctta tgggctctgg ggtagaggat   4980
cctggctttg acttaccgca actagagctc gtacgcatca ccgacacttt cgatgagacc   5040
atcgaggacg tgcaagactc tccccaaccg tctgccacaa gcctcgccta cgtcgtcttc   5100
acatccggtt caactggtaa acccaagggc gtcatgatca agcaccgggc cattgtgcgt   5160
ctcgtcaaga gtgacaactt tcctggcttc ccctccccg ctcgcatgtc aaatgtcttc   5220
aaccctgcct tcgacggagc catctgggag atcaactgga tgctcctgaa cggcggaaca   5280
gtcgtctgca tcgactacct gaccacccctg gacggcaaag agctcgctgc tgtgttcgcc   5340
aaagagcgcg tcaacgccgc cttcttcgca cctgcgatgc tcaagcttta cctcgttgat   5400
gcgcgcgagg ctttgaagaa tcttgacttc cttattgttg gaggtgagag gttcgatacc   5460
aaggaagccg tggaggccat gccgcttgtg agaggcaaga ttgccaatat ctatggtccg   5520
```

```
actgaggctg gaataatcag cacgtgctat aacatcccca aggatgaggc ttacaccaat    5580
ggtgttccca ttggtggaag tatctacaac tctggtgcct acgtcatgga tcctaaccag    5640
caacttgtcg gccttggcgt catgggagag cttgttgtta ccggagacgg tgttggtcga    5700
ggctacacta accccgagct caacaagaac cgcttcatcg acatcaccat cgagggcaag    5760
actttcaagg cttaccgtac tggtgaccgg atgcgtgcac gagtaggcga cggtctcctt    5820
gagttcttcg gccgcatgga caaccagttc aagatccgcg caaccgtat cgaagcaggg     5880
gaagttgagt ctgccatgct cagcctcaag aatgtcctta acgccgccat tgtcgtccgc    5940
gggggcggag aagatgaagg gccactcgag atggtcggat tcatcgtcgc ggacgacaag    6000
aatgatacca cggaggagga agagacaggc aaccaagttg agggctggca ggaccatttc    6060
gagagtggta tgtactcgga tatcagcacc gccgtggacc aatctgccat tggaaacgac    6120
tttaagggct ggacttctat gtacgatggt aaggatatcg acaagggcga gatgcaggag    6180
tggttggacg acgctattca caccctgcat aacggccaga tccctcgcga tgtcctcgag    6240
atcggtaccg gtagtggtat gatcctgttc aacctcaacc cgggcctcaa cagctacgtt    6300
ggtcttgatc catccaagtc agcagtcgag ttcgtcaaca gagccgtcga gtcctctccc    6360
aagttcgcag gaaaagccaa ggtccacgtc ggcatggcca cagacgtcaa caaactcggc    6420
gaagtacacc ccgatctcgt ggtcttcaac tccgttgttc aatacttccc cacacccgag    6480
tatctcgccg aggtcatcga tggcctcatt gccatcccca gcgtcaagcg catcttcctt    6540
ggcgatatca gatcatatgc taccaacgga cacttcctcg ccgcacgcgc catccacacg    6600
ctcggcacca ataacaacgc caccaaggat agggtgcgcc agaagatcca ggagctggag    6660
gatcgagagg aagagtttct cgttgagcct gccttcttca ccactctgaa ggagcgacgt    6720
ccagatgttg tcaagcatgt tgagatcatc cccaagaaca tgaaggccac caacgaactc    6780
agcgcctatc gctacacggc tgttgtgcat ctgcgggatg aaacggacga acctgtgtat    6840
catattgaga aggatagctg ggttgacttt gaggcgaagc agatggacaa gacggctctt    6900
cttgaccacc tgcgcctctc caaggatgct atgagtgtgg cggttagcaa catcacctac    6960
gcccacactg cctttgaacg tcgtatcgtt gagtctctcg atgaggatag caaggatgac    7020
accaagggta cactcgatgg tgcagcctgg ctctcagcag ttcgctccga agccgaaaac    7080
cgcgcctcac tcaccgtccc cgacatcctg agatcgcca aagaggctgg tttccgagtt    7140
gaagtcagcg ctgctcgcca gtggtcccaa agtggtgctt tagacgcagt cttccaccac    7200
tttccaccct ccagcactga ccgcactcta atccagttcc ccacggacaa cgagcttcga    7260
tcatcactca ccctcgccaa ccgccctctc cagaagctgc agcgccgtcg tgccgctctg    7320
caagtccgcg agaagctcca gacgctggtc ccgtcttaca tggttcctcc gaatatcgtg    7380
gtgctggaca cgatgcctct caatactaac ggcaagatcg acagaaagga gcttacgcgt    7440
agagcacgaa cactgccgaa gcagcagact gcggcgcctg tgccggactt ccctatctct    7500
gatatcgaga tcacgctgtg cgaggaggca actgaggtct ttggaatgaa ggttgaaatc    7560
agcgatcact tcttccagct cggcggtcac tctctcctcg ctacgaaact catttctcgc    7620
atccagcacc gtctccatgt gcgggttact gtgaaggacg tattcgacag ccctgtcttt    7680
gccgatctgg cagtcatcat ccgtcaagga cttgctatgc agaaccctgt tgctgaagga    7740
caggacaagc aaggctggtc ctcgagagtt gcccctcgta cagaagtcga gaagatgctg    7800
tgcgaggagt tcgcagctgg tcttggtgtc ccggttggta tcactgacaa cttcttcgat    7860
```

-continued

```
ctcggtggtc actcgctcat ggctactaag ctagctgtgc gaattggccg tcgccttgat   7920
accgccatca cagtcaagga catcttcgac taccctgtgc ttttccaatt ggcgaagaag   7980
ttggagtctt cgcattccaa gagctacgag gagtctggcg acgatatcca gatggccgat   8040
tacactgcat tccagctcct cgatctggaa gacccccaag actttgttca gtcccagatt   8100
cggcctcaac tggactcctg ctacggcacc atccaggatg tctacccgtc tacgcagatg   8160
caaaaggcct tcctcttcga tcccacgacc ggcgagcccc gaggtcttgt gcctttctat   8220
atcgacttcc ccagcaatgc agatgccgag accctcacca aggctatcgg agctctagtt   8280
gacaagctcg atatgttcag aactgtcttc ctggaggccg caggcgatct gtaccaagtt   8340
gtcgttgagc acctcaactt gcctattgag accatcgaga ctgagaagaa cgtcaacact   8400
gcaaccggtg actacctgga tgttcatgga aaggaccctg tccgtctagg ccacccgtgc   8460
atccaattcg ccatcctgaa gactgcctcc tctgtacgtg ttctcctgcg aatgtcccac   8520
gctctgtatg atggtttgag ttttgagtac atcgtccgtg gtctccacgt tctctacagc   8580
ggtagaaacc tccccccacc aacacagttt gcgcgataca tgcagtatgc tgcacacagt   8640
cgtgaagaag gttatccctt ctggcgcgag gttctgcaga acgcgcccat gacagttcta   8700
cacgacacca ataacggtat gtctgagcaa gagatgccag cctccaaggc ggtacacctg   8760
tcagaggtcg tcaacgttcc agcgcaagct attcgaaaca gtaccaacac ccaagcgacc   8820
gtcttcaaca ccgcctgtgc ccttgtccta gccaaggaat ccggctcaca ggatgtcgtc   8880
ttcggccgta ttgtctctgg tcgacaaggt ctaccagtcg tctggcagga catcatcggc   8940
ccctgcacaa acgccgtgcc cgtccacgca cgcgtcgacg atggaaaccc ccaacgcatc   9000
atccgcgacc tacgcgacca atacctccgc actctgccct tcgaatcgct tggcttcgag   9060
gaaatcaagc gtaactgcac ggactggccc gaagaattga ccaacttctc tgtctgcgtg   9120
acgtaccaca acttcgagta ccaccccgag agcgaagttg acaaccaaaa ggttgagatg   9180
ggagttttgg caaagtatgt tgagttgagt gaaaacgagc cgctgtacga tcttgctatt   9240
gcgggagagg ttgaggcgga tggagttaac ctgaaggtca ctgttgttgc aaaggcaagg   9300
ctttacaatg aggcgaggat tagacatgtg cttgaggaag tttgcaaaac tttcaatggt   9360
ttgaacgagg ctttgtag                                                 9378
```

<210> SEQ ID NO 2
<211> LENGTH: 9471
<212> TYPE: DNA
<213> ORGANISM: Beauveria bassiana

<400> SEQUENCE: 2

```
atgtcaaaca tggcaccact ccctacgatg ggcgttgagc agcaagccct atcactttca     60
tgccccttac tccctcatga cgatgagaaa cactcagaca acctttacga gcaagcaact    120
cggcacttcg gcttgagccg agacaagatc gaaaatgtct taccatgtac ttcctttcaa    180
tgtgatgtca tagattgcgc cgtcgacgat cggcggcatg ctatcggtca cgtcgtctat    240
gatatcccca atacagtgga catccagcgt ttagccgcag cctggaaaga ggttgtgcgg    300
cagacaccaa tcttgaggac cggcatcttt acatcagaaa ccggcgactc ttttcagatc    360
gtcttgaaag aaggctgcct accgtggatg tacgcgacat gtctcggcat gaagggggca    420
gtgatacaag atgaagcagt cgccgctatg actggaccgc gttgcaatcg atatgtcgtc    480
ctggaggacc cgagtacgaa gcaaaggctg ctcatctgga cattcagcca tgctttagtg    540
gattatacag tccaggaacg catccttcag cgggttctca cagtatacga cggccgggac    600
```

```
gtcgagtgcc ctcgcatcaa ggatacagaa catgtctctc ggttttggca acaacacttt    660
gaaggcttag atgcctccgt atttcccctt ctaccatctc acctaactgt gtgcaatccc    720
aatgcgcgcg cagaacatca tatctcatac acgggaccag tccagaggaa gtggtcccat    780
acaagtatct gtcgggctgc actcgcagtt cttctatctc gctttacaca ctcttcggag    840
gccctcttcg gtgttgtgac agaacaatct cacaactccg aggaccaaag acggtcaatt    900 gatgccccg caaggacagt agtgcctatc cgcgtccttt gtgccccaga tcaatatgtg     960
tcggatgtca ttgggcaat caccgcacac gaacacgcca tgcgcgggtt tgagcacgct    1020
ggacttcgca atatccgccg taccggagac gacgggtctg ctgcttgtgg attccagacc   1080
gtgctactgg tgactgacgg tgatgctccc aagaccctg ggagtgtact tcatcgaagt    1140
gtagaagaat cggatagatt catgccctgc gctaatcgtg cccttctgct cgactgccag   1200
atggctggca actcggcatc cctagtcgca cgatatgatc ataatgtgat cgacccacgc   1260
cagatgtctc gcttcctgcg acagctagga tacctgatcc aacaatttca tcatcacgtc   1320
gatctgcctc tggtcaaaga actggacgtc gtgacggcgg aggattgtgc ggaaatcgag   1380
aaatggaatt cagaacgcct aacaatgcaa gacgccttaa tccacgacac catatccaag   1440
tgggctgctg gcgatcccaa caaagctgca gttttcgctt gggatgggga atggacatac   1500
gccgagctag acaacatatc ctcccgtctc gccgtgtata tccaatccct ggacttgaga   1560
ccaggacaag caatactccc actctgcttc gagaagtcaa aatgggtcgt cgccacaatt   1620
ctcgccgtcc tcaaagccgg tcgggcattc acactcatcg acccgtgcga ccctcggca    1680 aggatggccc aggtctgtca gcagacctcc gccacagtcg ctctcacctc caaactccac   1740
aacaccacct tacgttccgt cgtttcccgc tgcattgtgg tcgacgacga cctccttcgg   1800
tccttacccc gcgccgatgg ccgcttaaag gccaccgtga agccacagga cttggcctat   1860
gttattttca catctggcag cacaggagag ccgaaaggca tcatgatcga acatcggggg   1920
ttcgtgtcgt gtgctatgaa atttggcccc gcgctcggaa tggatgagca cacgcgcgct   1980
cttcaattcg cctcatatgc gtttggcgct tgtctggtag aagttgtgac agctctgatg   2040
cacggcggct gcgtctgcat cccttccgat gacgatcgct tgaacaatgt accggagttc   2100
atcaaaaggg cccaggtgaa ctgggtgata ctcactccgt cgtatatcgg gacattccag   2160
ccggaagatg tccctggact acaaacactg gtattggttg gagaacctat ctcagcgtct   2220
attcgggata cctgggcctc ccaggttcga ctcctgaatg cctacggtca gagtgaaagc   2280
tcaactatgt gcagcgtcac ggaagtcagc ccgctctccc tcgaaccgaa caatatcggt   2340
cgggctgtag gcgcacgatc ctggatcatt gatcccgacg agcctgatcg tcttgctcca   2400
attggctgca ttggagagct agtgatcgaa agtccgggca ttgcgcgcga ctatatcatc   2460
gcgccgccgc cggacaagtc cccctttctc ctagcacccc cggcctggta tccagccggg   2520
aaattatcca cgcctttaa atttacaag actggagatc tcgtgcgtta tggacctgac     2580
ggcaccatcg tctgcctggg acgcaaagat tcgcaagtga agatccgagg gcagcgcgta   2640
gagatcagcg cagtggaagc cagtctacga cgacaactac ctagtgacat catgcccgtg   2700
gccgaagcta tcaaacgctc ggattcgtca ggcagcacag tcttgactgc cttcttgata   2760
gggtcatcta agagtttatc tgcggcagac gccgttatct tggatcacgg tgctaccaac   2820
gagataaacg cgaagttgca gcaaatcctt cccagcatt ccgttccatc ctattatatc    2880
cacatggaaa atcttcctcg aactgccacc ggcaaagcgg acaggaaaat gcttcgatct   2940
```

```
attgctagca agctattggg tgaattgtct cagaacgtga catctcaacc gattgagaag      3000
cacgatgccc cagcaactgg tatagaggtc aagctgaagg agctttggtt tctgagcttg      3060
aatcttaatc ccaactctca agatgtcgga gcgagtttct ttgacttagg cggaaattcc      3120
attatcgcca tcaaaatggt aaacatggcg aggtcagctg ggatagcact gaaggtatcc      3180
gacatattcc agaatcccac gcttgctcgt cttcaggccg tgatgagcgg cgattctacg      3240
ccctcgacca tcacgacgcc cttttgccacc attccggcgt cgacttggga cggacccgtt      3300
gagcagtctt actctcaagg tcgattgtgg ttcctcgacc agctggatat tggagctgta      3360
tggtacctga taccttatgc cgttcgcatg cggggagctc tcaacattga cgctctacgt      3420
gctgctctgc tggcgttgga gcagcgacac gagaccctgc ggacgacctt tgagaaccaa      3480
aacggtgtag gagtgcagat tgttcaccaa agacttgcca aggagctgaa aattatcgat      3540
gcgtcgtccc acggcgatga cggctacctc cagccacttg agcaggagca gaccactcca      3600
ttcgatctga cttgtgaggc gggctggagg gcatcactca tctgcgtcgg cgaggaccat      3660
catgtcttgt ctattgtcat gcatcacatt gtctccgatg gctggtccat tgacgtgctg      3720
cggcaagaac taggccagct ctacgcagcg gttttgcatg gcgacgagga tcctctgtcg      3780
gccgtgagcc cgctccccat acagtatcga gactttccca tgtggcagag acgtcaacag      3840
gtcgccgagc atgacagaca gcttcaatac tggcggaaac agctcgcaga ctgctcgccg      3900
gccaagctgc ccaccgattt ccccgacca cccttgctgt ccggcgacgc tggcagcgta      3960
ccggtggaga tttcgggcga gctgttccaa aagctgcaca ggttctgcaa cgtgaccagc      4020 acgacccgt ttgccgtgct tctggccgcg tttcgtgctg cgcattaccg actcaccggg      4080
gtcgacgacg ccgtcgtggg cacgcccatt gccaaccgga accggcccga gctggagcgc      4140
ctgattggtt tctttgtcaa cacgcaatgt atgcgcatca ccgtggacga tgatgataca      4200
tttgagggct tggtacgcca agtccgtagg acaacgactg aggcttttga aaacgaagat      4260 gtccccttg aacgcgtcgt gtccgccatg ctaccggcag gaggaggatc cagagatttg      4320
tcccagacgc ccctggcaca gctcatcttt gccgtgcact cgcaagaaaa tctaggcaag      4380
tttgagctag aaggtctcga gtcggaacct gttgcgaaca aggcatatac gcgctttgac      4440
gctgaatttc acctgttcca aactcgtgac ggattaaacg gctacttgaa cttgccgcg      4500 gaattgttca agctagagac gatgcaaaat gtcgtcagcg tcttcttaca gattctacgc      4560
catggactgg agcagcctaa atccttgata tccgttttgc cgcttactga cgggttaaag      4620
gagctcgaca gcatgggcct cttgaagatt catcggggc ttgaatatca gcgagactct      4680
agcctagtcg acatcttccg cagccaggtt gctacttgtc ctgatacaat tgccgtcatt      4740
gactcatcag cacgtctgac gtatgctcag ctggaccatc agtccaacct actcgaggcc      4800
tggattcgcc gcaaaggctt gccggccgaa tcattggttg gcgtgctttc accgcggtcc      4860
tgcgagacaa tcatcgcctt tcttggtatt ctcaaagcaa acctggcata tctgccgctt      4920
gatccaaaat cccctgtctc tcgtatgagg acgtcctgt ccgatttacc aggtcacaca      4980
atcatcctgc ttggctccga cgtggccgcc cccgaccttg agctaccttg tttggagctc      5040
gtacgcattt ctgacgcctt gaaatctggt gcaagcgcag tcaatggcag tgagacgaca      5100
gacttgtcgg ctccgtcggc gaacagtctt gcatacgttt tgtacacgtc agggtcgact      5160
gggcgaccaa agggagtcat ggttgagcac cgtgctattg tacggcttgt gcagcgcggc      5220
gtgataccaa actttccccc gttgcgagga gcaatcatgg cacatctctt caataccgtc      5280
tttgacggcg cgacctatga aatttttctc atgcttttga acggcggcac gttggtctgc      5340
```

```
attgactatc tgaccacatt gagccccaaa gcactcgaaa ccgtcttcct gagagaagga    5400
atcaactgtg caatcatgac accagcgctg cttaagctgt atctagccaa tgcccgcgat    5460
ggcttaaagg gactcgacat gctcatggtc gctggagacc ggttcgatcc gcaggacgca    5520
gtcgaggcac agactctggt ccgcggtgac tgctacaacg cctacggccc gaccgagaat    5580
ggagtcatga gtactctgta caaaattgat acaagtgact ccttcatcaa cggcgtccct    5640
ctaggtcgcg ctatagacaa ctctggagcc tacattaccg acccaaatca gcagcttgtc    5700
ggccccggcg ttttgggaga gctcatcgtc accggagacg ggctcgctcg ggggtacacg    5760
gacccagcac tcgacagaga ccgattcgta caagtcgtca tcaacggcga gtctgtcaga    5820
gcatatcgga ccggagaccg catgcgctac cgcgcaggcc aagattgtct tttcgaattc    5880
tttggacgca tggactttca attcaagatt cgaagcaacc gcatcgagtc ggccgaggtg    5940
gaagctgcca ttctcagtca tcctctggtt cgcgatgcag ccattgttgt tgttggtgtc    6000
caagaggaac aagagccaga aatggttggg ttcgttgttg ctgctgacga tgccgttgag    6060
caagaggcca cagacaacca agtcgagggt tggcaagaac tgtttgagag tagcatgtac    6120
aacggcatcg atgcaataag cccgtctgct ctcggcaagg actttacagg gtggacgtcc    6180
atgtacgatg aagtgaaat cgacaagtcg gagatgcagg agtggctcga cgatacgata    6240
catactctac gcgacggtca tgtaccgggg catgtcctgg agattggaac cggtacaggt    6300
atgatcttgt ttaacctcgg ctctgttgag agctacgtag gtctggaacc caccaagtcc    6360
gcggtcgagt ttgtcaacaa ggccatcaag accctgccaa atctcgcagg aagggccgag    6420
gttcacactg gcaccgccac agatatcgac cagctgagcg gactgcggcc agaccttgtt    6480
atactaaact ctgtggttca gtactttccc acagtagaat atctgacacg ggttgtggac    6540
gctctggtcc ggatacgcgg cgtcaaacgt ctcttctttg gtgatgtgcg atcacaggcg    6600
ctacacagac agtttcttgc tgcctgtgcg atgcacgcac taggcaagac ggcgaccagg    6660
gacgacgtgc ggagatacat ggcagagcgg gaggagcggg aggaggagct gctcgtcgag    6720
ccagcctttt tcacagcact catgaaccgg catcccaatc tgatccagca cgtcgagatt    6780
ctgcccaaga atataagggc cacaaatgag ctgagcgcat accgttatgc agccgtcgtc    6840
catctacgtg atccggagtc tgcggcgcgg ccggtgtatc cgattgcggc agacgactgg    6900
gtcgactttc aggcctccca gatgcgcagc gacgtccttc gagaatacct gcgtctctcg    6960
gccggtgccg ataccgtggc tgtctgcaat attccgtacg aaaagaccat ctttgagaga    7020
ctgattgtcg agtcacttga tgacaacacc ggcagtgacg cgccacagag taggctgcat    7080
ggcaggtcac tagatggcgc gccctggata tccgccgtcc gctccgacgc cgagagccgg    7140
gcatccctct ccgtgccgga ccttgtgcag ctagccgccg agtctggctt ccaggtacag    7200
gtgagtgccg cacgacagtg gtcgcagagc ggcgcgctgg acgccgtctt ccaccgccgc    7260
cacgcgtcgt cctctcagcc gactatgcgc acactcttcc aattcccga cgacaatgca    7320
ctgcgagctt cggctaccct gacgaaccgg ccgctgcagc ggctgcagag acgtcgcgtc    7380
gcggcgcaga ttcgcgaacg gctgcagacg ctggtgccgt cgtacatgat tcctgccaag    7440
attgtggtgc tggaccagat gcctctcaac gccaatggca aggtcgaccg gaaggagctg    7500
gctcgtagag cccggacgac gacgatgacg aagaaaaaga agccgcagcg attggcgtcg    7560
gagccagctt gtccaatcag cgacattgag gttgcactgt gcgaggaggc cacggcaacg    7620
tttggaatgc aagtcggcat cagcgatcac ttttcaaac tcggcggtca ttctctgctt    7680
```

```
gctacaaaac tcatatcccg cgtcggcgac agactgaaag cgcgcctgac ggtcaaggat    7740
gtctttgatc acccaatctt ttccgagctt gcgattgtca tacgcgaggg gctgcaaaac    7800
gtcgtgcccg tggctttgaa tggtggtgga caagcgaagc aagggtcggc gggagtagta    7860
gcgccgcgca atgaaatgga aacgatgctg tgtgaggagt ttgccaatgt ccttggcatg    7920
gatgtcggag tcacggacaa cttttttgac ctcggtgggc attcgctcat ggcgacaaag    7980
ctggcagcgc ggattgggcg tcgattgaat actacgatat cagtgaagga ggtctttgaa    8040
cacccgattg tgtttcagct cgccaattcc ctagagctgg gtcagttgga gagcgacaga    8100
gtaaagcaca caatgttggc cgattacact gcgtttcaac tcttgtctgt tgaagatttg    8160
caaggctttc ttcaaaacga gataagccct caacttgaat gtgcacatgg cggtattcaa    8220
gatgtatatc cagccacgca tatgcaaaag gcgttttat gcgacgcgtc aaccggacat     8280
cccaagcctc ttgtgccgtt ctacattgac tttcccccg actcagactg ttctactctg     8340
gtcgaggcgt gctcatctct ggtgaagcgt ttcgacatgt tcaggacagt ggtcgtggaa    8400
gctgcaggcg aactgtatca agtcgtttta gagcactttg atctacagat tgatgtcgtc    8460
gagacggagg aaaacgtcca cgcggcgacg aacgatttcg tggacagaat cttggaggtg    8520
cccgtccatc tcgggcaacc actgatacaa ttcaccattc tcaagcaggc gtcttcagta    8580
cgagtcttgc tttgtctttc tcacgccctc tatgatggct tgagtttgga gcacgtcgtg    8640
cgcgatctgc acatgcttta caaaggccgg tccctgctgc agcgaatca gttctcacgg     8700
tacatgcaat acatggacca cacgcgcaaa gccggctgtg acttttggcg cgatgtcata    8760
caagatacgc caatcactgt cctcggccat gtcgatgctg gtggccgtga gctagaagtg    8820
gaagcagcgc ggacattgca cgcgacaaag attattagca ttcctctgca ggctgtccgc    8880
agcagcatca ttacgcaggc gacagtcttc aacgctgcct gtgctctcgt gctgtctcga    8940
gaaaccggcg ccaaggacgt cgtgtttggc cggatcgtgt cggggcggca aggcctgccg    9000
gtgagctggc aaaacattgt cgggccgtgc accaatgccg taccggtgcg cgcccggatc    9060
atcgacgacg acgacgacaa ccaccggcag atgctccgcg acatgcaaga ccagtacctc    9120
ctgagcctgc cgtttgagac gctcgatttt gacgaggtcc gacgcagctg cacaaactgg    9180
ccggcgacgg ccaacaacta cgcgtgctgc gtgacgtacc acgactttc ataccaccca     9240
gagagcgaga tggagcagca gcgggtcgag atgggcgtgc tggccagaaa ggatgcgctg    9300
ctcaaggagg agcccgtgta cgacctgggc atcgcaggag aggttgagcc ggatggcgtg    9360
cacttgcaag ttaccgtggt cgcaaagacg aggctgttta gtgaagagag ggccgcatac    9420
ctgatggaag aggtgtgtag actgtttgag agtctaaact cggctttgtg a             9471
```

<210> SEQ ID NO 3
<211> LENGTH: 130
<212> TYPE: PRT
<213> ORGANISM: Mycelia sterilia

<400> SEQUENCE: 3

Met Ser Asn Met Ala Pro Leu Pro Thr Met Gly Val Glu Gln Gln Ala
1               5                   10                  15

Leu Ser Leu Ser Cys Pro Leu Leu Pro His Asp Asp Glu Lys His Ser
            20                  25                  30

Asp Asn Leu Tyr Tyr Glu Gln Ala Thr Arg His Phe Gly Leu Ser Arg
        35                  40                  45

Asp Lys Ile Glu Asn Val Leu Pro Cys Thr Ser Phe Gln Cys Asp Val
    50                  55                  60

```
Ile Asp Cys Ala Val Asp Arg Arg His Ala Ile Gly His Val Val
 65                  70                  75                  80

Tyr Asp Ile Pro Asn Thr Val Asp Ile Gln Arg Leu Ala Ala Ala Trp
                 85                  90                  95

Lys Glu Val Val Arg Gln Thr Pro Ile Leu Arg Thr Gly Ile Phe Thr
                100                 105                 110

Ser Glu Thr Gly Asp Ser Phe Gln Ile Val Leu Lys Glu Gly Cys Leu
        115                 120                 125

Pro Trp
    130

<210> SEQ ID NO 4
<211> LENGTH: 115
<212> TYPE: PRT
<213> ORGANISM: Beauveria bassiana

<400> SEQUENCE: 4

Met Ser Leu His Thr Pro Ser Asp Gly Gln Gln Asp Pro Ala Leu Ala
  1               5                  10                  15

Ser Lys Thr Leu Cys Glu Gln Ile Ser Arg Ala Leu Gly Leu Gly Gln
                 20                  25                  30

Asp Lys Ile Glu Asn Ile Phe Pro Gly Pro Phe Gln Arg Asp Val Ile
            35                  40                  45

Asp Cys Ala Ala Asp Lys Gln Arg Ala Val Gly His Ala Val Phe
 50                  55                  60

Glu Ile Pro Lys Asp Ile Asp Ala Ala Arg Leu Ala Ala Ala Trp Lys
 65                  70                  75                  80

Glu Thr Val Leu His Thr Pro Ala Leu Arg Thr Cys Thr Phe Thr Ser
                 85                  90                  95

Lys Ser Gly Asp Val Leu Gln Val Phe Val Leu Arg Asp Ser Phe Val
                100                 105                 110

Phe Ser Trp
    115

<210> SEQ ID NO 5
<211> LENGTH: 102
<212> TYPE: PRT
<213> ORGANISM: Mycelia sterilia

<400> SEQUENCE: 5

Met Tyr Ala Thr Cys Leu Gly Met Lys Gly Ala Val Ile Gln Asp Glu
  1               5                  10                  15

Ala Val Ala Ala Met Thr Gly Pro Arg Cys Asn Arg Tyr Val Val Leu
                 20                  25                  30

Glu Asp Pro Ser Thr Lys Gln Arg Leu Leu Ile Trp Thr Phe Ser His
            35                  40                  45

Ala Leu Val Asp Tyr Thr Val Gln Glu Arg Ile Leu Gln Arg Val Leu
 50                  55                  60

Thr Val Tyr Asp Gly Arg Asp Val Glu Cys Pro Arg Ile Lys Asp Thr
 65                  70                  75                  80

Glu His Val Ser Arg Phe Trp Gln Gln His Phe Glu Gly Leu Asp Ala
                 85                  90                  95

Ser Val Phe Pro Leu Leu
                100

<210> SEQ ID NO 6
```

```
<211> LENGTH: 129
<212> TYPE: PRT
<213> ORGANISM: Beauveria bassiana

<400> SEQUENCE: 6

Met Ser Gly Pro Ser Val Asp Leu Lys Glu Ala Val Val Gln Asp Glu
1               5                   10                  15

Ala Ala Ala Ala Leu Ala Gly Pro Arg Cys Asn Arg Phe Val Leu Leu
            20                  25                  30

Glu Asp Pro Asp Thr Lys Glu Arg Gln Leu Ile Trp Thr Phe Ser His
        35                  40                  45

Ala Leu Val Asp Ser Thr Phe Gln Glu Arg Ile Leu Arg Arg Val Leu
    50                  55                  60

Lys Ala Tyr Lys Asp Ala Asn Asp Glu His Pro Arg Gln Phe Glu Pro
65                  70                  75                  80

Asp Ser Ser Gln Ala Thr Pro Glu Glu Asp Leu Gln Pro Asn Pro Ser
                85                  90                  95

Lys Met Leu Lys Ile Pro Gln Ala Ala Asp Met Asp Arg Ala Val Glu
            100                 105                 110

Phe Trp Lys Asp His Leu Ser Gly Leu Asn Ala Ser Ala Phe Pro His
        115                 120                 125

Leu

<210> SEQ ID NO 7
<211> LENGTH: 130
<212> TYPE: PRT
<213> ORGANISM: Mycelia sterilia

<400> SEQUENCE: 7

Pro Ser His Leu Thr Val Cys Asn Pro Asn Ala Arg Ala Glu His His
1               5                   10                  15

Ile Ser Tyr Thr Gly Pro Val Gln Arg Lys Trp Ser His Thr Ser Ile
            20                  25                  30

Cys Arg Ala Ala Leu Ala Val Leu Leu Ser Arg Phe Thr His Ser Ser
        35                  40                  45

Glu Ala Leu Phe Gly Val Val Thr Glu Gln Ser His Asn Ser Glu Asp
    50                  55                  60

Gln Arg Arg Ser Ile Asp Gly Pro Ala Arg Thr Val Val Pro Ile Arg
65                  70                  75                  80

Val Leu Cys Ala Pro Asp Gln Tyr Val Ser Asp Val Ile Gly Ala Ile
                85                  90                  95

Thr Ala His Glu His Ala Met Arg Gly Phe Glu His Ala Gly Leu Arg
            100                 105                 110

Asn Ile Arg Arg Thr Gly Asp Asp Gly Ser Ala Ala Cys Gly Phe Gln
        115                 120                 125

Thr Val
    130

<210> SEQ ID NO 8
<211> LENGTH: 129
<212> TYPE: PRT
<213> ORGANISM: Beauveria bassiana

<400> SEQUENCE: 8

Ser Ser His Leu Ser Met Pro His Pro Asp Ala Lys Ala Glu His Arg
1               5                   10                  15

Ile Ser Tyr Ser Ser Ser Ala Gln Gln Lys Met Ser Ser Ala Thr Ile
```

```
            20                  25                  30
Cys Arg Thr Ala Leu Ala Ile Leu Leu Ser Arg Tyr Thr His Ser Pro
            35                  40                  45

Glu Ala Leu Phe Gly Ile Val Thr Glu Gln Thr Pro Leu Leu Glu Glu
        50                  55                  60

Gln Leu Met Leu Asp Gly Pro Thr Arg Thr Val Pro Ile Arg Val
65                  70                  75                  80

Ser Cys Ala Ser Glu Gln Ser Val Ser Asp Ile Met Ser Thr Ile Asp
                85                  90                  95

Ser Tyr Asp Gln Thr Met Arg Gln Phe Ala His Ala Gly Leu Arg Asn
            100                 105                 110

Ile Ala Ser Ala Gly Asp Asp Glu Ser Ala Ala Cys Gly Phe Gln Thr
            115                 120                 125

Val

<210> SEQ ID NO 9
<211> LENGTH: 130
<212> TYPE: PRT
<213> ORGANISM: Mycelia sterilia

<400> SEQUENCE: 9

Leu Leu Val Thr Asp Gly Asp Ala Pro Lys Thr Pro Gly Ser Val Leu
1               5                   10                  15

His Arg Ser Val Glu Glu Ser Asp Arg Phe Met Pro Cys Ala Asn Arg
            20                  25                  30

Ala Leu Leu Leu Asp Cys Gln Met Ala Gly Asn Ser Ala Ser Leu Val
        35                  40                  45

Ala Arg Tyr Asp His Asn Val Ile Asp Pro Arg Gln Met Ser Arg Phe
    50                  55                  60

Leu Arg Gln Leu Gly Tyr Leu Ile Gln Gln Phe His His Val Asp
65                  70                  75                  80

Leu Pro Leu Val Lys Glu Leu Asp Val Val Thr Ala Glu Asp Cys Ala
                85                  90                  95

Glu Ile Glu Lys Trp Asn Ser Glu Arg Leu Thr Met Gln Asp Ala Leu
            100                 105                 110

Ile His Asp Thr Ile Ser Lys Trp Ala Ala Gly Asp Pro Asn Lys Ala
        115                 120                 125

Ala Val
    130

<210> SEQ ID NO 10
<211> LENGTH: 129
<212> TYPE: PRT
<213> ORGANISM: Beauveria bassiana

<400> SEQUENCE: 10

Leu Leu Val Ser Asp Gly Asp Ala Gln Pro Ala Ser Thr Trp Glu Ile
1               5                   10                  15

Leu Lys Lys Thr Glu Glu Pro Glu Gly Phe Ile Pro Cys Thr Asn Arg
            20                  25                  30

Ala Leu Leu Leu Ser Cys Gln Met Thr Ser Ser Gly Ala His Leu Thr
        35                  40                  45

Ala Arg Tyr Asp Gln Ser Ile Ile Asp Ala Glu Gln Met Ala Arg Leu
    50                  55                  60

Leu Arg Gln Leu Gly His Leu Ile Gln Asn Leu Gln Thr Ser Thr Asp
65                  70                  75                  80
```

```
Leu Pro Val Glu Lys Val Asp Met Met Thr Gln Glu Asp Trp Leu Glu
                85                  90                  95

Ile Glu Arg Trp Asn Ser Asp Ser Ile Asp Ala Gln Asp Thr Leu Ile
            100                 105                 110

His Ser Glu Met Leu Lys Trp Thr Ser Gln Ser Pro Asn Lys Ala Ala
        115                 120                 125

Val
```

<210> SEQ ID NO 11
<211> LENGTH: 128
<212> TYPE: PRT
<213> ORGANISM: Mycelia sterilia

<400> SEQUENCE: 11

```
Phe Ala Trp Asp Gly Trp Thr Tyr Ala Glu Leu Asp Asn Ile Ser Ser
1               5                   10                  15

Arg Leu Ala Val Tyr Ile Gln Ser Leu Asp Leu Arg Pro Gly Gln Ala
            20                  25                  30

Ile Leu Pro Leu Cys Phe Glu Lys Ser Trp Val Val Ala Thr Ile Leu
        35                  40                  45

Ala Val Leu Lys Ala Gly Arg Ala Phe Thr Leu Ile Asp Pro Cys Asp
50                  55                  60

Pro Ser Ala Arg Met Ala Gln Val Cys Gln Gln Thr Ser Ala Thr Val
65                  70                  75                  80

Ala Leu Thr Ser Lys Leu His Asn Thr Thr Leu Arg Ser Val Val Ser
                85                  90                  95

Arg Cys Ile Val Val Asp Asp Leu Leu Arg Ser Leu Pro Arg Ala
            100                 105                 110

Asp Gly Arg Leu Lys Ala Thr Val Lys Pro Gln Asp Leu Ala Tyr Val
        115                 120                 125
```

<210> SEQ ID NO 12
<211> LENGTH: 130
<212> TYPE: PRT
<213> ORGANISM: Beauveria bassiana

<400> SEQUENCE: 12

```
Ala Ala Trp Asp Gly Glu Trp Thr Tyr Ala Glu Leu Asp Asn Val Ser
1               5                   10                  15

Ser Arg Leu Ala Gln His Ile Asn Ser Ile Asp Leu Gly Lys Glu His
            20                  25                  30

Ala Ile Val Pro Ile Tyr Phe Glu Lys Ser Lys Trp Val Val Ala Ser
        35                  40                  45

Met Leu Ala Val Leu Lys Ala Gly His Ala Phe Thr Leu Ile Asp Pro
50                  55                  60

Ser Asp Pro Pro Ala Arg Thr Ala Gln Val Val Gln Gln Thr Ser Ala
65                  70                  75                  80

Thr Val Ala Leu Thr Ser Lys Leu His Arg Glu Thr Val Gln Ser Thr
                85                  90                  95

Val Gly Arg Cys Ile Val Val Asp Glu Glu Phe Val Lys Ser Leu Pro
            100                 105                 110

Gln Ser Ser Glu Leu Ser Ala Ser Val Lys Ala His Leu Asp Leu Ala
        115                 120                 125

Tyr Val
    130
```

<210> SEQ ID NO 13
<211> LENGTH: 130
<212> TYPE: PRT
<213> ORGANISM: Mycelia sterilia

<400> SEQUENCE: 13

Ile Phe Thr Ser Gly Ser Thr Gly Glu Pro Lys Gly Ile Met Ile Glu
1               5                   10                  15

His Arg Gly Phe Val Ser Cys Ala Met Lys Phe Gly Pro Ala Leu Gly
            20                  25                  30

Met Asp Glu His Thr Arg Ala Leu Gln Phe Ala Ser Tyr Ala Phe Gly
        35                  40                  45

Ala Cys Leu Val Glu Val Val Thr Ala Leu Met His Gly Gly Cys Val
    50                  55                  60

Cys Ile Pro Ser Asp Asp Arg Leu Asn Asn Val Pro Glu Phe Ile
65                  70                  75                  80

Lys Arg Ala Gln Val Asn Trp Val Ile Leu Thr Pro Ser Tyr Ile Gly
                85                  90                  95

Thr Phe Gln Pro Glu Asp Val Pro Gly Leu Gln Thr Leu Val Leu Val
            100                 105                 110

Gly Glu Pro Ile Ser Ala Ser Ile Arg Asp Thr Trp Ala Ser Gln Val
        115                 120                 125

Arg Leu
    130

<210> SEQ ID NO 14
<211> LENGTH: 128
<212> TYPE: PRT
<213> ORGANISM: Beauveria bassiana

<400> SEQUENCE: 14

Ile Phe Thr Ser Gly Ser Thr Ile Pro Lys Gly Ile Met Ile Glu His
1               5                   10                  15

Arg Ser Phe Ser Ser Cys Ala Ile Lys Gly Pro Ala Leu Gly Ile Thr
            20                  25                  30

Ser Asp Thr Arg Ala Leu Gln Phe Gly Ser His Ala Phe Gly Ala Cys
        35                  40                  45

Ile Leu Glu Ile Met Thr Thr Leu Ile His Gly Gly Cys Val Cys Ile
    50                  55                  60

Pro Ser Asp Asp Asp Arg Met Asn Asn Val Leu Glu Phe Ile Asn Arg
65                  70                  75                  80

Thr Asn Val Asn Trp Val Met Ala Thr Pro Ser Tyr Met Gly Thr Phe
                85                  90                  95

Gln Pro Glu Val Val Pro Gly Leu Lys Thr Leu Val Leu Val Gly Glu
            100                 105                 110

Gln Met Ser Ala Ser Val Asn Glu Val Trp Ala Pro Arg Val Gln Leu
        115                 120                 125

<210> SEQ ID NO 15
<211> LENGTH: 130
<212> TYPE: PRT
<213> ORGANISM: Mycelia sterilia
<220> FEATURE:
<221> NAME/KEY: misc_feature
<222> LOCATION: (115)..(115)
<223> OTHER INFORMATION: Xaa can be any naturally occurring amino acid

<400> SEQUENCE: 15

Leu Asn Ala Tyr Gly Gln Ser Glu Ser Ser Thr Met Cys Ser Val Thr
1               5                   10                  15

Glu Val Ser Pro Leu Ser Leu Glu Pro Asn Asn Ile Gly Arg Ala Val
            20                  25                  30

Gly Ala Arg Ser Trp Ile Ile Asp Pro Asp Glu Pro Asp Arg Leu Ala
        35                  40                  45

Pro Ile Gly Cys Ile Gly Glu Leu Val Ile Glu Ser Pro Gly Ile Ala
    50                  55                  60

Arg Asp Tyr Ile Ile Ala Pro Pro Asp Lys Ser Pro Phe Leu Leu
65                  70                  75                  80

Ala Pro Pro Ala Trp Tyr Pro Ala Gly Lys Leu Ser Asn Ala Phe Lys
                85                  90                  95

Pro Tyr Lys Thr Gly Asp Leu Val Arg Tyr Gly Pro Asp Gly Thr Ile
            100                 105                 110

Val Cys Xaa Gly Arg Lys Asp Ser Gln Val Lys Ile Arg Gly Gln Arg
        115                 120                 125

Val Glu
    130

<210> SEQ ID NO 16
<211> LENGTH: 130
<212> TYPE: PRT
<213> ORGANISM: Beauveria bassiana
<220> FEATURE:
<221> NAME/KEY: misc_feature
<222> LOCATION: (97)..(97)
<223> OTHER INFORMATION: Xaa can be any naturally occurring amino acid

<400> SEQUENCE: 16

Leu Asn Gly Tyr Gly Gln Ser Glu Ser Ser Ser Ile Cys Cys Val Ala
1               5                   10                  15

Lys Ile Ser Pro Gly Ser Ser Glu Pro Asn Asn Ile Gly His Ala Val
            20                  25                  30

Gly Ala His Ser Trp Ile Val Asp Pro Glu Asp Pro Asn Arg Leu Ala
        35                  40                  45

Pro Ile Gly Ala Val Gly Glu Leu Val Ile Glu Ser Ala Gly Ile Ala
    50                  55                  60

Arg Asp Tyr Ile Val Ala Pro Thr Gln Asp Lys Ser Pro Phe Ile Lys
65                  70                  75                  80

Thr Ala Pro Thr Trp Tyr Pro Ala Lys Gln Leu Pro Asp Gly Phe Lys
                85                  90                  95

Xaa Tyr Arg Thr Gly Asp Leu Ala Cys Tyr Ala Ser Asp Gly Ser Ile
            100                 105                 110

Val Cys Leu Gly Arg Met Asp Ser Gln Val Lys Ile Arg Gly Gln Arg
        115                 120                 125

Val Glu
    130

<210> SEQ ID NO 17
<211> LENGTH: 131
<212> TYPE: PRT
<213> ORGANISM: Mycelia sterilia
<220> FEATURE:
<221> NAME/KEY: misc_feature
<222> LOCATION: (101)..(101)
<223> OTHER INFORMATION: Xaa can be any naturally occurring amino acid

<400> SEQUENCE: 17

Ile Ser Ala Val Glu Ala Ser Leu Arg Arg Gln Leu Pro Asp Ser Asp

```
                1               5                   10                  15
        Ile Met Pro Val Ala Glu Ala Ile Lys Arg Ser Asp Ser Ser Gly Ser
                        20                  25                  30

Thr Val Leu Thr Ala Phe Leu Ile Gly Ser Ser Lys Ser Leu Ser Ala
                        35                  40                  45

Ala Asp Ala Val Ile Leu Asp His Gly Ala Thr Asn Glu Ile Asn Ala
                50                  55                  60

Lys Leu Gln Gln Ile Leu Pro Gln His Ser Val Pro Ser Tyr Tyr Ile
        65                  70                  75                  80

His Met Glu Asn Leu Pro Arg Thr Ala Thr Gly Ala Asp Arg Lys Met
                        85                  90                  95

Leu Arg Ser Ile Xaa Ser Lys Leu Leu Gly Glu Leu Ser Gln Gln Asn
                        100                 105                 110

Val Thr Ser Gln Pro Ile Glu Lys His Asp Leu Pro Ala Thr Gly Ile
                        115                 120                 125

Glu Val Lys
                130

<210> SEQ ID NO 18
<211> LENGTH: 126
<212> TYPE: PRT
<213> ORGANISM: Beauveria bassiana
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid

<400> SEQUENCE: 18

Leu Gly Ala Val Glu Thr His Leu Arg Gln Gln Met Pro Asp Asp Met
1               5                   10                  15

Thr Ile Val Val Glu Ala Val Lys Phe Ser Asp Ser Ser Ser Thr Thr
                20                  25                  30

Val Leu Thr Ala Phe Leu Ile Gly Ala Gly Glu Lys Asn Ser His Ile
                35                  40                  45

Leu Asp Gln Arg Ala Thr Arg Glu Ile Asn Ala Lys Met Glu Gln Val
        50                  55                  60

Leu Pro Arg His Ser Ile Pro Ala Phe Tyr Ile Ser Met Asn Asn Leu
65              70                  75                  80

Pro Gln Thr Ala Thr Gly Lys Val Asp Arg Arg Lys Leu Arg Ile Met
                85                  90                  95

Xaa Ser Lys Ile Leu Ser Gln Lys Thr His Ser Thr Pro Ser Gln Gln
                100                 105                 110

Ser Gln Ala Ala Ile Xaa Ser Gly Thr Asp Thr Glu Thr Lys
        115                 120                 125

<210> SEQ ID NO 19
<211> LENGTH: 129
<212> TYPE: PRT
<213> ORGANISM: Mycelia sterilia
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
```

<400> SEQUENCE: 19

```
Leu Lys Glu Leu Trp Phe Leu Ser Leu Asn Leu Asn Pro Asn Ser Gln
1               5                   10                  15

Asp Val Gly Ala Ser Phe Phe Xaa Leu Gly Gly Asn Ser Ile Ile Ala
            20                  25                  30

Ile Lys Met Val Asn Met Ala Arg Ser Asn Gly Ile Glu Leu Lys Val
        35                  40                  45

Ser Asp Ile Xaa Gln Asn Pro Thr Leu Ala Gly Leu Val Asp Val Ile
    50                  55                  60

Gly Arg Asp Pro Ala Pro Tyr Asn Leu Ile Pro Thr Thr Ala Tyr Ser
65                  70                  75                  80

Gly Pro Val Glu Gln Ser Phe Ala Gln Gly Arg Leu Trp Phe Leu Asp
                85                  90                  95

Gln Ile Glu Leu Asp Ala Leu Trp Tyr Leu Leu Pro Tyr Ala Val Arg
            100                 105                 110

Met Arg Gly Pro Leu His Ile Asp Ala Leu Thr Ile Ala Leu Leu Ala
        115                 120                 125

Ile
```

<210> SEQ ID NO 20
<211> LENGTH: 129
<212> TYPE: PRT
<213> ORGANISM: Beauveria bassiana
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid

<400> SEQUENCE: 20

```
Leu Glu Ser Ile Trp Ile Thr Ser Leu Asp Leu Glu Pro Gly Ser Ala
1               5                   10                  15

Asn Met Ser Ala Thr Phe Phe Xaa Met Gly Gly Asn Ile Ile Ala Ile
            20                  25                  30

Lys Met Val Asn Met Ala Arg Ser Asn Gly Ile Glu Leu Lys Val Ser
        35                  40                  45

Asp Ile Xaa Gln Asn Pro Thr Leu Ala Gly Leu Xaa Ala Ile Val Ile
    50                  55                  60

Gly Thr Ser Leu Pro Tyr Ser Leu Ile Pro Lys Val Thr Arg Gln Gly
65                  70                  75                  80

Pro Val Ser Glu Gln Ser Tyr Ala Gln Asn Arg Met Trp Phe Leu Asp
                85                  90                  95

Gln Leu Ser Glu Gly Ala Ser Trp Tyr Leu Ile Pro Phe Ala Val Arg
            100                 105                 110

Met Arg Gly Pro Val Asp Val Asp Ala Leu Thr Arg Ala Leu Leu Ala
        115                 120                 125

Leu
```

<210> SEQ ID NO 21
<211> LENGTH: 125
<212> TYPE: PRT

```
<213> ORGANISM: Mycelia sterilia
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid

<400> SEQUENCE: 21

Gln Gln Arg His Glu Thr Leu Arg Thr Thr Phe Glu Glu Gln Asp Gly
1               5                   10                  15

Val Gly Val Gln Val Val His Ala Ser Pro Ile Ser Asp Leu Arg Ile
            20                  25                  30

Ile Asp Val Ser Gly Asp Arg Asn Ser Asp Tyr Leu Gln Leu Leu His
        35                  40                  45

Gln Glu Gln Thr Thr Pro Phe Ile Leu Ala Cys Gln Ala Gly Trp Arg
    50                  55                  60

Val Ser Leu Ile Arg Leu Gly Glu Asp Xaa Ile Val Xaa His His Ile
65                  70                  75                  80

Ile Ser Asp Gly Trp Ser Ile Asp Ile Leu Arg Arg Glu Leu Ser Asn
                85                  90                  95

Phe Tyr Ser Ala Ala Leu Arg Gly Ser Asp Pro Leu Ser Val Val Ser
            100                 105                 110

Pro Leu Pro Leu His Tyr Arg Asp Phe Ser Val Trp Gln
        115                 120                 125

<210> SEQ ID NO 22
<211> LENGTH: 127
<212> TYPE: PRT
<213> ORGANISM: Beauveria bassiana
<220> FEATURE:
<221> NAME/KEY: misc_feature
<222> LOCATION: (96)..(96)
<223> OTHER INFORMATION: Xaa can be any naturally occurring amino acid

<400> SEQUENCE: 22

Glu Gln Arg His Glu Thr Leu Arg Thr Thr Phe Glu Asn Gln Asp Gly
1               5                   10                  15

Val Gly Val Gln Ile Ile His Asp Arg Leu Ser Lys Glu Leu Gln Val
            20                  25                  30

Ile Asp Ala Leu Asp Gly Asp Glu Gly Leu Lys Thr Leu Tyr Lys
        35                  40                  45

Val Glu Thr Thr Thr Phe Asp Ile Thr Ser Glu Ala Gly Trp Ser Ser
    50                  55                  60

Thr Leu Ile Arg Leu Gly Lys Asp Asp His Ile Leu Ser Ile Val Met
65                  70                  75                  80

His His Ile Ile Ser Asp Gly Trp Ser Ile Asp Val Leu Arg Arg Xaa
                85                  90                  95

Leu Ile Gln Tyr Ala Ala Ala Leu Gln Gly Lys Asp Pro Ser Ser Ala
            100                 105                 110

Leu Thr Pro Leu Pro Ile Gln Tyr Ser Asp Phe Ala Val Trp Gln
        115                 120                 125

<210> SEQ ID NO 23
<211> LENGTH: 130
<212> TYPE: PRT
<213> ORGANISM: Mycelia sterilia

<400> SEQUENCE: 23
```

```
Lys Gln Val Glu Gln Glu Thr Glu His Glu Arg Gln Leu Gly Tyr Trp
1               5                  10                 15

Val Lys Gln Leu Ala Asp Ser Ser Ala Ala Glu Phe Leu Thr Asp Phe
                20                 25                  30

Pro Arg Pro Asn Ile Leu Ser Gly Glu Ala Gly Ser Val Pro Val Thr
                35                 40                  45

Ile Glu Gly Glu Leu Tyr Glu Arg Leu Gln Glu Phe Cys Lys Val Glu
            50                 55                  60

Gln Met Thr Pro Phe Ala Val Leu Leu Gly Ala Phe Arg Ala Thr His
65                  70                 75                  80

Tyr Arg Leu Thr Gly Ala Glu Asp Ser Ile Ile Gly Thr Pro Ile Ala
                85                 90                  95

Asn Arg Asn Arg Gln Glu Leu Glu Asn Met Ile Gly Phe Phe Val Asn
                100                105                 110

Thr Gln Cys Met Arg Ile Thr Val Asp Gly Asp Asp Thr Phe Glu Ser
            115                120                 125

Leu Val
    130

<210> SEQ ID NO 24
<211> LENGTH: 47
<212> TYPE: PRT
<213> ORGANISM: Beauveria bassiana

<400> SEQUENCE: 24

Lys Gln Glu Ala Gln Ala Ala Glu His Glu Arg Gln Leu Gln Tyr Trp
1               5                  10                 15

Lys Lys Gln Leu Ala Asp Ser Ser Pro Ala Lys Ile Pro Thr Lys Phe
                20                 25                  30

Pro Arg Pro Asp Leu Leu Ser Gly Asp Ala Gly Val Val Pro Val
                35                 40                  45

<210> SEQ ID NO 25
<211> LENGTH: 47
<212> TYPE: PRT
<213> ORGANISM: Mycelia sterilia

<400> SEQUENCE: 25

Arg Gln Val Arg Thr Thr Ala Thr Ala Ala Phe Glu His Gln Asp Val
1               5                  10                 15

Pro Phe Glu Arg Val Val Thr Ala Leu Leu Pro Arg Ser Arg Asp Leu
                20                 25                  30

Ser Arg Asn Pro Leu Ala Gln Leu Thr Phe Ala Leu His Ser Gln
                35                 40                  45

<210> SEQ ID NO 26
<211> LENGTH: 46
<212> TYPE: PRT
<213> ORGANISM: Beauveria bassiana

<400> SEQUENCE: 26

Arg Gln Val Arg Ser Thr Thr Thr Ala Ala Phe Ala His Glu Asp Val
1               5                  10                 15

Pro Phe Glu Arg Val Val Ser Ala Leu Gln Pro Gly His Arg Asp Leu
                20                 25                  30

Ser Arg Thr Pro Leu Ala Gln Ile Met Ala Val His Ser Gln
                35                 40                  45
```

<210> SEQ ID NO 27
<211> LENGTH: 47
<212> TYPE: PRT
<213> ORGANISM: Mycelia sterilia

<400> SEQUENCE: 27

Leu Ala Asp Leu Arg Ala Met Gly Leu Leu Glu Ile Glu Lys Ala Glu
1               5                   10                  15

Tyr Pro Arg Glu Ser Ser Val Val Asp Val Phe Arg Lys Gln Val Ala
            20                  25                  30

Ala His Pro His Ala Phe Ala Val Val Asp Ser Ala Ser Arg Leu
        35                  40                  45

<210> SEQ ID NO 28
<211> LENGTH: 47
<212> TYPE: PRT
<213> ORGANISM: Beauveria bassiana

<400> SEQUENCE: 28

Val Glu Glu Leu Arg Arg Leu Asp Leu Leu Glu Ile Lys Arg Thr Asn
1               5                   10                  15

Tyr Pro Arg Asp Ser Ser Val Val Asp Val Phe Arg Glu Gln Ala Ala
            20                  25                  30

Ala Asn Pro Glu Val Ile Ala Val Thr Asp Ser Ser Ser Arg Leu
        35                  40                  45

<210> SEQ ID NO 29
<211> LENGTH: 47
<212> TYPE: PRT
<213> ORGANISM: Mycelia sterilia

<400> SEQUENCE: 29

Thr Pro Asp Val Gln Ile Pro Asp Val Glu Leu Val Arg Ile Ser Asp
1               5                   10                  15

Ile Leu Asp Arg Pro Ile Asn Gly Gln Ala Lys Leu Asn Gly His Thr
            20                  25                  30

Lys Ser Asn Gly Tyr Ser Lys Pro Asn Gly Tyr Thr His Leu Lys
        35                  40                  45

<210> SEQ ID NO 30
<211> LENGTH: 22
<212> TYPE: PRT
<213> ORGANISM: Beauveria bassiana

<400> SEQUENCE: 30

Asp Pro Gly Phe Asp Leu Pro Gln Leu Glu Leu Val Arg Ile Thr Asp
1               5                   10                  15

Thr Phe Asp Glu Thr Ile
            20

<210> SEQ ID NO 31
<211> LENGTH: 47
<212> TYPE: PRT
<213> ORGANISM: Mycelia sterilia

<400> SEQUENCE: 31

Ile Ile Ser Arg Phe Pro Ser Val Ala Lys Val Ala His Leu Ser Asn
1               5                   10                  15

Ile Ala Phe Asp Ala Ala Thr Trp Glu Met Phe Ala Ala Leu Leu Asn
            20                  25                  30

```
Gly Gly Thr Leu Val Cys Ile Asp Tyr Met Thr Thr Leu Asp Ser
            35                  40                  45
```

<210> SEQ ID NO 32
<211> LENGTH: 46
<212> TYPE: PRT
<213> ORGANISM: Beauveria bassiana

<400> SEQUENCE: 32

```
Phe Pro Gly Phe Pro Ser Pro Ala Arg Met Ser Asn Val Phe Asn Pro
1               5                   10                  15

Ala Phe Asp Gly Ala Ile Trp Glu Ile Asn Trp Met Leu Leu Asn Gly
                20                  25                  30

Gly Thr Val Val Cys Ile Asp Tyr Leu Thr Thr Leu Asp Gly
            35                  40                  45
```

<210> SEQ ID NO 33
<211> LENGTH: 47
<212> TYPE: PRT
<213> ORGANISM: Mycelia sterilia

<400> SEQUENCE: 33

```
Asp Ser Phe Ile Asn Gly Val Pro Ile Gly Cys Ala Ile Ser Asn Ser
1               5                   10                  15

Gly Ala Tyr Ile Thr Asp Pro Asp Gln Gln Leu Val Pro Pro Gly Val
                20                  25                  30

Met Gly Glu Leu Val Val Thr Gly Asp Gly Leu Ala Arg Gly Tyr
            35                  40                  45
```

<210> SEQ ID NO 34
<211> LENGTH: 47
<212> TYPE: PRT
<213> ORGANISM: Beauveria bassiana

<400> SEQUENCE: 34

```
Glu Ala Tyr Thr Asn Gly Val Pro Ile Gly Gly Ser Ile Tyr Asn Ser
1               5                   10                  15

Gly Ala Tyr Val Met Asp Pro Asn Gln Gln Leu Val Gly Leu Gly Val
                20                  25                  30

Met Gly Glu Leu Val Val Thr Gly Asp Gly Val Gly Arg Gly Tyr
            35                  40                  45
```

<210> SEQ ID NO 35
<211> LENGTH: 50
<212> TYPE: PRT
<213> ORGANISM: Beauveria bassiana

<400> SEQUENCE: 35

```
Val Leu Thr Ala Phe Leu Ile Gly Ser Ser Lys Ser Leu Ser Ala Ala
1               5                   10                  15

Asp Ala Val Ile Leu Asp His Gly Ala Thr Asn Glu Ile Asn Ala Lys
                20                  25                  30

Leu Gln Gln Ile Leu Pro Gln His Ser Val Pro Ser Tyr Tyr Ile His
            35                  40                  45

Met Glu
    50
```

<210> SEQ ID NO 36
<211> LENGTH: 46
<212> TYPE: PRT
<213> ORGANISM: Mycelia sterilia

<400> SEQUENCE: 36

Val Leu Thr Ala Phe Leu Ile Gly Ala Gly Glu Lys Asn Ser His Ile
1               5                   10                  15

Leu Asp Gln Arg Ala Thr Arg Glu Ile Asn Ala Lys Met Glu Gln Val
            20                  25                  30

Leu Pro Arg His Ser Ile Pro Ala Phe Tyr Ile Ser Met Asn
        35                  40                  45

<210> SEQ ID NO 37
<211> LENGTH: 50
<212> TYPE: PRT
<213> ORGANISM: Beauveria bassiana

<400> SEQUENCE: 37

Ile Lys Met Val Asn Met Ala Arg Ser Ala Gly Ile Ala Leu Lys Val
1               5                   10                  15

Ser Asp Ile Pro Gln Asn Pro Thr Leu Ala Gly Leu Val Asp Val Ile
            20                  25                  30

Gly Arg Asp Pro Ala Pro Tyr Asn Leu Ile Pro Thr Thr Ala Tyr Ser
        35                  40                  45

Gly Pro
    50

<210> SEQ ID NO 38
<211> LENGTH: 50
<212> TYPE: PRT
<213> ORGANISM: Mycelia sterilia

<400> SEQUENCE: 38

Ile Lys Met Val Asn Met Ala Arg Ser Asn Gly Ile Glu Leu Lys Val
1               5                   10                  15

Ser Asp Ile Tyr Gln Asn Pro Thr Leu Ala Gly Leu Lys Ala Ile Val
            20                  25                  30

Ile Gly Thr Ser Leu Pro Tyr Ser Leu Ile Pro Lys Val Thr Arg Gln
        35                  40                  45

Gly Pro
    50

<210> SEQ ID NO 39
<211> LENGTH: 49
<212> TYPE: PRT
<213> ORGANISM: Beauveria bassiana

<400> SEQUENCE: 39

Ile Asp Val Ser Gly Asp Arg Asn Ser Asp Tyr Leu Gln Leu Leu His
1               5                   10                  15

Gln Glu Gln Thr Thr Pro Phe Ile Leu Ala Cys Gln Ala Gly Trp Arg
            20                  25                  30

Val Ser Leu Ile Arg Leu Gly Glu Asp Asp His Ile Leu Ser Ile Val
        35                  40                  45

Met

<210> SEQ ID NO 40
<211> LENGTH: 48
<212> TYPE: PRT
<213> ORGANISM: Mycelia sterilia

<400> SEQUENCE: 40

-continued

```
Ile Asp Ala Leu Asp Gly Asp Glu Gly Gly Leu Lys Thr Leu Tyr Lys
1               5               10                  15

Val Glu Thr Thr Thr Phe Asp Ile Thr Ser Glu Ala Gly Trp Ser Ser
                20              25              30

Thr Leu Ile Arg Leu Gly Lys Asp Asp His Ile Leu Ser Ile Val Met
            35              40              45
```

PROCESS FOR PRODUCING CHIMERIC CYCLOOLIGODEPSIPEPTIDES IN FILAMENTOUS FUNGI

CROSS-REFERENCE TO RELATED APPLICATION

This application is the U.S. national phase of PCT Application No. PCT/EP2015/055978 filed on Mar. 20, 2015, which claims priority to EP Patent Application No. 14160821.6 filed on Mar. 20, 2014, the disclosures of which are incorporated in their entirety by reference herein.

SEQUENCE LISTING

The text file Sequence_Listing_US of size 57 KB created Aug. 1, 2019 filed herewith, is hereby incorporated by reference.

The present invention relates to a method for obtaining microbial secondary metabolites according to claim 1, an expression cassette according to claim 16, a plasmid vector according to claim 17, cyclodepsipeptides according to claim 18, an expression host according to claim 19 and a chimeric cyclodepsipeptide synthetase according to claim 20.

DESCRIPTION

Recent genome mining efforts have uncovered that the genomes of filamentous fungi encode an unexpected rich repertoire of low molecular weight compounds with commercial relevance. These natural products known as secondary metabolites include nonribosomal peptides, polyketides and lipopeptides with pharmacological impact. However, most of the genes involved in secondary metabolism pathways are not expressed under standard laboratory or industrial conditions, what hampers application of these natural products. Different strategies based on molecular factors and cultivation methods have thus been undertaken. However, there are still major obstacles to overcome such as low production rates.

The present invention describes thus a novel approach for synthesizing microbial secondary metabolites or derivatives thereof, in particular cyclodepsipeptides.

The present method comprises the step of heterologous expression of at least one synthetase of said secondary metabolite in at least one filamentous fungus.

The filamentous fungi are preferably selected from the group of *Aspergillus* sp., *Trichoderma* sp., *Penicillium* sp., *Fusarium* sp. and *Rhizopus* spp. In particular preferred expression hosts are *Aspergillus niger*, *Aspergillus oryzae*, *Aspergillus nidulans*, *Trichoderma reesei*, *Fusarium oxysporum*, *Rhizopus oryzae*, *Penicillium chrysogenum*.

In an embodiment of the present method the synthetase is selected from the group of non-ribosomal peptide synthetase (NRPS), ribosomally synthesized and posttranslationally modified peptides (RiPPs), polyketide synthetase (PKS), terpene cyclases or hybrides thereof.

It is in particular preferred if the synthetase is a cyclodepsipeptidsynthetase, in particular a cyclodepsipeptidsynthetase of the iterative type. For example the synthetase is a cyclodepsipeptidsynthetase selected from the group containing Enniatin, PF1022, Beauvericin and Bassianolide synthetase.

It is in general also possible and conceivable to express further NRPS in one of the mentioned fungi, such as NRPS of epothilone, actinomycin, daptomycin, valinomycin, fungisporin or bleomycin.

In another variant it is desirable to express PKS systems, such as the one for erythromycin, doxycycline or geldanamycin in the fungal expression host.

The native cyclodepsipeptide synthetase typically comprises two modules: module 1 for integrating a D-hydroxycarboxylic acid, module 2 for integrating an L-amino acid and additionally a third PCP and C-domain (module 3) for determining the ring size n, typically n=6 and 8. A typical example of a cyclodepsipeptide synthetase, such as Enniatin Synthetase is shown in FIG. 1.

Enniatin is a hexacyclodepsipeptide consisting of 3 D-hydroxycarboxylic acids and 3 L-amino acids. Main products are Enniatin A, B, and C with Enniatin A comprising 3×D-Hiv, 3×L-Ile, Enniatin B comprising 3×D-Hiv, 3×L-Val and Enniatin C comprising 3×D-Hiv, 3×L-Leu. The N-atom is in any case methylated.

Enniatin is synthesized by a Enniatin Synthetase which is present in *Fusarium* sp., *Vertcillium hemipterigenum*, *Halosarpheia* sp. In case of Enniatin B module 1 is specific for D-hydroxyvalerate, module 2 is specific for L-valine and PCP/C-domain (module 3) determines the ring number n=6.

The PF1022 synthetase, which is for instant present in *Mycelia sterilia*, comprises module 1 specific for D-phenyllactate and/or D-lactate, module 2 specific for L-leucine and a PCP/C-domain (module 3) determining a ring number n=8.

The Beauvericin synthetase, for instance from *Beauveria bassiana* strain ATCC7159, comprise module 1 specific for D-hydroxyvalerate, module 2 specific for L-phenylalanine and PCP/C-domain (module 3) determining the ring number being n=6.

In another preferred embodiment a chimeric cyclodepsipeptide synthetase is used, wherein the synthetase is made of modules and/or domains of at least two different cyclodepsipeptide synthetases. It is preferred if at least one module is chosen from a first cyclodepsipeptide synthetase and and at least a second module is chosen from another cyclodepsipeptide synthetase. For example, it is possible that the synthetase comprises module 1 of one cyclodepsipeptide synthetase and modules 2 and 3 of another cyclodepsipeptide synthetase.

Preferred embodiments of such hybrid or chimeric cyclodepsipeptide synthetases can have the following arrangement:

a) module 1 from PF1022 Synthetase specific for D-Phenyllactate/D-Lactate (for example from *Mycelia sterilia*), module 2 and PCP/C-domain (module 3) from Enniatin Synthetase specific for L-Valin and n=6 (for example from *Fusarium oxysporum*; see FIG. 14, Seq ID No1), or b) module 1 from PF1022 Synthetase specific for D-Phenyllactate/D-Lactate, module 2 and PCP/C-domain (module 3) from Beauvericin Synthetase specific for L-Phenylalanine and n=6 (see FIG. 18, Seq ID No 2).

In general any other module/domain combination is possible. For example it is conceivable and possible that module 1 is chosen from an Enniatin or Beauvericin Synthetase and module 2 and PCP/C-domain (module 3) are chosen from PF1022 Synthetase.

However, a hybrid cyclodepsipeptide synthetase system comprising module 1 from beauvericin synthetase and module 2 and PCP/C-domain (module 3) from bassianolide synthetase as the synthetase system, which has been shown to be expressed in *Saccharomyces cerevisiae*, is already known and is hereby exempted (Yu et al., ChemComm., 2013, 49:6176-6178). This specific chimeric cyclodepsipeptide synthetase is however not exempted from expression in a filamentous fungus.

In a further embodiment of the present invention an inducible expression system integrated into the chromosome of the at least one filamentous fungus is used for heterologous expression of at least one synthetase. Such an inducible expression system is independent on the metabolism. Also constitutive expression is in general possible.

In a variant the expression system comprises at least one expression cassette consisting of at least three modules. The expression cassette may comprise a first module for constitutive expression of the Tetracycline dependent transactivator rtTA2, a second module (Tet-on system) harboring the rtTA2-dependent promoter for inducible expression of the at least one secondary metabolite synthetase and a third module for integrating the cassette into the fungal genome by homologous recombination.

In a most preferred embodiment the first module comprises constitutive promoter PgpdA-rtTA-terminator TcgrA, the second module comprises operator sequence tetO7- (seven copies of tetO sequence)-minimal promoter Pmin-secondary metabolite synthase (esyn1)-terminator trpC (with tetO7::Pmin as rtTA2S-M2 dependent promoter) and the third module comprises pyrG* for homologous integration of the plasmid at the pyrG locus. After transformation of the plasmid vector comprising said expression cassette into a preferable protease-negative (prtT) and uracil-auxotroph (pyrG) *A. niger* strain, uridine-prototroph transformants were selected, purified and subjected to Southern analysis. The expression cassette is exemplarily shown in FIG. 2.

Other selection systems may be based on dominant (antibiotics such as hygromycin or phleomycin), auxotrophic or nutritional selection markers established for filamentous fungi.

At least one copy of the expression cassette is integrated into the fungal genome. It is possible that multiple expression cassettes are present in the fungal genome.

In another variant of the present invention the expression cassette comprises further genes encoding for biosynthetic enzymes of metabolic precursors or metabolic intermediates, in particular dehydrogenases. For example, using dehydrogenases for transforming amino acids to hydroxycarboxylic acids, which are expressed constitutively, allows an independent synthesis of different hydroxycarboxylic acids.

Said further genes may also not be part of the expression cassette and may be expressed from a different chromosomal location by using at least one constitutive, inducible or repressible promoter.

The transformed fungal expression host is grown in a suitable culture medium. The culture media used for heterologous expression of the synthetase may comprise talcum, titanite, silica or aluminium oxide particles, wherein talcum particles are in particular preferred. These particles support formation of smaller fungal pellets.

The culture media comprises furthermore glucose, trace elements, casamino acids, $MgSO_4$, yeast extracts. In one variant of the present method the glucose concentration is 1-10%, preferably 2.5 to 7.5%, mostly preferably 5%.

It is also preferred if the culture media used for heterologous expression of the synthetase comprises 5-50 mM, preferably 10-30 mM, most preferably 20 mM of at least one hydroxycarboxylic acid or derivatives thereof (for example 20 mM D-hydroxyvalerate) and 10-30 mM, preferably 15-25 mM, most preferably 20 mM of at least one amino acid or a derivative thereof (for example L-valine).

It is in general also possible to replace the hydroxycarboxylic acid by their corresponding esters, by O-acylated hydroxycarboxylc acids and their corresponding esters. The methyl esters are thereby preferred.

The induction of the expression occurs by adding the appropriate inducer, for example 5-200 µg/ml, in particular 10-100 µg/ml, most preferably 10-50 µg/ml doxycycline or other inducers such as tetracyclin or derivatives thereof. The addition of 10 µg/ml doxycycline is in particular preferred. The induction is preferably carried out in the exponential phase, in particular in batch or fed batch culture. The inducer can be added once or repeatedly.

In a further embodiment of the present invention the culture media used for heterologous expression of the synthetase comprises at least one D- or L-hydroxycarboxylic acid (or racemic mixtures thereof) of the general formulae (I) $R^1$—CHOH—$CO_2H$, wherein $R^1$ can be selected from a group comprising substituted and non-substituted $C_1$-$C_{50}$-alkyl, substituted and non-substituted $C_2$-$C_{50}$-alkenyl, substituted and non-substituted $C_2$-$C_{50}$-alkinyl, substituted and non-substituted $C_3$-$C_{10}$-cycloalkyl, substituted and non-substituted $C_5$-$C_7$-cycloalkenyl, which in each case can be interrupted by one or more oxygen atoms, sulphur atoms, substituted or mono-substituted nitrogen atoms, double bonds and/or by one or more groups of the type —C(O)O—, —OC(O)—, —C(O)—, —NHC(O)O—, —CO(O)NH— and/or —OC(O)O—, or aryl, heteroaryl, —$CH_2$-aryl or —$CH_2$-heteroaryl, wherein aryl and heteroaryl are substituted or non-substituted.

Thus, the hydroxycarboxylic acids may be fed to the culture media during growth of the expression host. It is however also possible that at least some of the hydroxycarboxylic acids are synthesized by the expression host itself.

The moiety $R^1$ can be selected from a group comprising substituted and non-substituted $C_1$-$C_{12}$-alkyl, substituted and non-substituted $C_3$-$C_7$-cycloalkyl and substituted and non-substituted $C_2$-$C_{12}$-alkenyl and substituted and non-substituted $C_6$-$C_{12}$ Aryl, in particular —$C_6H_5$.

The term "substituted" in connection to alkyl, alkenyl, alkinyl, cycloalkenyl relates to the substitution of one or more atoms, usually H-atoms, by one or more of the following substituents: halogen, in particular F, Cl, Br, hydroxy, protected hydroxy, oxo, protected oxo, —$N_3$, $C_3$-$C_7$-cycloalkyl, phenyl, naphtyl, amino, protected amino, primary, secondary or tertiary amino, heterocyclic ring, imidazolyl, indolyl, pyrrolidinyl, $C_1$-$C_{12}$-alkoxy, $C_1$-$C_{12}$-acyl, $C_1$-$C_{12}$-acyloxy, nitro, carboxy, carbamoyl, carboxamid, N—($C_1$-$C_{12}$-alkyl)carboxamid, N,N-Di($C_1$-$C_{12}$-alkyl)carboxamid, cyano, methylsulfonylamino, thiol, $C_1$-$C_{10}$-alkylthio and $C_1$-$C_{10}$-alkylsulfonyl. The substituted groups can once or twice substituted with same or different substituents.

Examples for the above substituted alkyl groups comprise 2-oxo-prop-1-yl, 3-oxo-but-1-yl, cyanomethyl, nitromethyl, chlormethyl, hydroxymethyl, tetrahydropyranyloxymethy, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chlormethyl, brommethyl, iodmethyl, trifluormethyl, 6-hydroxyhexyl, 2,4-dichlor(n-butyl), 2-aminopropyl, 1-chlorethyl, 2-chlorethyl, 1-bromethyl, 2-bromethyl, 1-fluorethyl, 2-fluorethyl, 1-iodethyl, 2-iodethyl, 1-chlorpropyl, 2-chlorpropyl, 3-chlorpropyl, 1-brompropyl, 2-brompropyl, 3-brompropyl, 1-fluorpropyl, 2-fluorptopyl, 3-fluorpropyl, 1-iodpropyl, 2-iodpropyl, 3-iodpropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and alike.

Examples for the above substituted alkenylgroups comprise styrolyl, 3-chlor-propen-1-yl, 3-chlor-buten-1-yl, 3-methoxy-propen-2-yl, 3-phenyl-buten-2-yl, 1-cyano-buten-3-yl and alike.

The term "alkinyl" as used herein relates to a moiety of the formulae R—C≡C—, in particular to a $C_2$-$C_{50}$-Alkinyl". Examples for $C_2$-$C_{50}$-alkinyle comprise ethinyl, propinyl, 2-butinyl, 2-pentinyl, 3-pentinyl, 2-hexinyl, 3-hexinyl, 4-hexinyl, 2-heptinyl, 3-heptinyl, 4-heptinyl, 5-heptinyl, octinyl, noninyl, decinyl, undecinyl, dodecinyl, as well as di- and tri-ines of straight or branched alky chains.

The term "oxo" relates to a carbon atom, which is connected with an oxygen atom via a double bond whereby a keto or an aldehyde group is formed. The term "protected oxo" relates to a carbon atom, which is substituted by two alkoxy groups or is connected twice with a substituted diol forming a non-cyclic or cyclic ketal group.

The term "alkoxy" relates to moieties like methoxy, ethoxy, n-propoxy, isopropoxy, n-butoxy, t-butoxy and alike. A preferred alkoxy group is methoxy.

The term "$C_3$-$C_7$-cycloalkyl" comprises groups like cyclopropyl, cyclobutyl, cyclopentyl, cyclohexyl and cycloheptyl. The term "$C_5$-$C_7$-Cycloalkenyl" relates to a 1, 2 oder 3-cyclopentenyl ring, a 1, 2, 3 oder 4-cyclohexenyl ring or a 1, 2, 3, 4 or 5-cycloheptenylring.

Preferably $R^1$ is methyl, ethyl, —CH(CH$_3$)$_2$, propyl, iso-propyl, —CH$_2$—CH(CH$_3$)$_2$, butyl, isobutyl, tert.-butyl, —CH$_2$—C(CH$_3$)$_3$, pentyl, hexyl, —CH$_2$—C$_6$H$_5$, —CH$_2$—Cl, —CH$_2$—Br, —CH$_2$—F, —CH$_2$—I, —CH$_2$—N$_3$, —CH$_2$—C≡CH, —CH$_2$CH=CH$_2$CH$_3$ or —CH$_2$-cycloC$_3$H$_5$.

In another preferred embodiment of the present invention the culture media used for heterologous expression of the synthetase comprises at least one D- or L-amino acid of the general formulae (II) $R^2$—CHNH$_2$—CO$_2$H, wherein $R^2$ can be selected from the group comprising
substituted and non-substituted $C_1$-$C_{50}$-alkyl, substituted and non-substituted $C_2$-$C_{50}$-alkenyl, substituted and non-substituted $C_2$-$C_{50}$-alkinyl, substituted and non-substituted $C_3$-$C_{10}$-cycloalkyl, substituted and non-substituted $C_5$-$C_7$-cycloalkenyl, which in each case can be interrupted by one or more oxygen atoms, sulphur atoms, substituted or mono-substituted nitrogen atoms, double bonds and/or by one or more groups of the type —C(O)O—, —OC(O)—, —C(O)—, —NHC(O)O—, —OC(O)NH— and/or —OC(O)O—. In particular $R^2$ is —CH$_2$—C$_6$H$_5$ (phenyl), —CH$_2$—CH(CH$_3$)$_2$, —CH$_2$(CH$_3$)$_2$.

Thus, the amino acid may be fed to the culture media during growth of the expression host. The feeding of an amino acid to the culture media has only supportive character and improves the overall expression yield. It is however also possible (and common) that at least some of the amino acids, preferably the naturally occurring amino acids, are synthesized by the expression host itself.

Before transformation into the expression host the expression cassette is part of a plasmid vector.

An example for such a plasmid vector comprising an expression cassette with an Enniatin synthase is shown in FIG. 3. In this particular plasmid vector the Esyn gene (Enniatin synthetase) was cloned into Tet-On expression vector pVG2.2. Due to the large gene (9.4 kb) the cloning was performed by SLIC and homologous recombination method using pyrG as selection marker. However, other suitable cloning techniques are also applicable.

The integration process of the expression cassette into the chromosome of fungi, such as *A. niger* is exemplarily shown in FIG. 4. Integration into the genome can be by homologous or heterologous recombination thus resulting in transformants carrying either single- or multi-copy integrations of the expression cassette.

The present method allows for synthesizing at least one cyclodepsipeptide or a derivative thereof comprising the following general formulae (III)

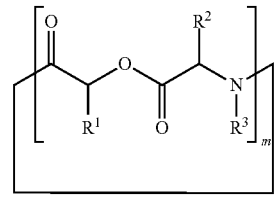

wherein $R^1$ and $R^2$ have the above meanings, $R^3$ is a C1-C3 alkyl moiety, in particular a —CH$_3$ moiety and m=3 or 4. Preferred Cyclodepsipeptides are shown in FIG. 10. In FIG. 11 the analytical data of Chloroenniatin obtained by feeding chlorolactate are shown.

Preferred variants are
Cyclo(-N-methyl-L-valyl-D-3-chlorolactyl-N-methyl-L-valyl-D-3-chlorolactyl-N-methyl-L-valyl-D-3-chlorolactyl-) ([3 Cl-Lac]3 Enniatin B)
Cyclo(-N-methyl-L-valyl-D-3-chlorolactyl-N-methyl-L-valyl-D-3-chlorolactyl-N-methyl-L-valyl-D-lactyl-) ([3 Cl-Lac]$_2$ [Lac]$_1$ Enniatin B)
Cyclo(-N-methyl-L-valyl-D-3-chlorolactyl-N-methyl-L-valyl-D-lactyl-N-methyl-L-valyl-D-lactyl-) ([3 Cl-Lac]$_1$ [Lac]$_2$ Enniatin B)
Cyclo(-L-valyl-D-3-chlorolactyl-N-methyl-L-valyl-D-3-chlorolactyl-N-methyl-L-valyl-D-3-chlorolactyl-) ([3 Cl-Lac]$_3$ Enniatin B 2)
Cyclo(-N-methyl-L-valyl-D-3-bromolactyl-N-methyl-L-valyl-D-3-bromolactyl-N-methyl-L-valyl-D-3-bromolactyl) ([3 Br-Lac]2 [Lac]1 Enniatin B)
Cyclo(-N-methyl-L-valyl-D-3-bromolactyl-N-methyl-L-valyl-D-3-bromolactyl-N-methyl-L-valyl-D-lactyl-) ([3 Br-Lac]$_2$ [Lac]$_1$ Enniatin B)
Cyclo(-N-methyl-L-valyl-D-3-bromolactyl-N-methyl-L-valyl-D-lactyl-N-methyl-L-valyl-D-lactyl-) ([3 Br-Lac]$_1$ [Lac]$_2$ Enniatin B)
Cyclo(-L-valyl-D-3-bromolactyl-N-methyl-L-valyl-D-3-bromolactyl-N-methyl-L-valyl-D-3-bromolactyl-) ([3 Br-Lac]$_3$ Enniatin B 2)
Cyclo(-L-valyl-D-3-bromolactyl-N-methyl-L-valyl-D-3-bromolactyl-N-methyl-L-valyl-D-2-hydroxyisovaleryl-) ([3 Br-Lac]$_2$ [D-Hiv]$_1$ Enniatin B)
Cyclo(-L-valyl-D-3-bromolactyl-N-methyl-L-valyl-D-2-hydroxy-lactyl-N-methyl-L-valyl-D-2-hydroxy-isovaleryl-) ([3 Br-Lac]$_1$ [D-Hiv]$_2$ Enniatin B)
Cyclo(-N-methyl-L-valyl-D-3-azidolactyl-N-methyl-L-valyl-D-3-azidolactyl-N-methyl-L-valyl-D-3-azidolactyl-) ([3 N3-Lac]$_3$ Enniatin B)
Cyclo(-N-methyl-L-valyl-D-3-azidolactyl-N-methyl-L-valyl-D-3-azidolactyl-N-methyl-L-valyl-D-lactyl-) ([3 N3-Lac]$_2$ [Lac]$_1$ Enniatin)
Cyclo(-N-methyl-L-valyl-D-3-fluorolactyl-N-methyl-L-valyl-D-3-fluorolactyl-N-methyl-L-valyl-D-3-fluorolactyl-) ([3 F-Lac]$_3$ Enniatin B)

Cyclo(-N-methyl-L-valyl-D-3-fluorolactyl-N-methyl-L-valyl-D-3-fluorolactyl-N-methyl-L-valyl-D-3-fluorolactyl-) ([3 F-Lac]$_2$ [Lac]$_1$ Enniatin B)

Cyclo(-N-methyl-L-valyl-D-3-iodolactyl-N-methyl-L-valyl-D-3-iodolactyl-N-methyl-L-valyl-D-3-iodolactyl-) ([3 I-Lac]$_3$ Enniatin B)

Cyclo(-N-methyl-L-valyl-D-3-iodolactyl-N-methyl-L-valyl-D-3-iodolactyl-N-methyl-L-valyl-D-lactyl-) ([3 I-Lac]$_2$ [Lac]$_1$ Enniatin B)

Cyclo(-N-methyl-L-valyl-D-3-iodolactyl-N-methyl-L-valyl-D-lactyl-N-methyl-L-valyl-D-lactyl-) ([3 I-Lac]$_1$ [Lac]$_2$ Enniatin B)

Cyclo(-N-methyl-L-valyl-D-3-cyclopropyllactyl-N-methyl-L-valyl-D-3-cyclopropyllactyl-N-methyl-L-valyl-D-3-cyclopropyllactyl-) ([3 Cp-Lac]$_3$ Enniatin B)

Cyclo(-N-methyl-L-valyl-D-3-bromolactyl-N-methyl-L-valyl-D-3-chlorolactyl-N-methyl-L-valyl-D-3-chlorolactyl-) ([3 Br-Lac]$_1$ [3 Cl Lac]$_2$ Enniatin B)

Cyclo(-N-methyl-L-valyl-D-3-bromolactyl-N-methyl-L-valyl-D-3-bromolactyl-N-methyl-L-valyl-D-3-chlorolactyl-) ([3 Br-Lac]$_2$ [3 Cl Lac]$_1$ Enniatin B)

Cyclo(-N-methyl-L-valyl-D-propagyllactat-N-methyl-L-valyl-D-propagyllactat-N-methyl-L-valyl-D-propagyllactyl-) ([3 Pr-Lac]$_3$ Enniatin B)

Cyclo(-N-methyl-L-valyl-D-3-bromolactyl-N-methyl-L-valyl-D-3-chlorolactyl-N-methyl-L-valyl-D-3-lactyl-) ([3 Br-Lac]$_1$ [3 Cl Lac]$_1$ [Lac]$_1$ Enniatin B)

Cyclo(-L-valyl-d$_6$-D-2-hydroxy-isovaleryl-N-methyl-L-valyl-d$_8$-D-2-hydroxy-isovaleryl-N-methyl-L-valyl-d$_6$-D-2-hydroxy-isovaleryl-) (d$_{18}$ Enniatin B)

Cyclo (—N-methyl-L-phenylalanyl-D-phenyllactyl-N-methyl-L-phenylalanyl-D-phenyllactyl-N-methyl-L-phenylalanyl-D-phenyllactyl-) ([Phelac]$_3$ Beauvericin)

Cyclo (—N-methyl-L-valyl-D-phenyllactyl-N-methyl-L-valyl-D-phenyllactyl-N-methyl-L-valyl-D-phenyllactyl-) ([Phelac]$_3$ Enniatin B)

Cyclo (—N-methyl-L-valyl-D-phenyllactyl-N-methyl-L-valyl-D-phenyllactyl-N-methyl-L-valyl-D-lactyl-) ([Phelac]2 [Lac]$_1$ Enniatin B)

Cyclo (—N-methyl-L-valyl-D-lactyl-N-methyl-L-valyl-D-lactyl-N-methyl-L-valyl-lactyl-) ([Lac]$_3$ Enniatin B)

Cyclo (—N-methyl-L-D-valyl-D-phenylalanyl-N-methyl-L-valyl-D-lactyl-N-methyl-L-valyl-D-lactyl-) ([Phelac]$_1$ [Lac]$_2$ Enniatin B)

Cyclo (—N-methyl-L-phenylalanyl-D-phenyllactyl-N-methyl-L-phenylalanyl-D-phenyllactyl-N-methyl-L-phenylalanyl-D-lactyl-) ([Phelac]$_2$ [Lac]$_1$ Beauvericin)

The chemical structures of some of the above and further variants are shown below:

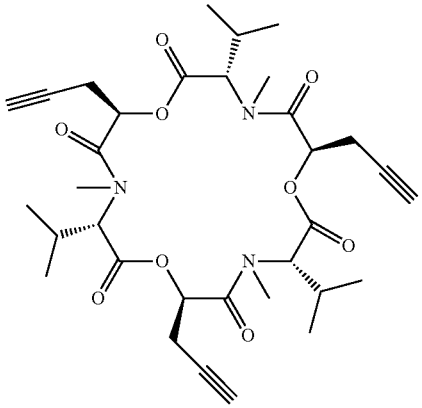

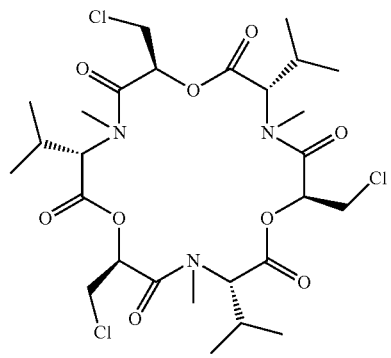

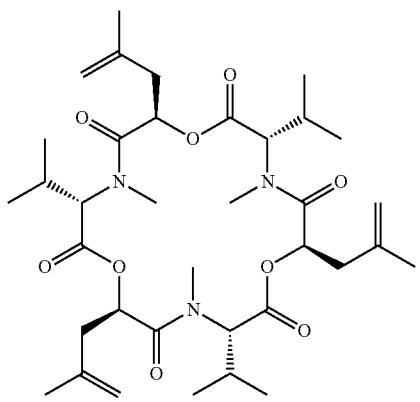

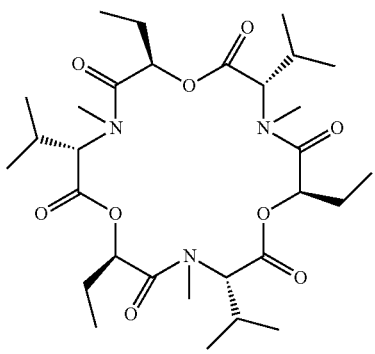

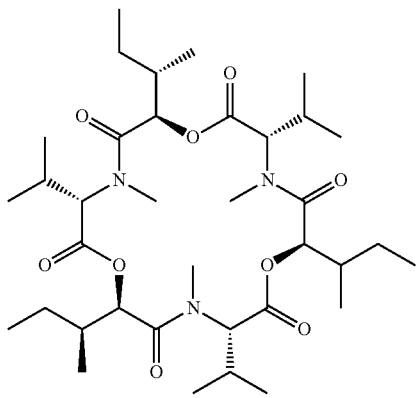

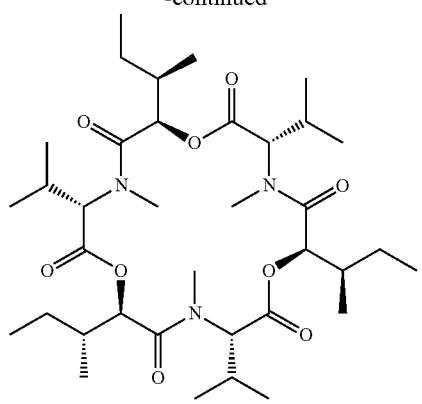
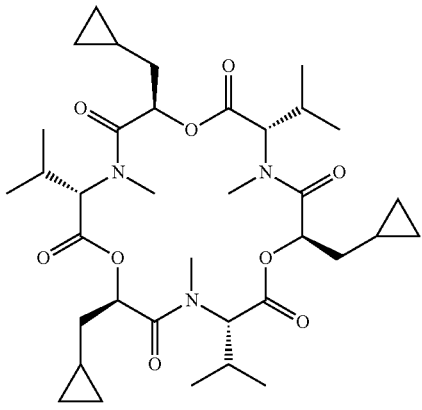
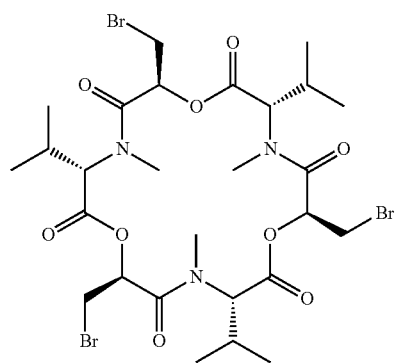
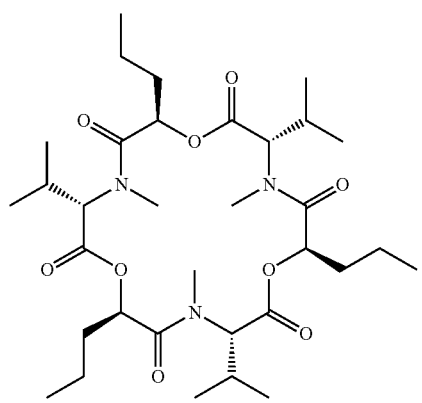
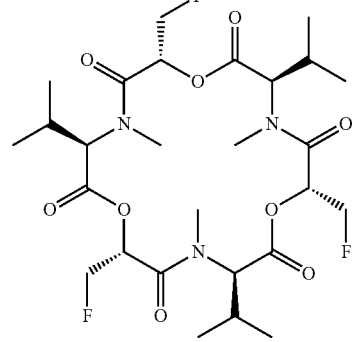
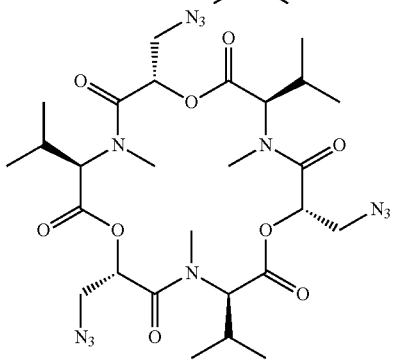
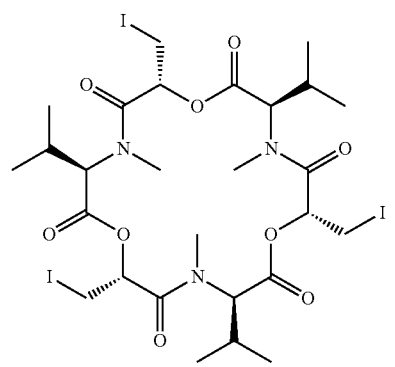
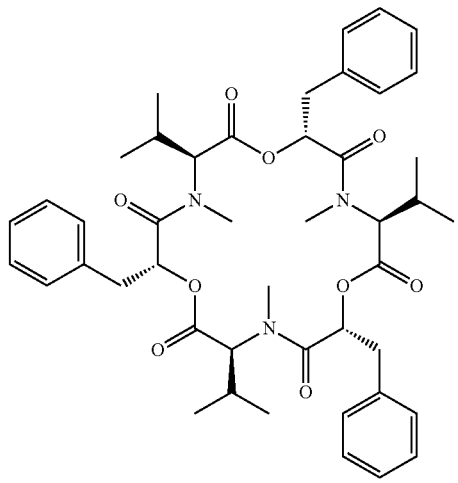
[PheLac]$_3$-enniatin

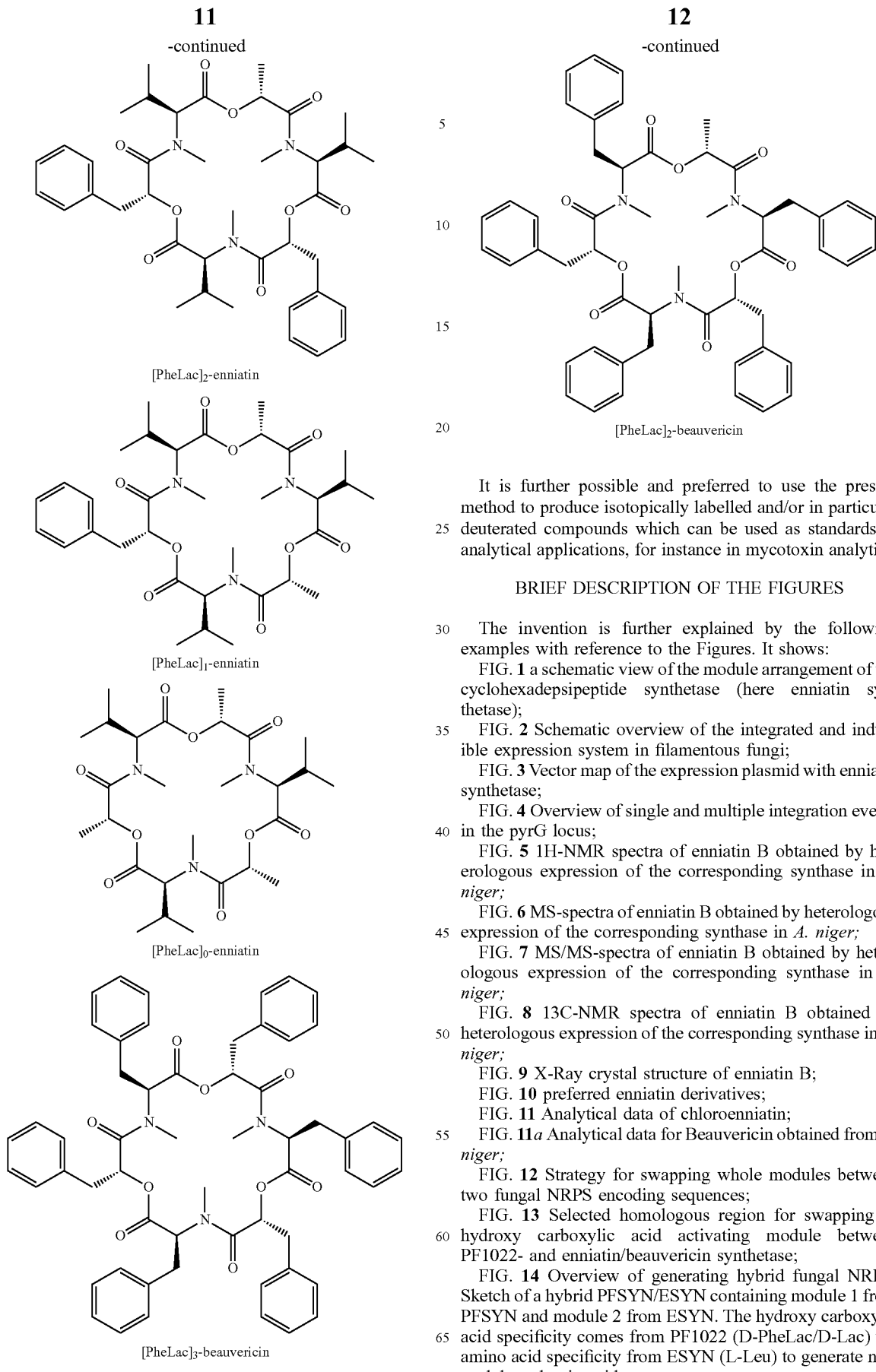

[PheLac]₂-enniatin

[PheLac]₁-enniatin

[PheLac]₀-enniatin

[PheLac]₃-beauvericin

[PheLac]₂-beauvericin

It is further possible and preferred to use the present method to produce isotopically labelled and/or in particular deuterated compounds which can be used as standards in analytical applications, for instance in mycotoxin analytics.

BRIEF DESCRIPTION OF THE FIGURES

The invention is further explained by the following examples with reference to the Figures. It shows:

FIG. 5 1H-NMR spectra of enniatin B obtained by heterologous expression of the corresponding synthase in *A. niger*;

Figure 13:
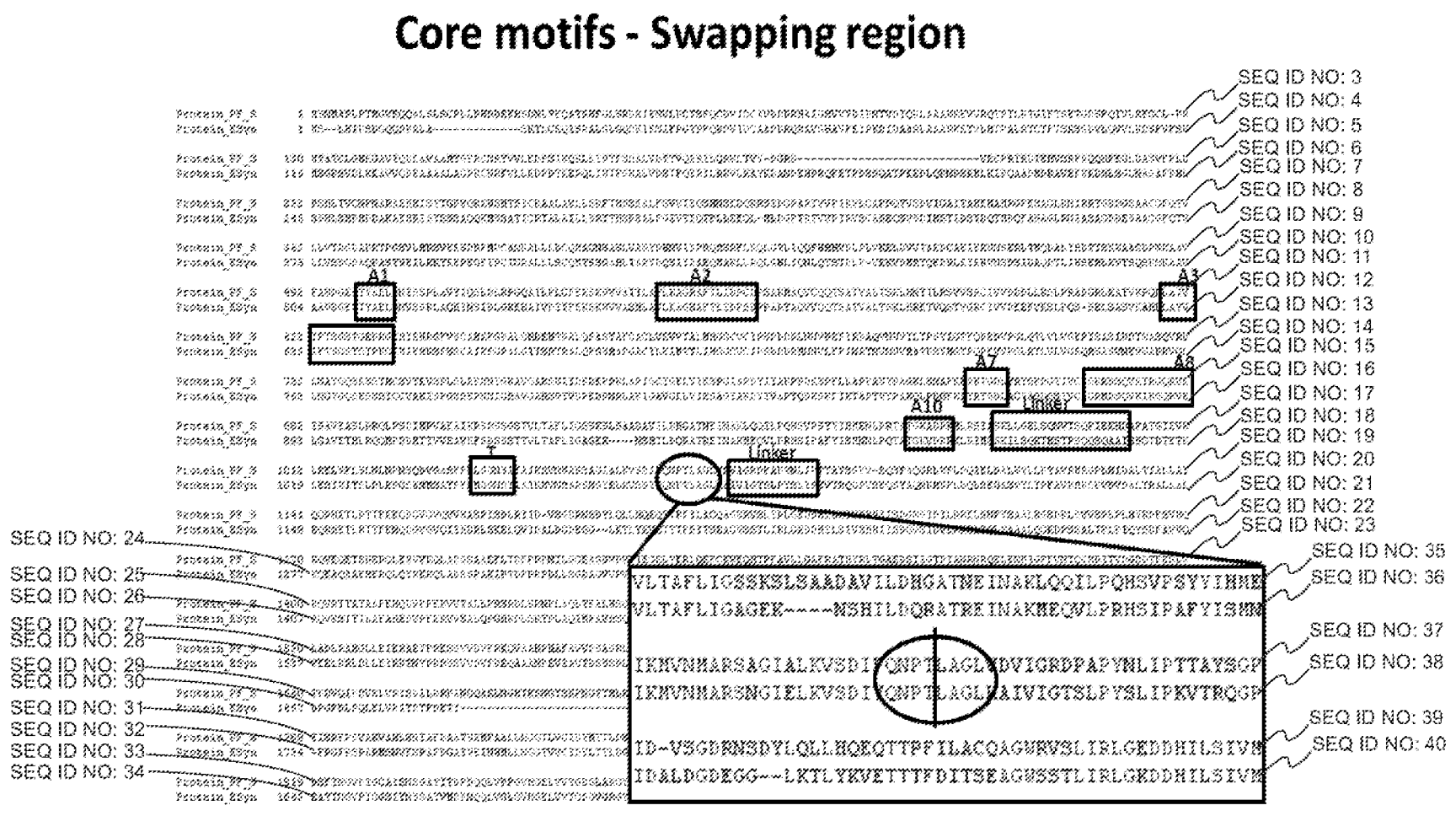

FIG. 8 13C-NMR spectra of enniatin B obtained by heterologous expression of the corresponding synthase in *A. niger*;

FIG. 13 Selected homologous region for swapping of hydroxy carboxylic acid activating module between PF1022- and enniatin/beauvericin synthetase;

FIG. 26 Polynucleotide sequence (SEQ ID NO: 1) of PF/Enniatin Chimeric Synthetase FIG. 27 Polynucleotide sequence (SEQ. ID NO: 2) of PF/Beauvericin Chimeric Synthetase

A. FILAMENTOUS FUNGI AS EXPRESSION HOST

1. Terms and Definitions

Host:
    A filamentous fungus belonging to the genera *Aspergillus, Trichoderma, Penicillium, Fusarium, Rhizopus*

Dependent Host:
    A host that is able to synthesize cyclodepsipeptides only if precursors (hydroxy acids) are added to the medium (example: *A. niger* strain DS3.1)

Independent Host:
    A host that is able to synthesize cyclodepsipeptides without addition of the precursors (example: *A. niger* strain ÖV3.4)

2. Protocol: PEG-Mediated Transformation of *A. niger*

Figure 1:
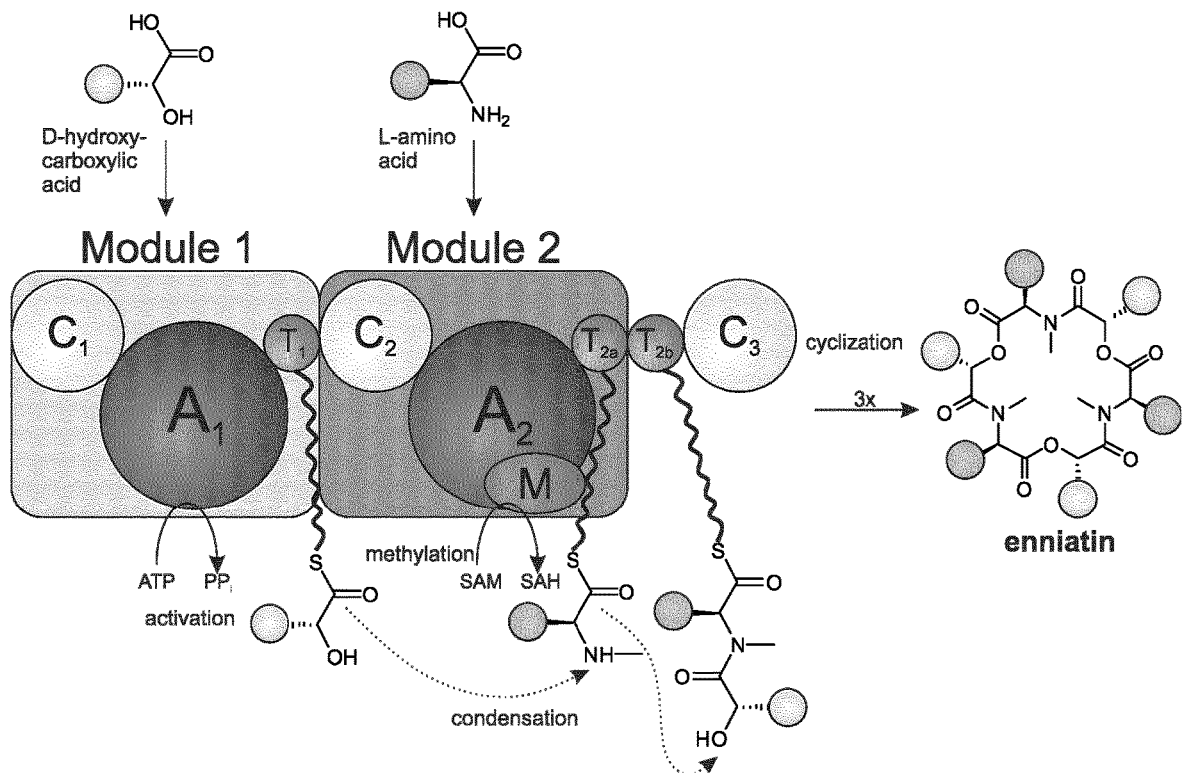
FIG. 1 a schematic view of the module arrangement of the cyclohexadepsipeptide synthetase (here enniatin synthetase)
Figure 2:
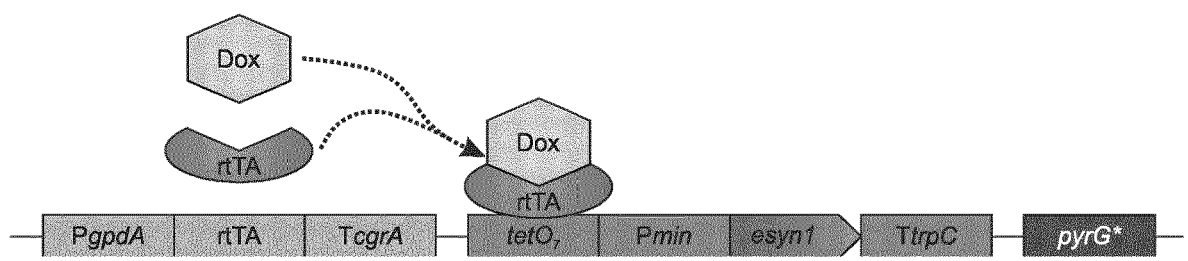
FIG. 2 Schematic overview of the integrated and inducible expression system in filamentous fungi.
Figure 3:
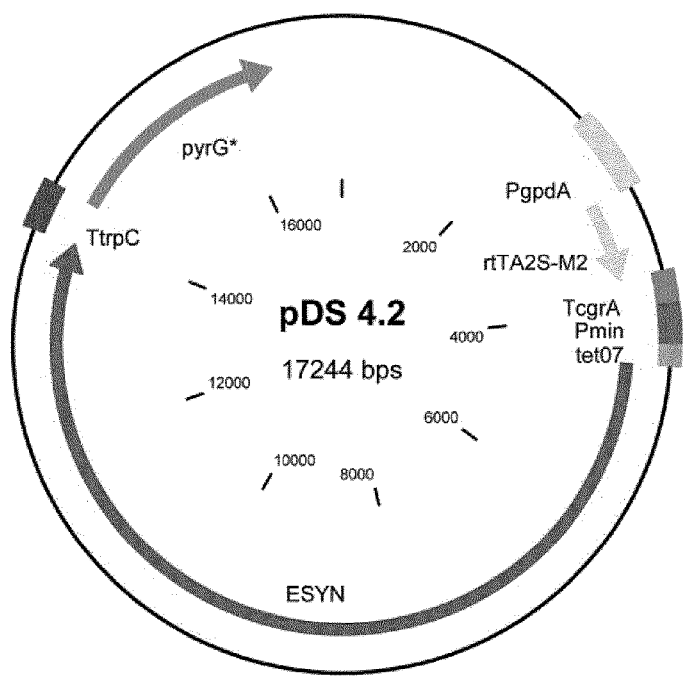
FIG. 3 Vector map of the expression plasmid with enniatin synthetase.
Figure 4:
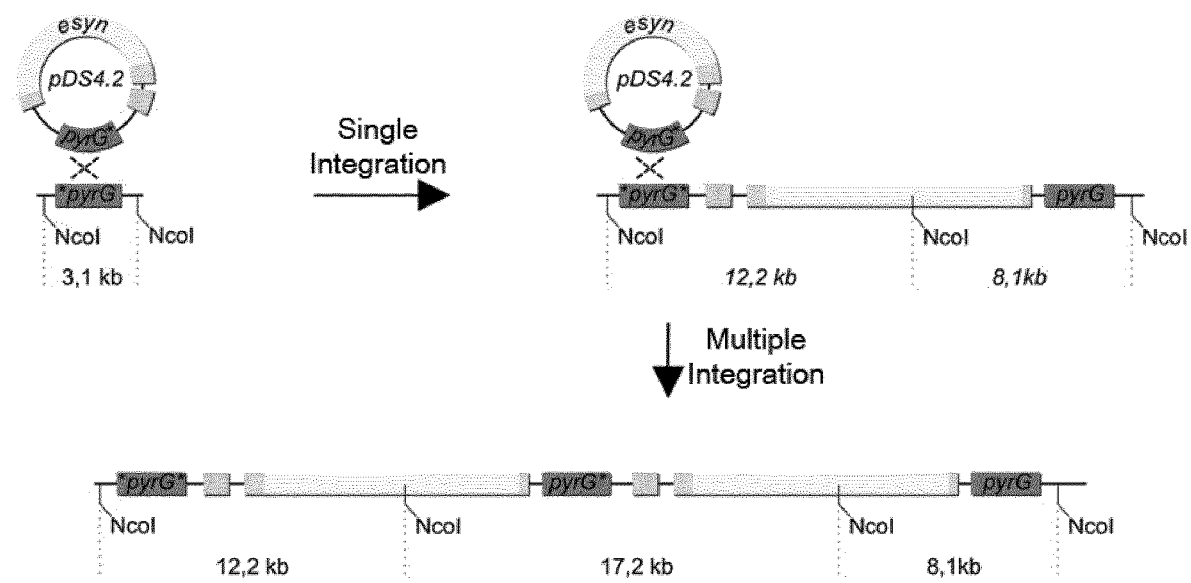
FIG. 4 Overview of single and multiple integration events in the pyrG locus.
Figure 5:
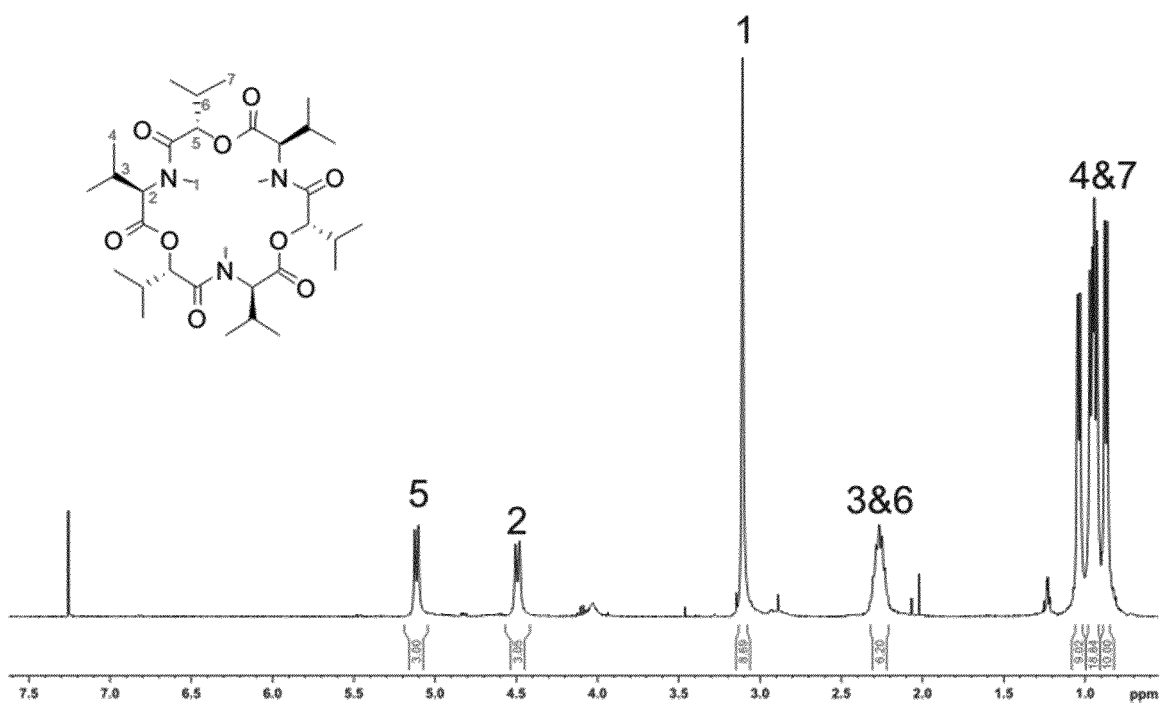
Figure 6:
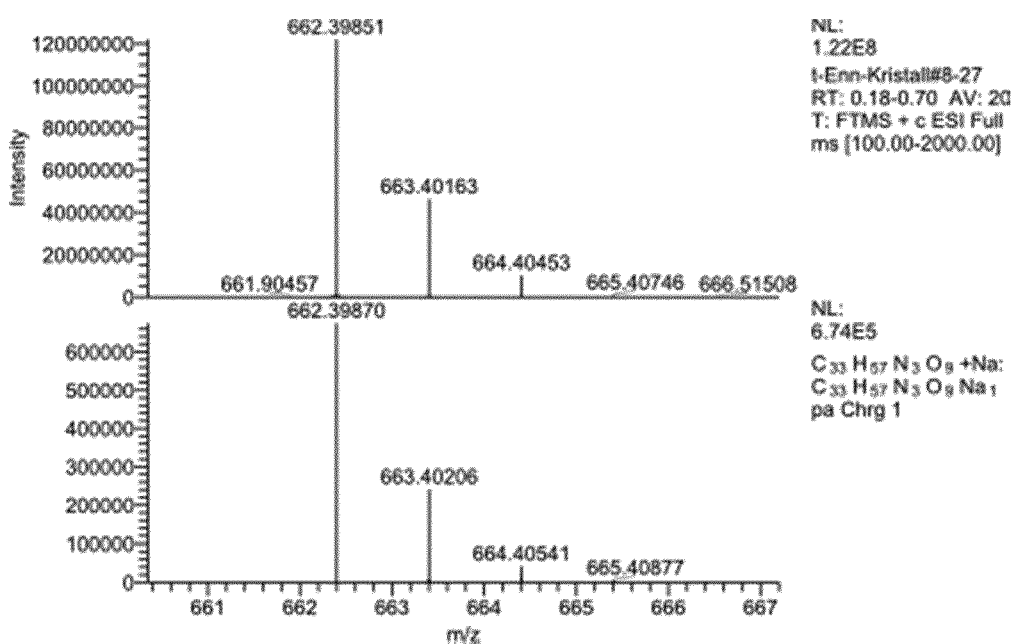
FIG. 6 MS-spectra of enniatin B obtained by heterologous expression of the corresponding synthase in *A. niger*.
Figure 7:
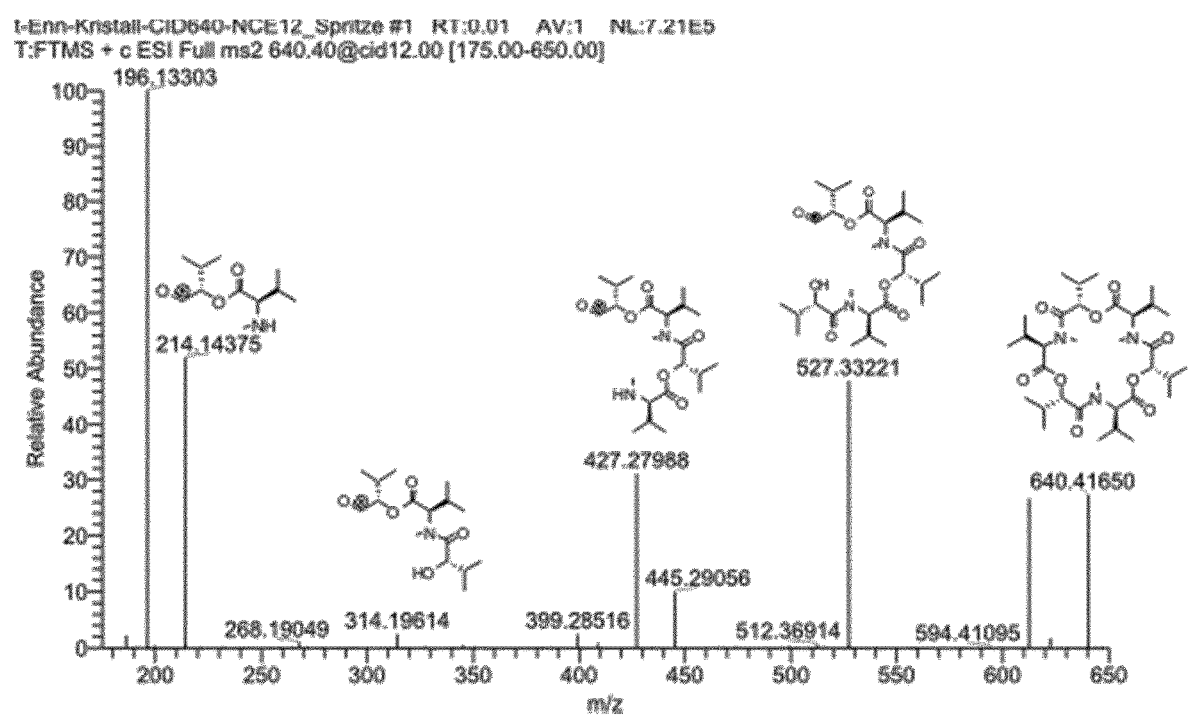
FIG. 7 MS/MS-spectra of enniatin B obtained by heterologous expression of the corresponding synthase in *A. niger*.
Figure 8:
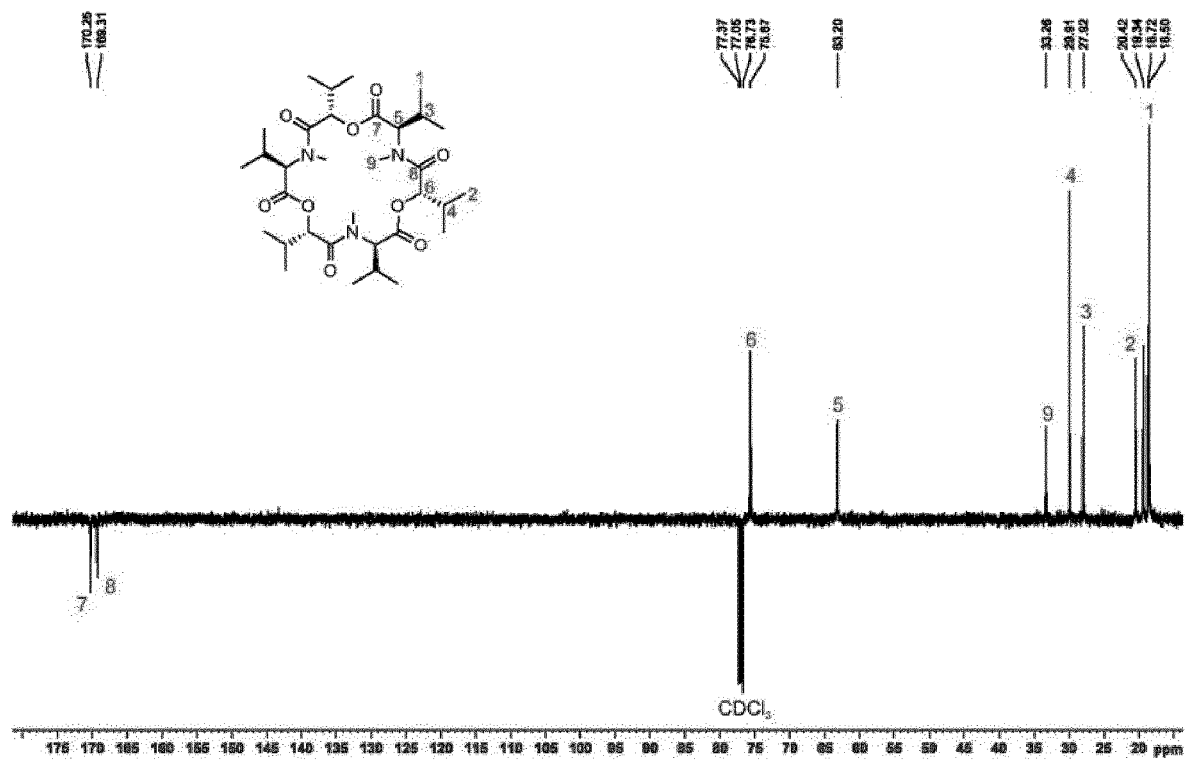
Figure 9:
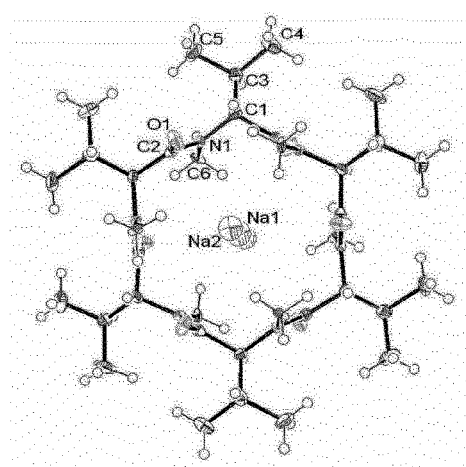
FIG. 9 X-Ray crystal structure of enniatin B.
Figure 10:
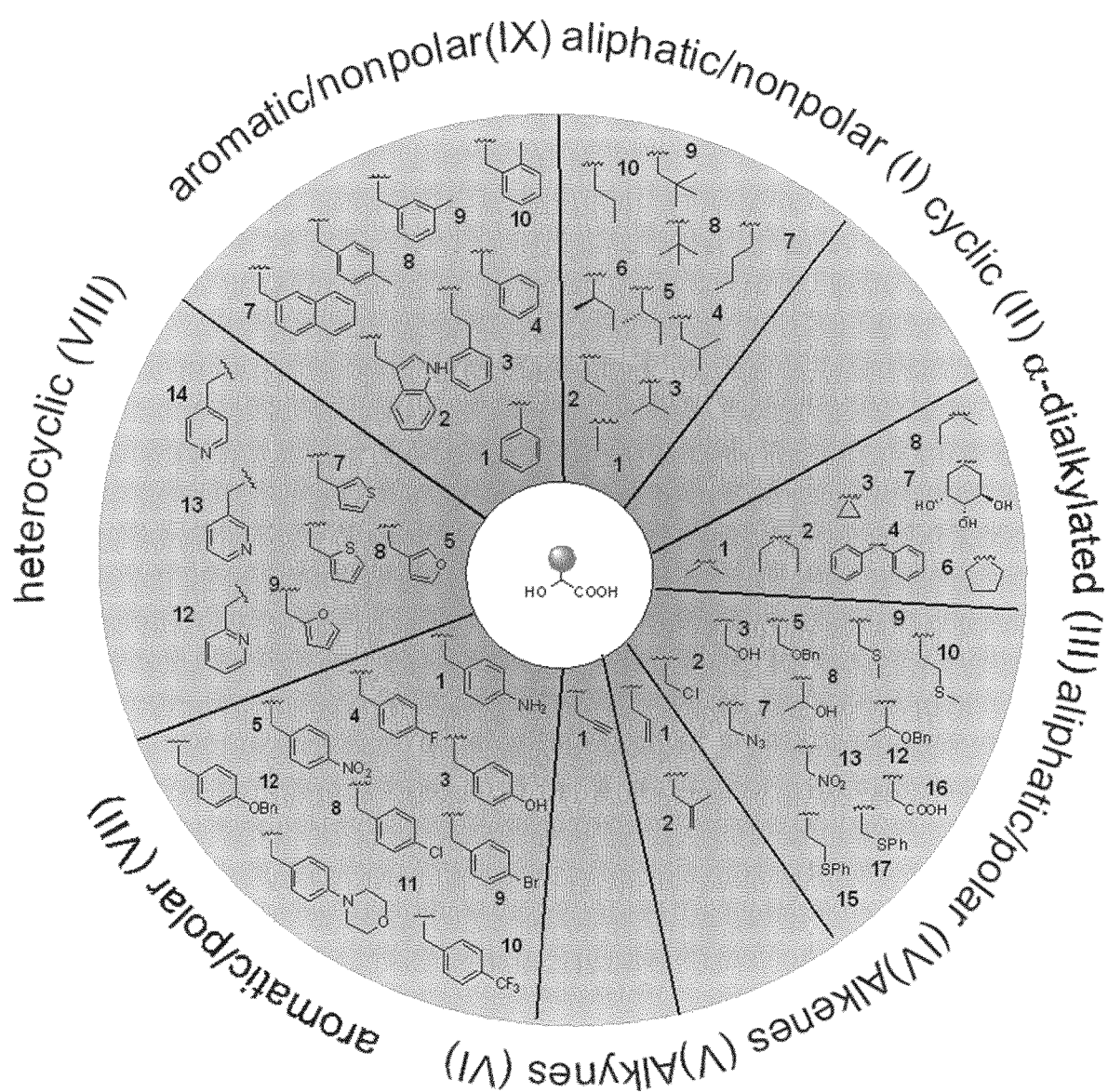
FIG. 10 preferred enniatin derivatives.

The esyn1 gene of *F. oxysporum* was integrated in plasmid pVG2.2 to give plasmid pDS4.2 (FIG. 3) which comprises all three components of the Tet-on system:PgpdA:: rtTA2S-M2 for constitutive expression of the transactivator rtTA, tetO7::Pmin::esyn1, which mediates esyn1 expression in a Dox-dependent manner and the pyrG* cassette, necessary for selection and targeting of the system to the pyrG locus of *A. niger*.

The performed transformation of *A. niger* is based on the method described by Punt et al. The used recipient strains were protease-negative (prtT) and uracil-auxotroph (pyrG$^-$). The used constructs carry a mutated pyrG gene (pyrG*), which allows the transformants to grow on medium lacking uridine only after uptake of the foreign DNA and after homologous recombination of pyrG* with a mutated pyrG gene version of *A. niger* (both mutations are at different locations). The enniatin synthetase was expressed under control of the Tet-On expression system.

3. Materials and Solutions

SMC: 1.33 M sorbitol
    50 mM CaCl$_2$
    20 mM MES Buffer
    pH 5.8
TC: 50 mM CaCl$_2$
    10 mM Tris/HCl
    pH 7.5
STC: 1.33 M sorbitol in TC
PEG buffer: 7.5 g PEG-6000
    TC up to 30 mL
ASP+N (50×): 350 mM KCl
    550 mM KH$_2$PO$_4$
    3.5 M NaNO$_3$
    pH 5.5
Vishniac: 76 mM ZnSO4
    178 mM H$_3$BO$_3$
    25 mM MnCl$_2$
    18 mM FeSO$_4$
    7.1 mM CoCl$_2$
    6.4 mM CuSO$_4$
    6.2 mM NaMoO$_4$
    174 mM EDTA protoplastation solution: 250 mg lysing enzyme from *Trichoderma harzianum*
(Sigma)
SMC up to 10 mL
pH 5.6
MM: 20 mL ASP+N (50×)
20 mL glucose (50%)
2 mL MgSO$_4$
1 mL Vishniac
H$_2$O to 1 L
(addition of 2% agar for solid medium)
CM: MM, supplemented with:
10 mL casamino acids (10%)
50 mL yeast extract (10%)
H$_2$O to 1 L
(addition of 2% agar for solid medium)
Tranformation plates: 325.19 g sucrose
20 mL ASP+N
2 mL MgSO$_4$
1 mL Vishniac
12 g agar
Top agar: 325.19 g sucrose
20 mL ASP+N
2 mL MgSO$_4$
1 mL Vishniac
6 g agar 4. Experimental Procedure The recipient strains (e.g. MA169.4 or AB1.13) were cultured in 100 mL of CM (+10 mM uridine) at 30° C. and 120 rpm for 10-16 h. The mycelium was collected over a myracloth filter and washed once with SMC. Afterwards, the collected mycelium was added to the protoplastation solution (in 50 mL test tube) and incubated for 1-1.5 h at 37° C. and 80 rpm. The protoplastation was confirmed by microscopy. Then, the protoplasts were collected through a myracloth filter and washed once with STC. The suspension was centrifuged for 10 min at 10° C. and 2000 rpm. The supernatant was decanted and the pellet gently resuspended in 1 mL of STC. The suspension was transferred to an Eppendorf tube and centrifuged for 5 min at 10° C. and 6000 rpm. Again, the supernatant was decanted and the protoplasts resuspended in 1 mL of STC. The wash step was repeated twice. For each transformation, 100 µL of protoplasts, 10 µg plasmid pDS4.2 (in 10 µL H$_2$O) and 25 µL PEG buffer were added to a 50 mL test tube and mixed gently. 1 mL of PEG buffer was added and the tube mixed gently. After 5 min, 2 mL STC were added and mixed. 20-25 mL of top agar (cooled to 40° C.) were added to the mixture and poured onto the prepared transformation plates (Ø 15 cm). The plates were incubated at 30° C. for 3-4 days. Afterwards, the transformants were purified twice by streaking the spores on MM plates for colony isolation. The purified strains were analyzed by PCR and Southern Blot to confirm proper uptake and insertion of plasmid pDS4.2 into the genome of the recipient strains (see FIG. 3).

5. Analytical Data for the Dependent Host Mutant DS3.1 Synthesizing Enniatin and Chloroenniatin (FIGS. 9 5 to 11)

Cultivation Conditions:

In order to identify the optimum condition for high yield production of enniatin a design-of-experiment approach was followed using the statistical software program MODE. The following parameters were varied in shake flask cultures of esyn1-expressing strain DS3.1: medium composition (minimal medium, complete medium, *Fusarium* defined medium), amino acid (in particular L-valine, L-leucine, L-isoleucine) supplementation (0-20 mM), hydroxyacid (in particular D-Hiv) supplementation, 0-50 mM), glucose concentration (1-5%), temperature, cultivation time (1-92 h) and Dox-concentration (0-20 µg/ml). The parameters which mainly affected the enniatin yields were Dox and D-Hiv. The best cultivation medium identified contained 20 mM D-Hiv, 20 mM of one of the amino acids and 10 µg/ml Dox. This medium composition improved the enniatin yield by a factor of 200. The enniatin yield was further increased about 4.75 fold by increasing the glucose concentration to 5% and by adding talcum.

Enniatin Production Medium (EM): 20 mL ASP+N (50×)
100 mL glucose (50%)
2 mL MgSO$_4$
1 mL Vishniac
10 mL casamino acids (10%)
50 mL yeast extract (10%)
100 mL talc (10% in 50 mM Na-acetate buffer, pH 6.5)
H$_2$O to 1 L Strain DS3.1 (inoculation with $5\times10^6$ spores/mL) was cultivated in EM at 26° C. and 250 rpm. After 16 h, 10 mM or 20 mM D-Hiv, 20 mM I-Val and 10 µg/mL Dox were added. The biomass was harvested after 92 h, lyophilized and enniatin B extracted with ethyl acetate.

Analytical Methods (See FIGS. 5-9, 11):

$^1$H-NMR and $^{13}$C-NMR spectra of enniatin B were recorded on a Bruker Avance 400 NMR-spectrometer. Chemical shifts are given in δ-units (ppm) relative to the solvent signal. IR spectra were recorded on a Jasco FT-IR 4100 spectrometer. HRMS using ESI-technique was performed on a LTQ Orbitrap XL apparatus. The enniatin samples were directly infused into the mass spectrometer.

Data for single-crystal structure determination of enniatin B were collected on an Oxford-Diffraction Xcalibur diffractometer, equipped with a CCD area detector Sapphire S and a graphite monochromator utilizing MoK$_\alpha$ radiation (λ=0.71073 Å). Suitable crystals were attached to glass fibers using fluoropolyalkylether oil (ABCR) and transferred to a goniostat where they were cooled to 150 K for data collection. Software packages used: CrysAlis CCD for data collection, CrysAlis Pro for cell refinement and data reduction.

Results:

Enniatin B:

A production of enniatin B up to 1000 mg/L in strain DS3.1 could be obtained and verified by MRM-analysis.

393 mg of purified enniatin B could be isolated from the biomass (27.5 mg) and the broth of a 1-L cultivation of transformant DS3.1 with supplementation of 10 mM d-Hiv and 20 mM I-Val to the medium.

The isolated enniatin B was analyzed my MS, MS/MS, IR, NMR and X-Ray crystallography (see FIGS. 5-10):

$^1$H-NMR (400.1 MHz, CDCl$_3$) δ=5.11 (d, $^3J_{H,H}$=8.7 Hz, 3H), 4.49 (d, $^3J_{H,H}$=9.7 Hz, 3H), 3.11 (s, 9H), 2.32-2.21 (m, 6H), 1.05-0.86 ppm (m, 36H); $^{13}$C-NMR (100.6 MHz, CDCl$_3$) δ=170.25, 169.31, 75.67, 63.20, 33.26, 29.91, 27.92, 20.42, 19.34, 18.72, 18.50 ppm; IR (Neat): v=2963.6-2873.4 (C—H, CH$_3$ and CH), 1736.1 (C=O, ester), 1660.9 (C=O, amide), 1183.6 (C—H, isopropyl) 1011.0 (CO, α-hydroxycarboxylic acid); ESI-HRMS: m/z calcd for [C$_{33}$H$_{57}$N$_3$O$_9$+Na]$^+$: 662.39870; found: 662.39859.

Generation of Enniatin Analogs:
Protocol for Feeding Experiments:
Strain DS3.1 was cultivated under the same conditions as described above. Instead of D-Hiv, the corresponding hydroxy acid chlorolactate were added (10 mM final concentration). Feeding can be performed once or repeatedly at different time intervals during batch or fed batch cultivation.

Figure 11:
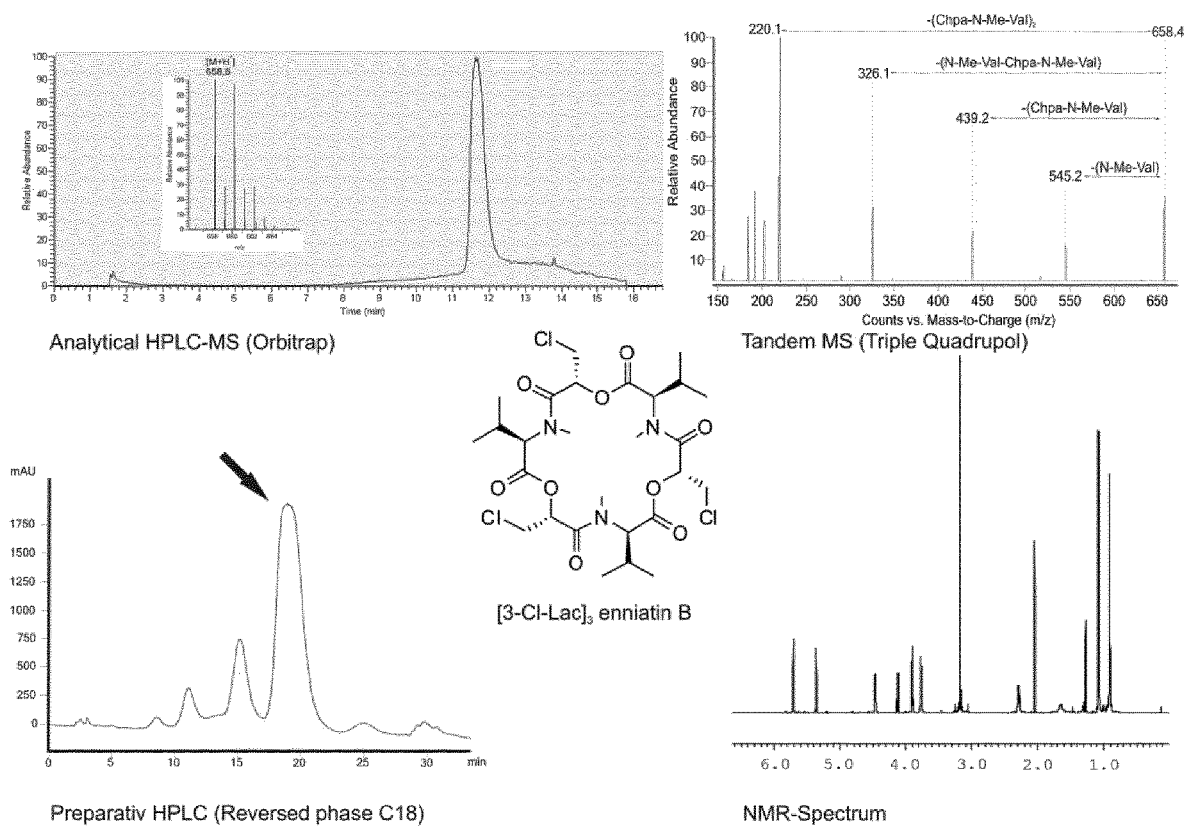
FIG. 11 Analytical data of chloroenniatin.
Figure 11A:
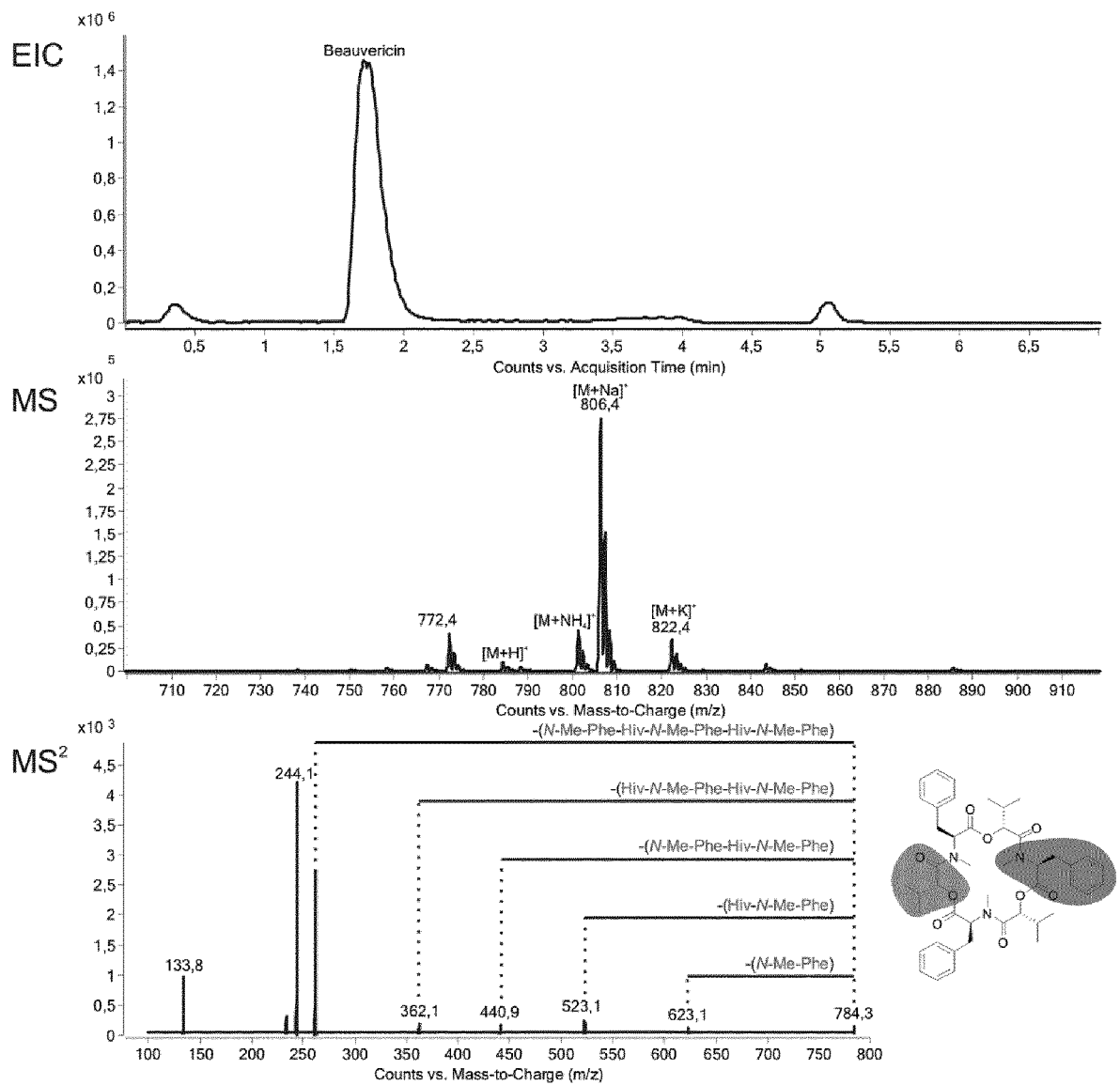
FIG. 11a Analytical data for Beauvericin obtained from *A. niger*.
Figure 12:
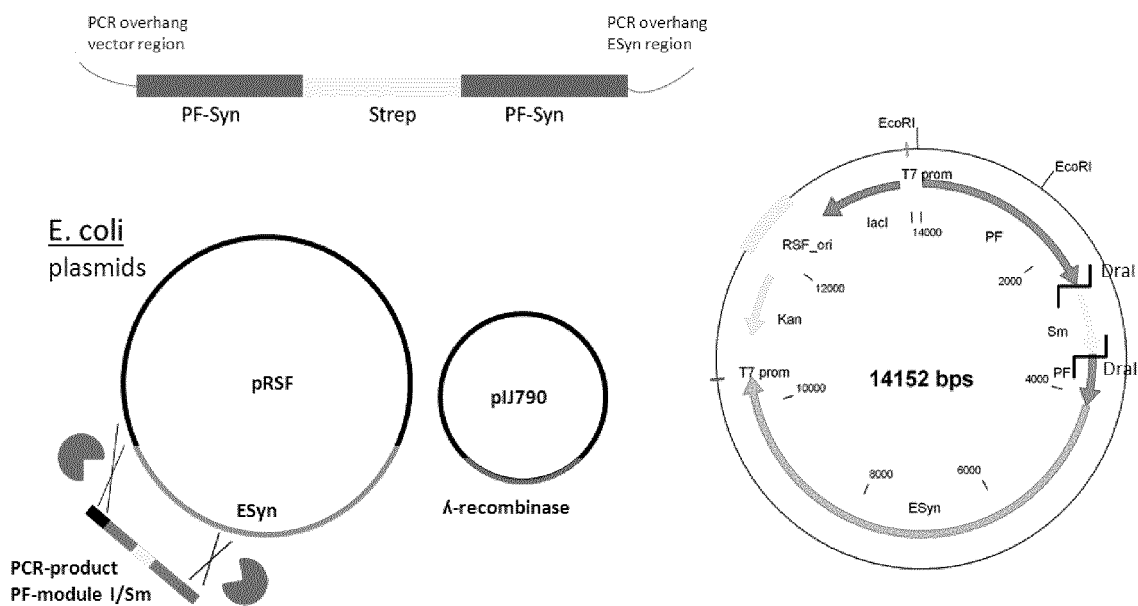
FIG. 12 Strategy for swapping whole modules between two fungal NRPS encoding sequences.
Figure 14:
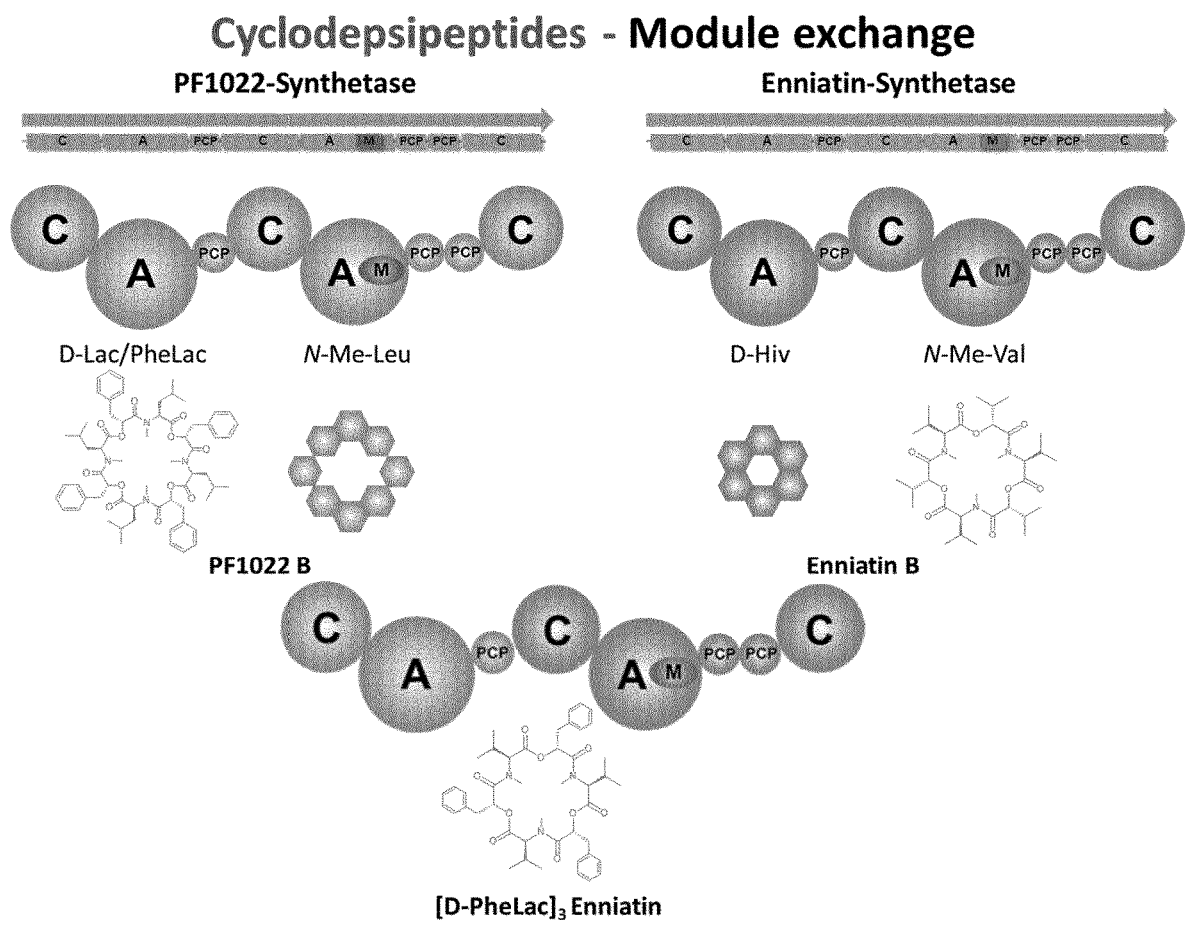
FIG. 14 Overview of generating hybrid fungal NRPS: Sketch of a hybrid PFSYN/ESYN containing module 1 from PFSYN and module 2 from ESYN. The hydroxy carboxylic acid specificity comes from PF1022 (D-PheLac/D-Lac) the amino acid specificity from ESYN (L-Leu) to generate new cyclohexadepsipeptides.
Figure 15:
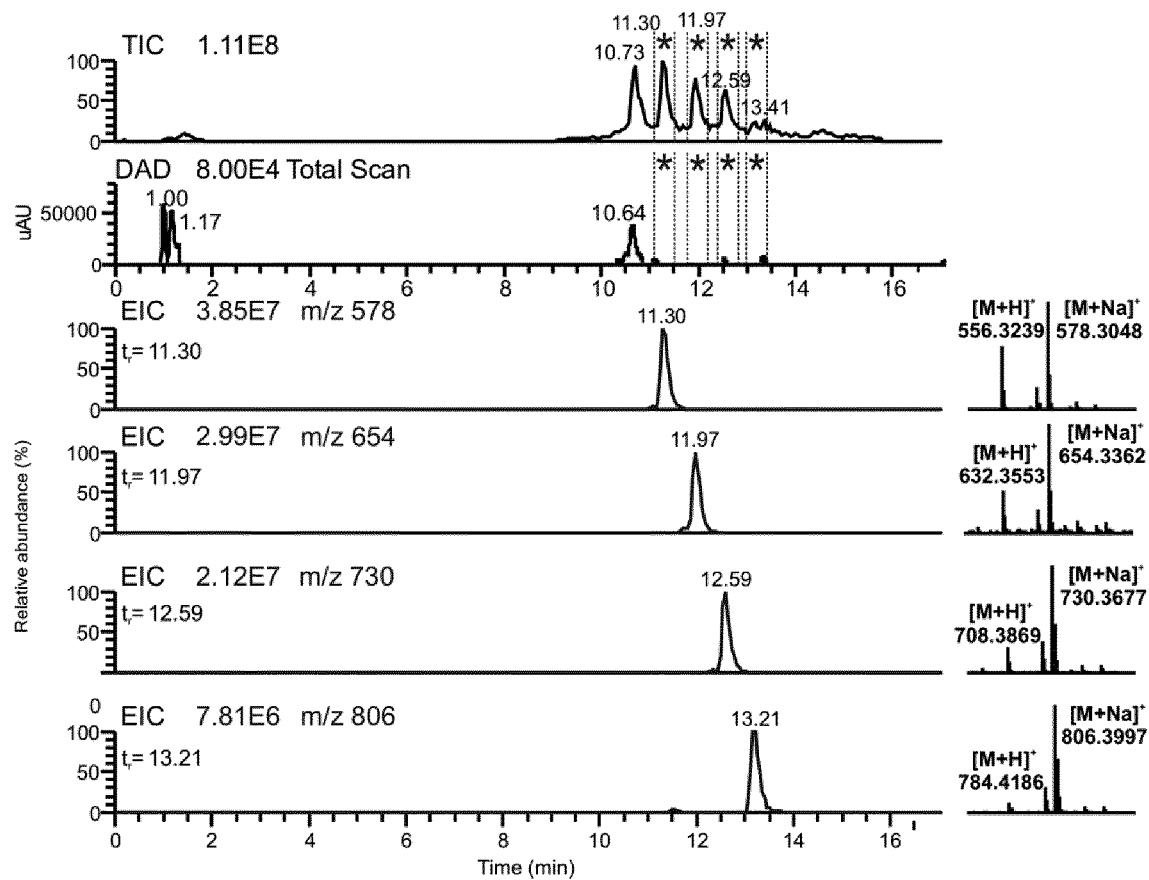
FIG. 15 HPLC-ESI-MS of chimeric [PheLac]$_{0-3}$-enniatin derivatives. Solvent A: water with 0.1% HCOOH, solvent B: acetonitrile with ACN mit 0.1% HCOOH. Flow rate: 0.2 mL/min. Measurements were performed with ESI-Orbitrap-MS, Exactive, Thermo Fisher Scientific, HPLC 1200 Series (Agilent Technologies) and a gradient from 5% to 100% from 1 to 8 min and subsequently 100% B for 5 more minutes. Column: Grace Grom-Sil 120 ODS-4 HE, 2×50 mm, 3 µm. TCC=20° C.
Figure 16:
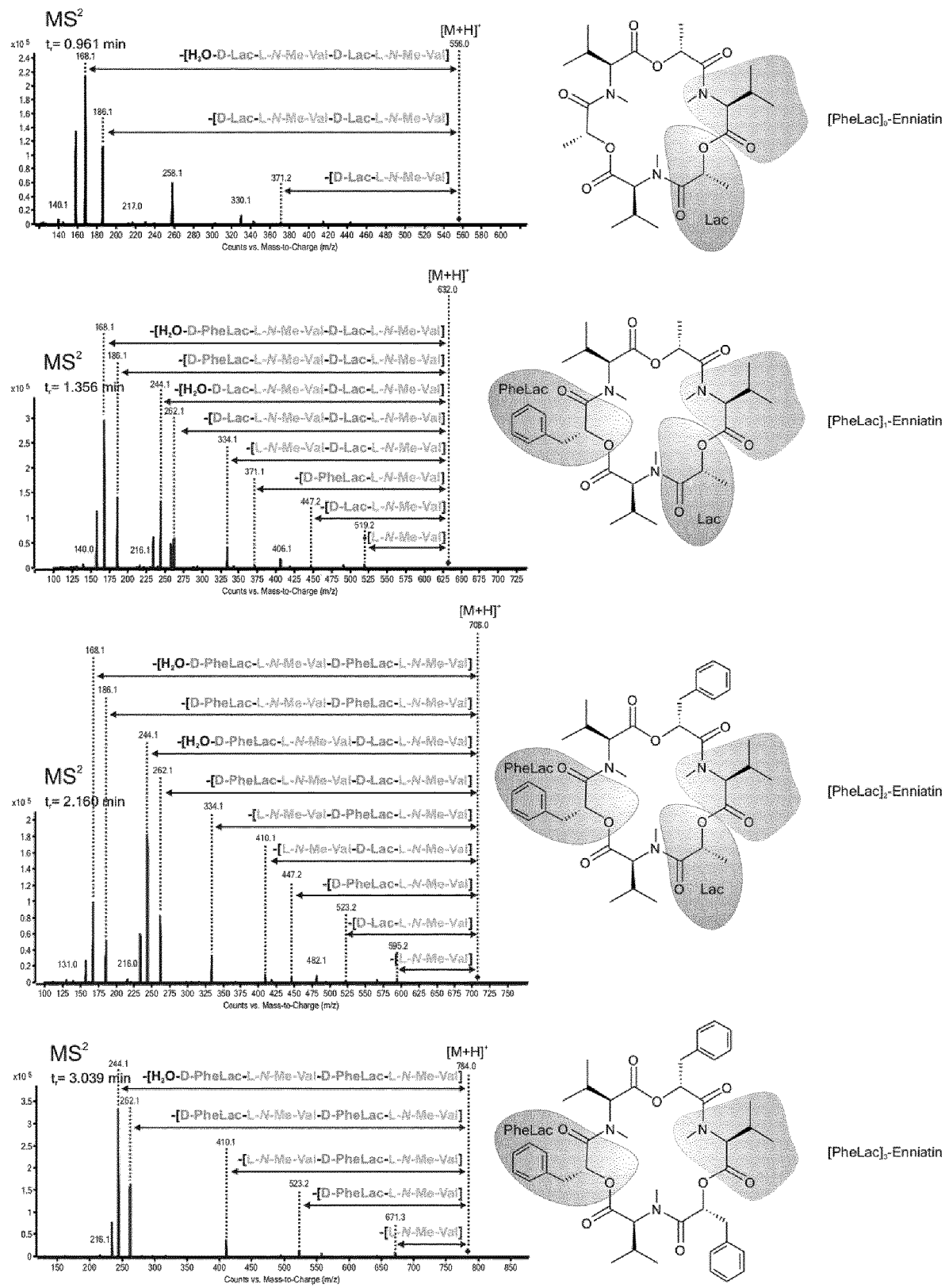
FIG. 16 Determination of identity of chimeric [PheLac]$_{0-3}$-enniatin cyclodepsipeptides by tandem MS measurements. m/z of fragments (cleavage at peptide or ester bonds) corresponds to loss of one or several amino or hydroxy acids as indicated. Solvent A: water, solvent B: isopropanol. Flow rate: 0.4 mL/min. Agilent Technologies ESI-Triple-Quadrupol-MS, 6460 Series, UHPLC 1290 Infinity-Series (Agilent Technologies). Column: Agilent Poroshell 120 EC-C18 3.0×50 mm. TCC=45° C.
Figure 17:
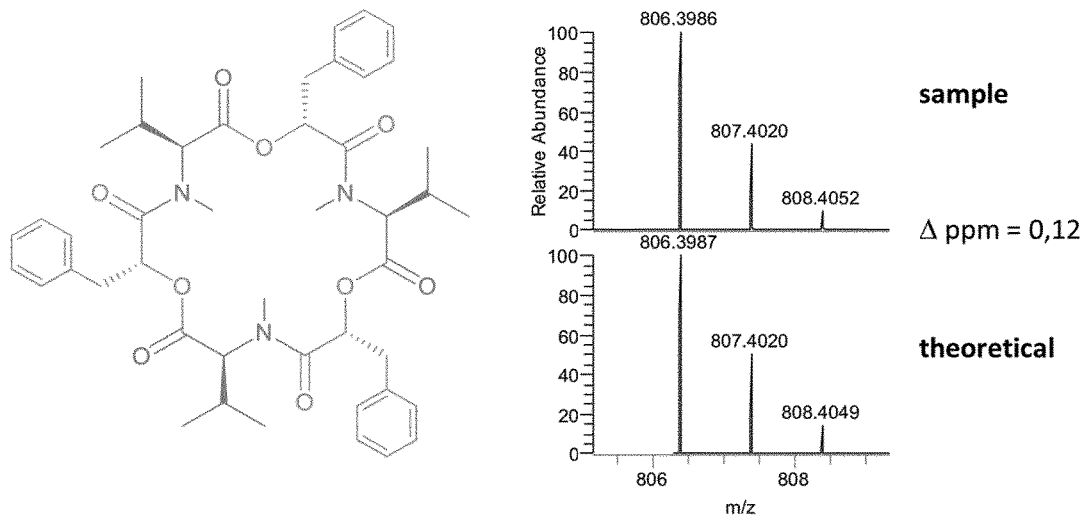
FIG. 17 Structure formula of [PheLac]$_3$-Enniatin and HR-ESI-Orbitrap MS for determination of the molecular formula.
Figure 18:
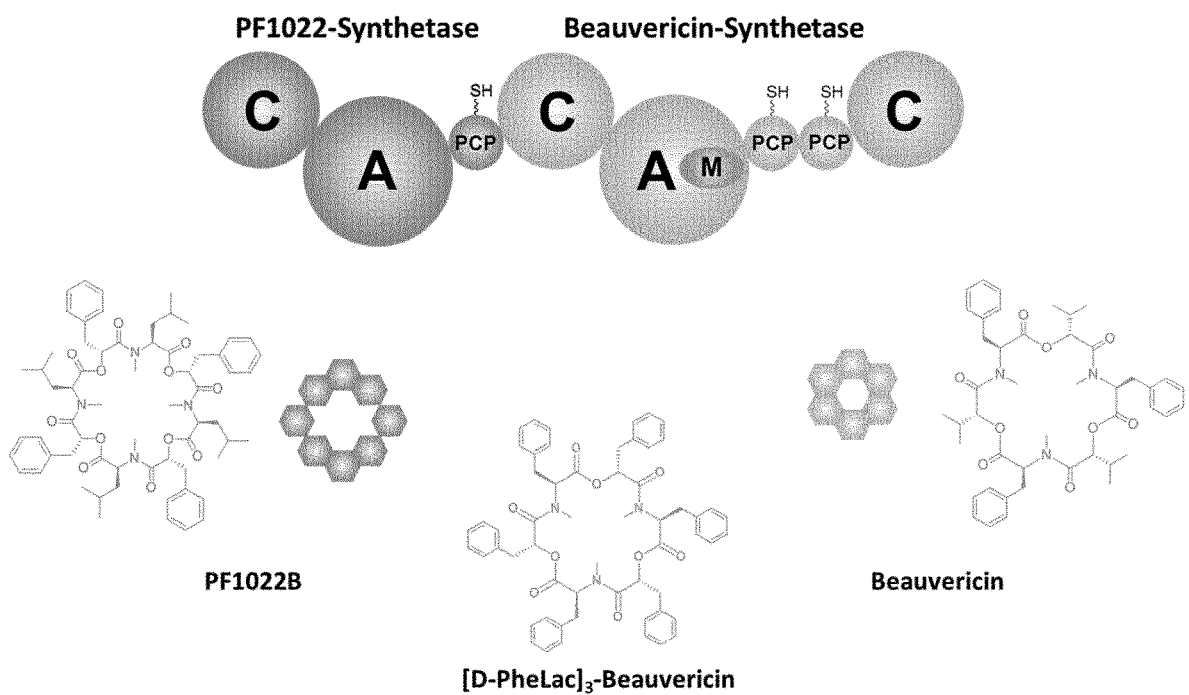
FIG. 18 Changing hydroxy carboxylic acid specification from beauvericin (D-Hiv) into PF1022 (D-PheLac/D-Lac)
Figure 19:
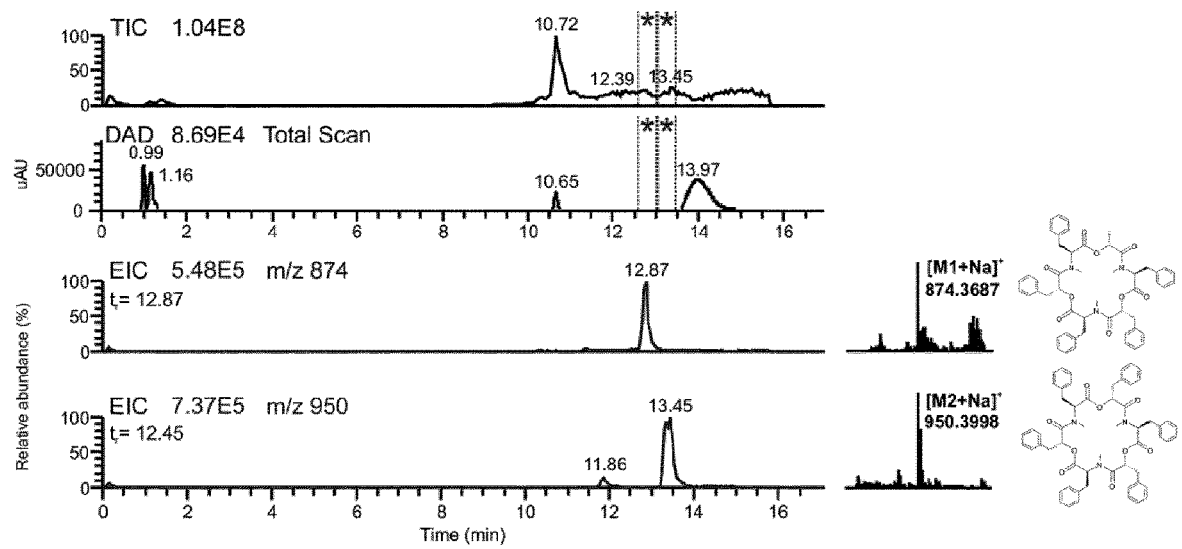
FIG. 19 HPLC-ESI-MS of chimeric [PheLac]$_{2-3}$-beauvericin derivatives. Solvent A: water with 0.1% HCOOH, solvent B: acetonitrile with ACN mit 0.1% HCOOH. Flow rate: 0.2 mL/min. Measurements were performed with ESI-Orbitrap-MS, Exactive, Thermo Fisher Scientific, HPLC 1200 Series (Agilent Technologies) and a gradient from 5% to 100% from 1 to 8 min and subsequently 100% B for 5 more minutes. Column: Grace Grom-Sil 120 ODS-4 HE, 2×50 mm, 3 µm. TCC=20° C.
Figure 20:
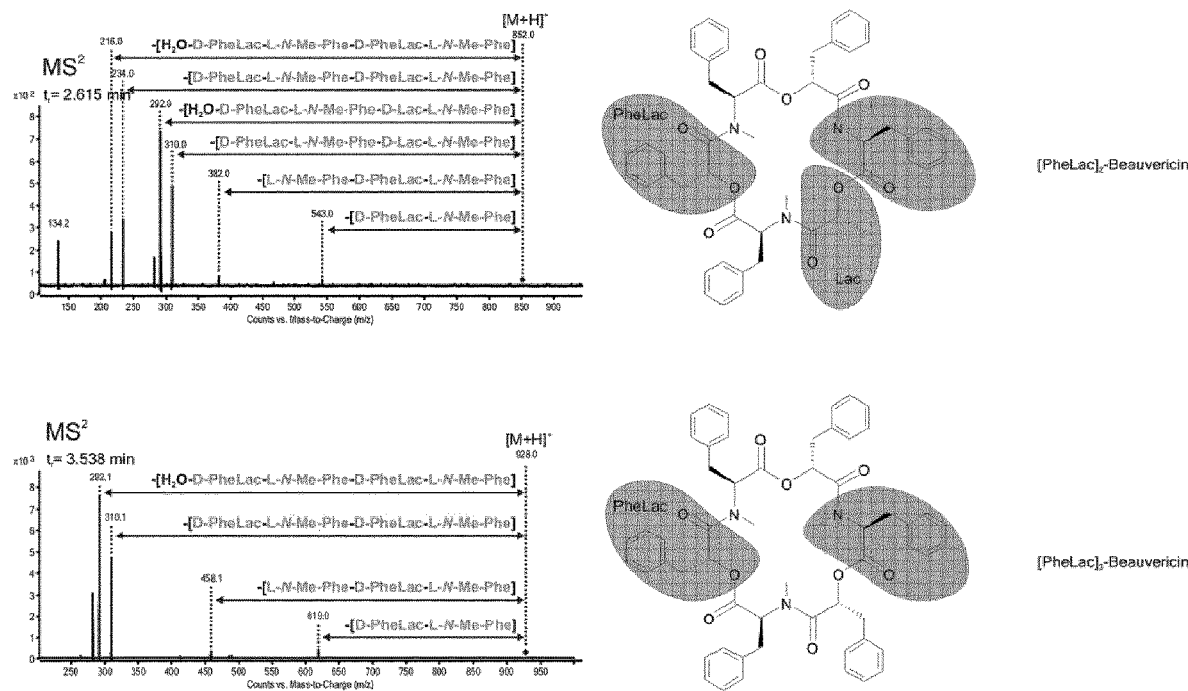
FIG. 20 Determination of identity of chimeric [PheLac]$_{2-3}$-beauvericin cyclodepsipeptides by tandem MS measurements. m/z of fragments (cleavage at peptide or ester bonds) corresponds to loss of one or several amino or hydroxy acids as indicated. Solvent A: water, solvent B: isopropanol. Flow rate: 0.4 mL/min. Agilent Technologies ESI-Triple-Quadrupol-MS, 6460 Series, UHPLC 1290 Infinity-Series (Agilent Technologies). Column: Agilent Poroshell 120 EC-C18 3.0×50 mm. TCC=45° C.
Figure 21:
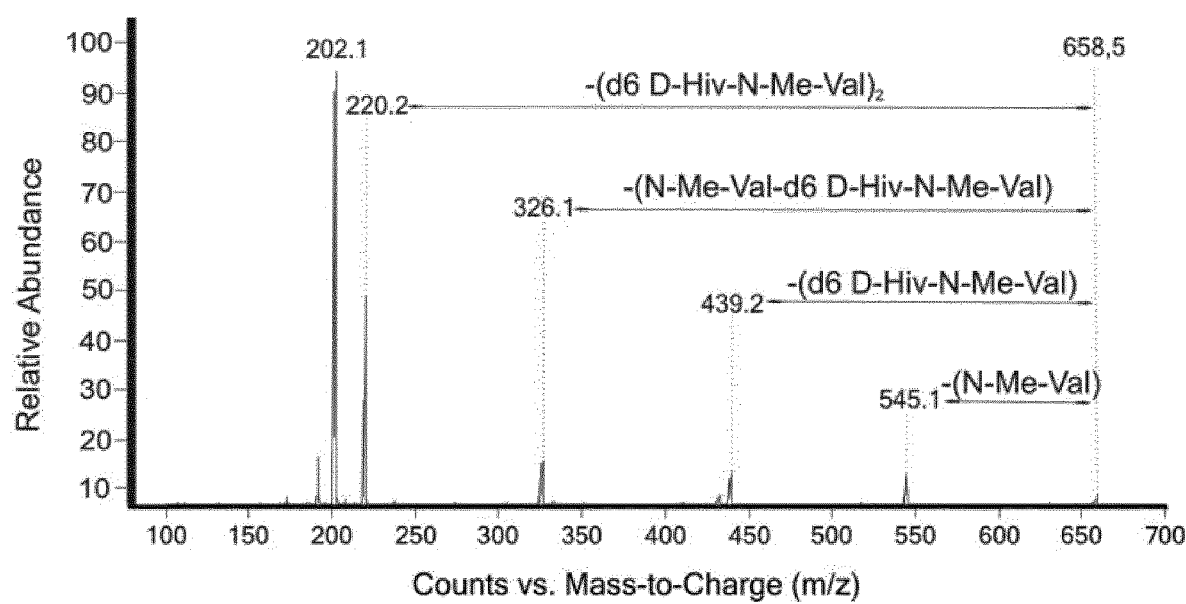
FIG. 21 Extracted ion chromatogramm of d18 enniatin B obtained from the feeding dependent *A. niger* strain. This substance can be used as an internal standard for the determination of enniatin in crops. A deuterated standard has never been reported yet. The system allows the synthesis of deuterated enniatin variants as well as beauvericin variants.
Figure 22:
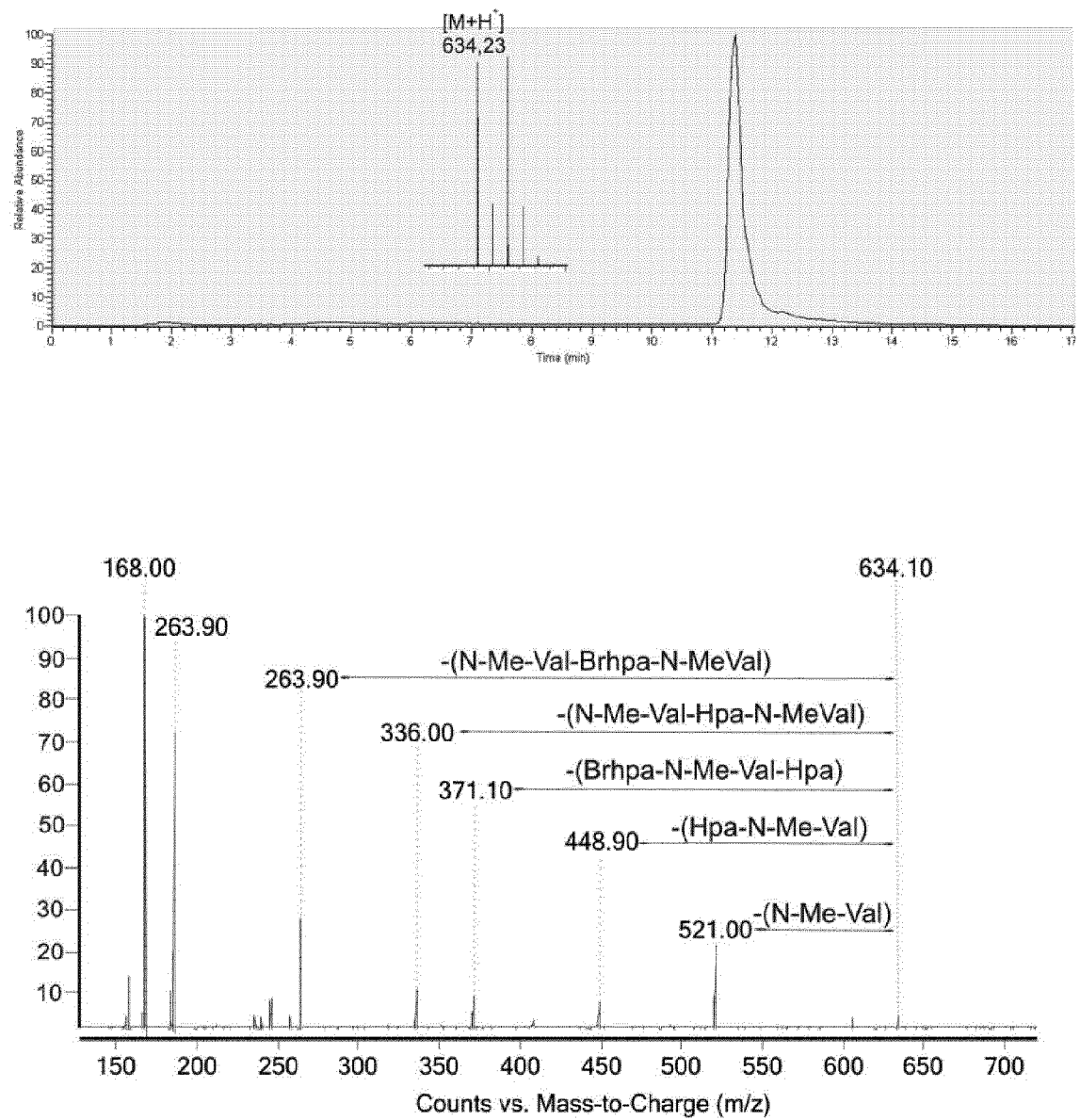
FIG. 22 Total Ion Chromatogram of [3-Br-Lac]$_1$ [Lac]$_2$ Enniatin B and Tandem MS of [3-Br-Lac]$_1$ [Lac]$_2$ Enniatin B.
Figure 23:
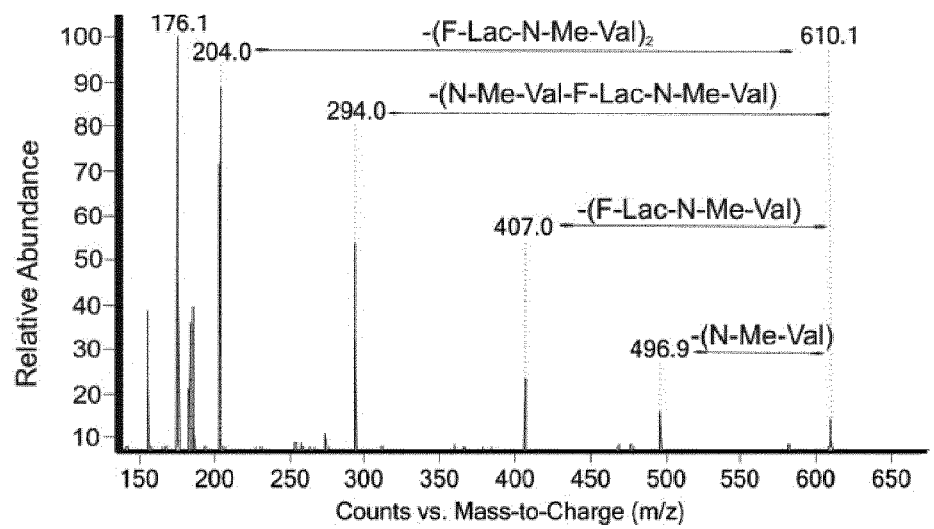
FIG. 23 Tandem MS of [3-F-Lac]$_3$ Enniatin B.
Figure 24:
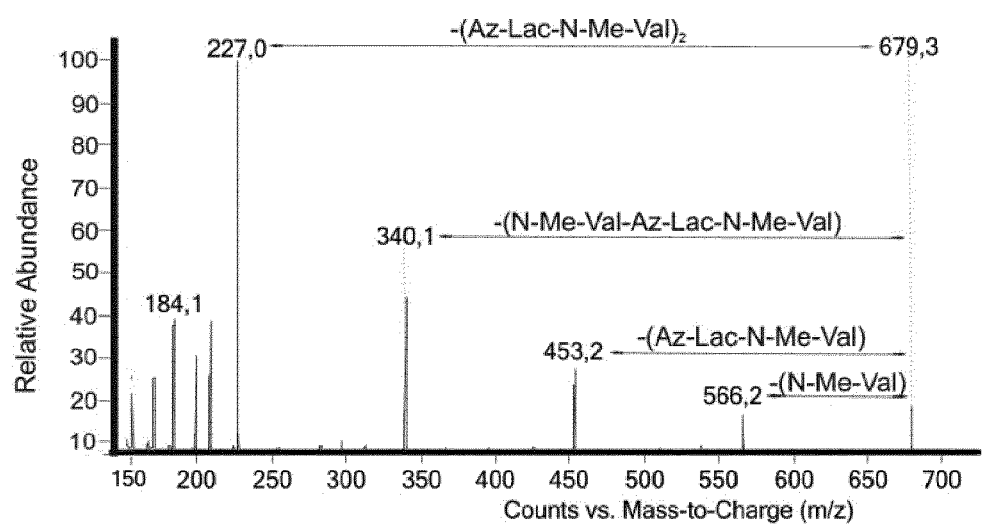
FIG. 24 Tandem MS [3-N$_3$-Lac]$_3$ enniatin B. The azido group allows 1,3 dipolar cyclo addition for further chemical modification of the enniatin variant.
Figure 25:
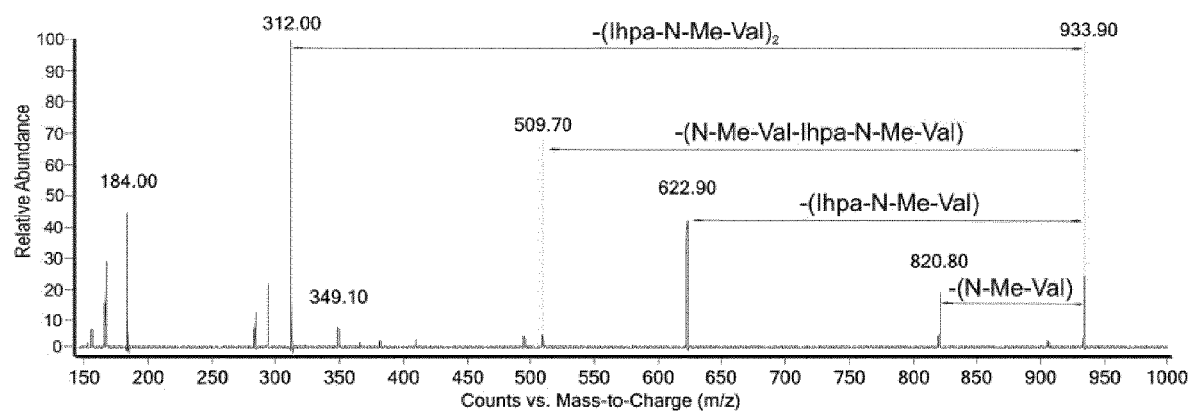
FIG. 25 Tandem MS of [3-I-Lac]$_3$ enniatin B obtained by precursor directed biosynthesis in *A. niger*. Iodine containing enniatin variants undergo Elimination and substitution reactions.

An equivalent approach provided Beauvericin (see FIG. 11a).

B) METHODS AND ANALYTICAL DATA FOR GENERATION OF HYBRID SYNTHETASE

1. Cloning Strategy for Generating Chimeric Synthetases (See FIGS. 12-14, 18)

Expression plasmids using T7 promoter for heterologous expression in E. coli were purchased from Merck Millipore. Protein expression of all hybrid genes coding for NRPS were cloned by insertion via restrictions sites into the high copy pRSF-Duet1 plasmid. Combinatorial biosynthesis was performed by λ-recombination mediated system. Sequences of desired domain or module were amplified via PCR (Q5-polymerase, High-Fidelity, New England Biolabs) and sub cloned into pRSF-Duet1. A selection marker (coding sequence for streptomycin resistance) which is needed after recombination was integrated at a single restriction site into the subcloned fragment. Positive clones were screened for streptomycin resistance and subsequently removed resistance by restriction and self-ligation of the flanking single cutter site. Electro competent E. coli BW25113 cells were transformed with the desired vector with the original NRPS gene cultivated at 30° C. to save the heat labile plasmid pIJ790 harbouring λ-recombinase RED (gam, bet, exo) and single DNA protecting proteins. Recombinase expression was induced by addition of arabinose before E. coli BW25113 cells were transformed with the module containing plasmid up to 70 base pairs were chosen as overlapping homologous region (modified after Gust et al./Zhang et al. 1998).

2. Production of Chimeric Enniatins and Beauvericins with Chimeric Synthetases Expressed in E. coli Culture Conditions and Extraction E. coli Bl21gold cells were pre cultured over night at 37° C. in 20 ml of LB-medium at 200 rpm. Inoculation of main culture (50 ml LB-medium) with pre culture in the ration 1:100 was incubated to an $OD_{600}$ of 0.6 at 37° C. and induced with IPTG at a final concentration of 0.25 mM (Carl Roth) and further incubated for protein expression and peptide production at 18° C. for 24-48 h 200 rpm. Cells were harvested and cell pellet was extracted with 5 ml of MeOH (technical grade). The suspension was sonified for 5 minutes and supernatant was evaporated.

Analysis with HPLC-ESI-MS, HPLC-ESI-MS and Tandem MS (See FIGS. 15-17, 19-25)

For complex analytics crude extracts were resolved in 200-500 µl MeOH (HPLC grade) and suspended solids were centrifuged at 14 000×g. HPLC-ESI-MS was carried out for scanning new derivatives. For all measurements we used Agilent technologies regarding columns and HPLC/MS equipment (Eclipse Plus C18, 2.1×50 mm; UHPLC 1290 Infinity-Series, ESI-Triple-Quadrupol-MS, 6460 Series). By using a mobile phase system we added of 0.1% of HCOOH in $H_2O$ (A) and ACN (B) with a gradient from 5% to 100% over 2.5 min and subsequently 100% B for 5.5 more minutes.

The invention claimed is:

1. A method for obtaining at least one non-ribosomal peptide, the method comprising:
the step of heterologous expression of at least one non-ribosomal peptide synthetase (NRPS) of at least one non-ribosomal peptide in filamentous fungus *Aspergillus niger*,
wherein the at least one NRPS is a cyclodepsipeptide synthetase selected from the group containing Enniatin, PF1022, Beauvericin and Bassianolide synthetase,
wherein an inducible expression system integrated into the genome of the filamentous fungus *Aspergillus niger* is used for heterologous expression of the at least one NRPS,
wherein the inducible expression system comprises at least one expression cassette, the at east one expression cassette comprising a first module for constitutive expression of a tetracycline dependent transactivator rtTA2, a second module harboring the rtTA2-dependent promoter for inducible expression of the at least one NRPS and a polynucleotide encoding the at least one non-ribosomal peptide synthetase and a third module for integrating the at least one expression cassette into the fungal genome by homologous or heterologous recombination using appropriate selection markers.

2. The method according to claim 1, wherein the at least one NRPS comprises modules and/or domains of at least two different cyclodepsipeptide synthetases.

3. The method according to claim 2, wherein the at least one NRPS comprises module 1 of the cyclodepsipeptide synthetase and module 2, PCP domain and C-domain of another cyclodepsipeptide synthetase.

4. The method according to claim 1, wherein the expression cassette further comprises genes encoding for biosynthetic enzymes of metabolic precursors or metabolic intermediates.

5. The method according to claim 4, wherein the genes encode dehydrogenases capable of transforming amino acids to hydroxycarboxylic acids.

6. The method according to claim 1, wherein the culture media used for heterologous expression of the at least one NRPS comprises talcum, titanate, silica, or aluminum oxide particles.

7. The method according to claim 1, wherein the culture media used for heterologous expression of the at least one NRPS comprises 5-20 mM, of at least one hydroxycarboxylic acid and 10-30 mM of at least one amino acid.

8. The method according to claim 1, that the culture media used for heterologous expression of the at least one NRPS comprises at least on D- or L-hydroxycarboxylic add of the general formula R'—CHOH—CO$_2$H wherein R' is selected from a group comprising:
substituted and non-substituted $C_1$-$C_{50}$-alkyl, substituted and non-substituted $C_2$-$C_{50}$-alkenyl, substituted and non-substituted $C_2$-$C_{50}$-alkinyl substituted and non-substituted $C_3$-$C_{10}$-cycloalkyl, substituted and non-substituted $C_5$-$C_7$-cycloalkenyl, which in each case can be interrupted by one or more oxygen atoms, sulfur atoms, substituted or mono-substituted nitrogen atoms, double bonds and/or by one or more groups of the type —C(O)O—, —OC(O)—, —C(O)—, NHC(O)O—, —OC(O)NH— and/or —OC(O)O-aryl, heteroaryl, —CH$_2$-aryl or —CH$_2$-heteroaryl, wherein aryl and heteroaryl are substituted or non-substituted.

9. The method according in to claim 1, wherein the culture media used for heterologous expression of the at least one NRPS comprises at least one D- or L-amino add of the general formulate R$^2$—CHNH$_2$—CO$_2$H, where in R$^2$ is selected from the group comprising:
substituted and non-substituted $C_1$-$C_{50}$-alkyl, substituted and non-substituted $C_2$-$C_{50}$-alkenyl, substituted and non-substituted $C_2$-$C_{50}$-alkinyl, substituted and non-substituted $C_3$-$C_{10}$-cycloalkyl, substituted and non-substituted $C_5$-$C_7$-cycloalkenyl, which in each case can be interrupted by one or more oxygen atoms, sulfur atoms, substituted or mono-substituted nitrogen atoms, double bonds and/or by one or more groups of the type —C(O)O—, —OC(O)—, —C(O)—, NHC(O)O—, —OC(O)NH— and/or —OC(O)O—.

* * * * *

UNITED STATES PATENT AND TRADEMARK OFFICE
CERTIFICATE OF CORRECTION

PATENT NO. : 10,738,316 B2
APPLICATION NO. : 15/127645
DATED : August 11, 2020
INVENTOR(S) : Simon Boecker et al.

It is certified that error appears in the above-identified patent and that said Letters Patent is hereby corrected as shown below:

In the Claims

Column 61, Lines 26-27, Claim 1:
After "at least one expression cassette, the at"
Delete "east" and
Insert -- least --.

Column 62, Line 20, Claim 8:
After "The method according to claim 1,"
Delete "that" and
Insert -- wherein --.

Column 62, Line 21-22, Claim 8:
After "at least one NRPS comprises at least"
Delete "on" and
Insert -- one --.

Column 62, Line 22, Claim 8:
After "D- or L-hydroycarboxylic"
Delete "add" and
Insert -- acid --.

Column 62, Line 38, Claim 9:
After "D- or L-hydroycarboxylic"
Delete "add" and
Insert -- acid --.

Column 62, Lines 38-39, Claim 9:
After "of the general"

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*

Delete "formulate" and
Insert -- formula --.